US009096590B2

(12) United States Patent
Ren et al.

(10) Patent No.: US 9,096,590 B2
(45) Date of Patent: Aug. 4, 2015

(54) SUBSTITUTED BENZOXAZOLES AS PI3 KINASE INHIBITORS

(75) Inventors: Pingda Ren, San Diego, CA (US); Yi Liu, San Diego, CA (US); Liansheng Li, San Diego, CA (US); Katrina Chan, Fremont, CA (US); Troy Edward Wilson, San Marino, CA (US); Simon Fraser Campbell, Kent (GB)

(73) Assignee: Intellikine LLC, La Jolla, CA (US)

( * ) Notice: Subject to any disclaimer, the term of this patent is extended or adjusted under 35 U.S.C. 154(b) by 0 days.

(21) Appl. No.: 13/699,611

(22) PCT Filed: May 24, 2011

(86) PCT No.: PCT/US2011/037742
§ 371 (c)(1),
(2), (4) Date: Jun. 10, 2013

(87) PCT Pub. No.: WO2011/149937
PCT Pub. Date: Dec. 1, 2011

(65) Prior Publication Data
US 2013/0261102 A1    Oct. 3, 2013

Related U.S. Application Data

(60) Provisional application No. 61/347,814, filed on May 24, 2010, provisional application No. 61/426,466, filed on Dec. 22, 2010, provisional application No. 61/445,981, filed on Feb. 23, 2011.

(51) Int. Cl.
C07D 498/04        (2006.01)
C07D 471/04        (2006.01)

(52) U.S. Cl.
CPC ................... C07D 471/04 (2013.01)

(58) Field of Classification Search
CPC ................................... C07D 498/04
USPC .............. 544/148, 350, 368; 546/209, 268.1; 548/217, 335.1, 453, 950
See application file for complete search history.

(56) References Cited

U.S. PATENT DOCUMENTS

| | | | |
|---|---|---|---|
| 2,313,993 | A | 3/1943 | Gaspar |
| 6,057,320 | A | 5/2000 | Spada et al. |
| 6,632,809 | B2 | 10/2003 | Grillot et al. |
| RE40,245 | E | 4/2008 | Grillot et al. |
| 2006/0036061 | A1 | 2/2006 | Shin et al. |
| 2006/0106013 | A1 | 5/2006 | Breitfelder et al. |
| 2007/0213355 | A1 | 9/2007 | Capraro et al. |
| 2009/0054405 | A1 | 2/2009 | Booker et al. |
| 2010/0184760 | A1 | 7/2010 | Ren et al. |
| 2012/0294930 | A1* | 11/2012 | Ren et al. ................ 424/450 |

FOREIGN PATENT DOCUMENTS

| | | |
|---|---|---|
| EP | 1488792 A2 | 12/2004 |
| EP | 1488792 A3 | 1/2005 |
| EP | 871448 B1 | 3/2005 |
| EP | 1557410 A2 | 7/2005 |
| EP | 1557410 A3 | 4/2006 |
| EP | 1341769 B1 | 10/2007 |
| EP | 1557410 B1 | 9/2009 |
| GB | 1323210 A | 7/1973 |
| WO | WO 02/060879 A2 | 8/2002 |
| WO | WO 02/060879 A3 | 3/2003 |
| WO | WO 2005/009389 A2 | 2/2005 |
| WO | WO 2005/009389 A3 | 9/2005 |
| WO | WO 2007/095588 A1 | 8/2007 |
| WO | WO 2008/118486 A1 | 10/2008 |
| WO | WO 2008/152394 A1 | 12/2008 |
| WO | WO 2009/017822 A2 | 2/2009 |
| WO | WO 2009/017822 A3 | 4/2009 |
| WO | WO 2009/085945 A1 | 7/2009 |
| WO | WO 2010/036380 A1 | 4/2010 |
| WO | WO 2011/022439 A1 | 2/2011 |

OTHER PUBLICATIONS

U.S. Appl. No. 13/391,254, filed Oct. 15, 2012, Ren et al.
3rd party observation dated Oct. 5, 2012 against PatentApplication No. P2012-0042 in Domican Republic.
3rd party observation dated Oct. 5, 2012 against PatentApplication No. P2012-0110 in Costa Rica.
Berndt, et al. The p110 delta structure: mechanisms for selectivity and potency of new PI(3)K inhibitors. Nat Chem Biol. Feb. 2010;6(2):117-24.
Cameron, et al. Metal-metal interactions in a novel hybrid metallopolymer. Journal of the American Chemical Society. 1999; 121(50):11773-11779.
European search report dated Dec. 20, 2012 for EP Application No. 10810518.0.
Garin, et al. Diheterocyclic compounds from dithiocarbamates and derivatives there of. II. 2,2'-diamino-6,6'-bibenzoazoles. Journal of Heterocyclic Chemistry. 1990; 27:321-326.
International search report and written opinion dated Aug. 20, 2012 for PCT Application No. US2012/026406.
International search report and written opinion dated Aug. 22, 2011 for PCT Application No. US11/37742.
International search report and written opinion dated Nov. 16, 2010 for PCT Application No. US10/45816.

(Continued)

Primary Examiner — Douglas M Willis
(74) Attorney, Agent, or Firm — Honigman Miller Schwartz and Cohn LLP; Lucy Yang; Jonathan P. O'Brien

(57) ABSTRACT

The present invention provides substituted benzoxazole compounds of the Formula:

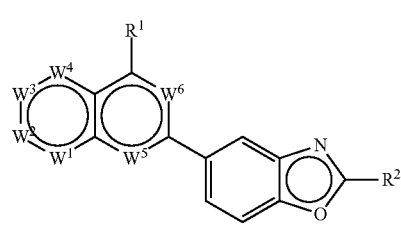

wherein the variables $R^1$, $R^2$, $W^1$, $W^2$, $W^3$, $W^4$, $W^5$, are $W^6$ are defined herein. The compounds are useful as phosphoinositide 3-kinase (PI3 kinase) inhibitors.

22 Claims, No Drawings

(56) References Cited

OTHER PUBLICATIONS

Koch, et al. N-{4-[(4-Fluorophenyl)pyrido[2,3-b]-pyrazin-2-yl]-2-pyridyl} isopropylamine. Acta Crystallogr Sect E Struct Rep Online. Oct. 1, 2009; 65(Pt 10): o2557.

Singh, et al. Synthetic utility of catalytic Fe(II)/Fe(II) redox cycling towards fused heterocycles: a facile access to substituted benzimidazole, bisbenzimidazole and imidazopyridine derivatives. Synthesis, Georg Thieme Verlag. 2000; 10:1380-1390.

Yaguchi, et al. Antitumor activity of ZSTK474, a new phosphatidylinositol 3-kinase inhibitor. J Natl Cancer Inst. Apr. 19, 2006;98(8):545-56.

* cited by examiner

SUBSTITUTED BENZOXAZOLES AS PI3 KINASE INHIBITORS

This application claims the benefit of U.S. Provisional Application Ser. No. 61/347,814, filed May 24, 2010, U.S. Provisional Application Ser. No. 61/426,466, filed Dec. 22, 2010, and U.S. Provisional Application Ser. No. 61/445,981, filed Feb. 23, 2011, each of which is hereby incorporated by reference in its entirety.

BACKGROUND OF THE INVENTION

The activity of cells can be regulated by external signals that stimulate or inhibit intracellular events. The process by which stimulatory or inhibitory signals are transmitted into and within a cell to elicit an intracellular response is referred to as signal transduction. Over the past decades, cascades of signal transduction events have been elucidated and found to play a central role in a variety of biological responses. Defects in various components of signal transduction pathways have been found to account for a vast number of diseases, including numerous forms of cancer, inflammatory disorders, metabolic disorders, vascular and neuronal diseases (Gaestel et al. *Current Medicinal Chemistry* (2007) 14:2214-2234).

Kinases represent a class of important signaling molecules. Kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphorylate substrates on serine and/or threonine residues (e.g., mTorC1, mTorC2, ATM, ATR, DNA-PK, Akt), and dual-specificity kinases which phosphorylate substrates on tyrosine, serine and/or threonine residues.

Lipid kinases are enzymes that catalyze the phosphorylation of lipids within cells. These enzymes, and the resulting phosphorylated lipids and lipid-derived biologically active organic molecules, play a role in many different physiological processes, including cell proliferation, migration, adhesion, and differentiation. A particular group of lipid kinases comprises membrane lipid kinases, i.e., kinases that catalyze the phosphorylation of lipids contained in or associated with cell membranes. Examples of such enzymes include phosphinositide(s) kinases (such as PI3-kinases, PI4-Kinases), diacylglycerol kinases, and sphingosine kinases.

The phosphoinositide 3-kinases (PI3Ks) signaling pathway is one of the most highly mutated systems in human cancers. PI3K signaling is involved in many other disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

PI3Ks are members of a unique and conserved family of intracellular lipid kinases that phosphorylate the 3'-OH group on phosphatidylinositols or phosphoinositides. The PI3K family comprises 15 kinases with distinct substrate specificities, expression patterns, and modes of regulation (Katso et al., 2001). The class I PI3Ks (p110α, p110β, p110δ, and p110γ) are typically activated by tyrosine kinases or G-protein coupled receptors to generate PIP3, which engages downstream effectors such as those in the pathways of Akt/PDK1, mTOR, the Tec family kinases, and the Rho family GTPases. The class II and III PI3-Ks play a key role in intracellular trafficking through the synthesis of PI(3)P and PI(3,4)P$_2$.

The alpha (α) isoform of PI3K has been implicated, for example, in a variety of human cancers. Angiogenesis has been shown to selectively require the a isoform of PI3K in the control of endothelial cell migration. (Graupera et al, Nature 2008; 453; 662-6). Mutations in the gene coding for PI3K α or mutations which lead to upregulation of PI3K α a are believed to occur in many human cancers such as lung, stomach, endometrial, ovarian, bladder, breast, colon, brain and skin cancers. Often, mutations in the gene coding for PI3K α are point mutations clustered within several hotspots in helical and kinase domains, such as E542K, E545K, and H1047R. Many of these mutations have been shown to be oncogenic gain-of-function mutations. Because of the high rate of PI3K α mutations, targeting of this pathway may provide valuable therapeutic opportunities. While other PI3K isoforms such as PI3K δ or PI3K γ are expressed primarily in hematopoietic cells, PI3K α, along with PI3K β, is expressed constitutively.

The delta (δ) isoform of class I PI3K has been implicated, in particular, in a number of diseases and biological processes. PI3K δ is expressed primarily in hematopoietic cells including leukocytes such as T-cells, dendritic cells, neutrophils, mast cells, B-cells, and macrophages. PI3K δ is integrally involved in mammalian immune system functions such as T-cell function, B-cell activation, mast cell activation, dendritic cell function, and neutrophil activity. Due to its integral role in immune system function, PI3K δ is also involved in a number of diseases related to undesirable immune response such as allergic reactions, inflammatory diseases, inflammation mediated angiogenesis, rheumatoid arthritis, auto-immune diseases such as lupus, asthma, emphysema and other respiratory diseases. Other class I PI3K involved in immune system function includes PI3K γ, which plays a role in leukocyte signaling and has been implicated in inflammation, rheumatoid arthritis, and autoimmune diseases such as lupus.

Downstream mediators of the PI3K signal transduction pathway include Akt and mammalian target of rapamycin (mTOR). Akt possesses a pleckstrin homology (PH) domain that binds PIP3, leading to Akt kinase activation. Akt phosphorylates many substrates and is a central downstream effector of PI3K for diverse cellular responses. One important function of Akt is to augment the activity of mTOR, through phosphorylation of TSC2 and other mechanisms. mTOR is a serine-threonine kinase related to the lipid kinases of the PI3K family. mTOR has been implicated in a wide range of biological processes including cell growth, cell proliferation, cell motility and survival. Disregulation of the mTOR pathway has been reported in various types of cancer. mTOR is a multifunctional kinase that integrates growth factor and nutrient signals to regulate protein translation, nutrient uptake, autophagy, and mitochondrial function.

Dysregulation of signaling pathways mediated by many other kinases is a key factor in the development of human diseases. Aberrant or excessive protein kinase activity or expression has been observed in many disease states including benign and malignant proliferative diseases, disorders such as allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

As such, kinases particularly lipid kinases such as PI3Ks and protein kinases such as mTor are prime targets for drug development. The present invention addresses a need in the art by providing a new class of kinase inhibitors.

SUMMARY OF THE INVENTION

In one aspect, the invention provides a compound of Formula I:

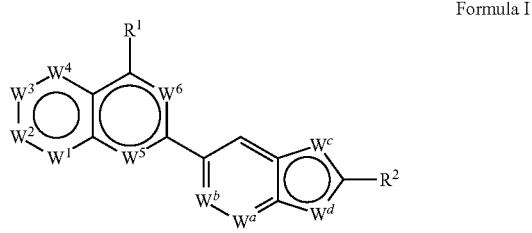

Formula I or its pharmaceutically acceptable salts thereof, wherein:
$W^1$ is N, $NR^3$, or $CR^3$; $W^2$ is N, $NR^4$, $CR^4$, or C=O; $W^3$ is N, $NR^5$ or $CR^5$; $W^4$ is N or $NR^6$, wherein no more than two N atoms and no more than two C=O groups are adjacent;
$W^5$ is N or $NR^7$;
$W^6$ is N or $CR^8$;
$W^a$ and $W^b$ are independently N or $CR^9$;
one of $W^c$ and $W^d$ is N, and the other is O, $NR^{10}$, or S;
$R^1$ and $R^2$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;
$R^3$ and $R^4$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; or $R^3$ and $R^4$ taken together form a cyclic moiety;
$R^5$, $R^6$, $R^7$ and $R^8$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;
$R^9$ is alkyl or halo; and
$R^{10}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety.

In some embodiments of the compound of Formula I, $W^2$ is $CR^4$, for example where $R^4$ is alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety. In some embodiments, $R^4$ is cycloalkyl, heterocycloalkyl, aryl or heteroaryl.

In other embodiments, $W^3$ is $CR^5$. For example, both $W^2$ and $W^3$ are CH. In some embodiments, $W^6$ is $CR^8$. In other embodiments, $W^1$ is N or $CR^3$. In some embodiments, $W^b$ is $CR^9$ or N. In some embodiments, $W^4$ is N. In other embodiments, $W^5$ is N.

In some embodiments, $W^a$ is $CR^9$ and $R^9$ is alkyl or hydrogen. Alternatively, $W^a$ is $CR^9$ and $R^9$ is alkyl. In still other embodiments, $W^a$ and $W^b$ are $CR^9$ and $R^9$ is hydrogen.

In some embodiments, $W^c$ is N and $W^d$ is O. In other embodiments, $R^2$ is amino. In still other embodiments, $R^1$ is hydrogen.

In some embodiments, the compound of the invention has the Formula:

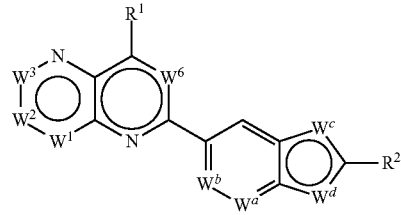

For example, the compound has the Formula:

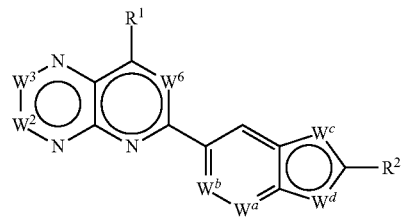

In some embodiments, $W^c$ is N and $W^d$ is O. In other embodiments, $W^2$ and $W^3$ are CH. In still other embodiments, $R^2$ is amino. In some embodiments, $R^1$ is H.

In some embodiments of a compound of the invention, $W^2$ is $CR^4$ and $R^4$ is alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety. For example, $R^4$ is aryl, heteroaryl, heterocycloalkyl, or NR'R" wherein R' and R" are taken together with nitrogen to form a cyclic moiety. Alternatively, $R^4$ is 5 or 6-membered heteroaryl. In another instance, $R^4$ is NR'R" and R' and R" are taken together with nitrogen to form a 4-, 5-, or 6-membered heterocyclic moiety, for example morpholine, piperazine, azetidine, pyrrolidine, or piperidine. In some embodiments, $R^4$ can be further substituted with alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety.

In yet another embodiment, the present invention provides a composition comprising a pharmaceutically acceptable excipient and one or more compound disclosed herein. In some embodiments, the composition is a liquid, solid, semi-solid, gel, or an aerosol form.

In still yet another embodiment, the present invention provides a method for inhibiting a phosphatidyl inositol-3 kinase (PI3 kinase), comprising: contacting the PI3 kinase with an effective amount of a compound disclosed herein. In some embodiments, the PI3 kinase is PI3 kinase alpha. The step of contacting may further comprise contacting a cell that expresses one or more type I PI3 kinases, including PI3 kinease alpha. In some embodiments, the method further comprises administering a second therapeutic agent to the cell.

The present invention also provides a method for treating a condition associated with PI3 kinase, comprising administering to a subject in need thereof an effective amount of the compound disclosed herein. In some embodiments, the condition associated with PI3 kinase is selected from the group consisting of asthma, emphysema, bronchitis, psoriasis, allergy, anaphylaxis, rheumatoid arthritis, graft versus host disease, lupus erythematosus, psoriasis, restenosis, benign prostatic hypertrophy, diabetes, pancreatitis, proliferative glomerulonephritis, diabetes-induced renal disease, inflammatory bowel disease, atherosclerosis, eczema, scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the appended claims define the scope of the invention and that methods and structures within the scope of these claims and their equivalents be covered thereby.

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" includes plural references unless the context clearly dictates otherwise.

As used herein, "agent" or "biologically active agent" refers to a biological, pharmaceutical, or chemical compound or other moiety. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g., bind to) the target, compounds that initiate or enhance a biological activity of the target polypeptide by interacting with other members of the signal transduction pathway of which the target polypeptide is a member are also specifically included within this definition.

The terms "antagonist" and "inhibitor" are used interchangeably, and they refer to a compound having the ability to inhibit a biological function of a target protein, whether by inhibiting the activity or expression of the target protein. Accordingly, the terms "antagonist" and "inhibitors" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor, or an undesired immune response as manifested in autoimmune disease.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The terms "co-administration," "administered in combination with," and their grammatical equivalents, encompass administration of two or more agents to an animal so that both agents and/or their metabolites are present in the animal at the same time. Co-administration includes simultaneous administration in separate compositions, administration at different times in separate compositions, or administration in a composition in which both agents are present.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

"Treatment", "treating", "palliating" and "ameliorating", as used herein, are used interchangeably. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

The term "selective inhibition" or "selectively inhibit" as applied to a biologically active agent refers to the agent's ability to selectively reduce the target signaling activity as compared to off-target signaling activity, via direct or interact interaction with the target.

The term "B-ALL" as used herein refers to B-cell Acute Lymphoblastic Leukemia.

"Subject" refers to an animal, such as a mammal, for example a human. The methods described herein can be useful in both human therapeutics and veterinary applications. In some embodiments, the patient is a mammal, and in some embodiments, the patient is human.

"Radiation therapy" means exposing a patient, using routine methods and compositions known to the practitioner, to radiation emitters such as alpha-particle emitting radionuclelotides (e.g., actinium and thorium radionuclides), low linear energy transfer (LET) radiation emitters (i.e., beta emitters), conversion electron emitters (e.g., strontium-89 and samarium-153-EDTMP, or high-energy radiation, including without limitation x-rays, gamma rays, and neutrons.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

The term "in vivo" refers to an event that takes place in a subject's body.

The term "in vitro" refers to an event that takes places outside of a subject's body. For example, an in vitro assay encompasses any assay run outside of a subject assay. In vitro assays encompass cell-based assays in which cells alive or dead are employed. In vitro assays also encompass a cell-free assay in which no intact cells are employed.

Unless otherwise stated, structures depicted herein are also meant to include compounds which differ only in the presence of one or more isotopically enriched atoms. For example, compounds having the present structures wherein hydrogen is replaced by deuterium or tritium, or wherein carbon atom is replaced by $^{13}$C- or $^{14}$C-enriched carbon, are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features.

The following abbreviations and terms have the indicated meanings throughout PI3-K=Phosphoinositide 3-kinase; PI=phosphatidylinositol; PDK=Phosphoinositide Dependent Kinase; DNA-PK=Deoxyribose Nucleic Acid Dependent Protein Kinase; PIKK=Phosphoinositide Kinase Like Kinase; AIDS=Acquired Immuno Deficiency Syndrome; TLC=Thin Layer Chromatography; MeOH=Methanol; and CHCl$_3$=Chloroform.

Abbreviations used herein have their conventional meaning within the chemical and biological arts.

"Alkyl" refers to a straight or branched hydrocarbon chain radical consisting solely of carbon and hydrogen atoms, containing no unsaturation, having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_4$ alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl(t-butyl), 3-methylhexyl, 2-methylhexyl, and the like. Unless stated otherwise specifically in the specification, an alkyl group is optionally substituted by one or more of substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$ where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e., $C_2$-$C_{10}$ alkenyl). Whenever it appears herein, a numerical range such as "2 to 10" refers to each integer in the given range; e.g., "2 to 10 carbon atoms" means that the alkenyl group may consist of 2 carbon atoms, 3 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl" refers to a straight or branched hydrocarbon chain radical group consisting solely of carbon and hydrogen atoms, containing at least one triple bond, having from two to ten carbon atoms (i.e., $C_2$-$C_{10}$ alkynyl). Whenever it appears herein, a numerical range such as "2 to 10" refers to each integer in the given range; e.g., "2 to 10 carbon atoms" means that the alkynyl group may consist of 2 carbon atoms, 3 carbon atoms, etc., up to and including 10 carbon atoms. In certain embodiments, an alkynyl comprises two to eight carbon atoms. In other embodiments, an alkynyl has two to five carbon atoms (e.g., $C_2$-$C_5$ alkynyl). The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Carboxaldehyde" refers to a —(C=O)H radical.

"Carboxyl" refers to a —(C=O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e., $C_2$-$C_{10}$ cycloalkyl). Whenever it appears herein, a numerical range such as "3 to 10" refers to each integer in the given range; e.g., "3 to 10 carbon atoms" means that the cycloalkyl group may consist of 3 carbon atoms, etc., up to and including 10 carbon atoms. In some embodiments, it is a $C_3$-$C_8$ cycloalkyl radical. In some embodiments, it is a $C_3$-$C_5$ cycloalkyl radical. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)$OR^a$, —OC(O)N($R^a)_2$, —C(O)N($R^a)_2$, —N($R^a$)C(O)$OR^a$, —N($R^a$)C(O)$R^a$, —N($R^a$)C(O)N($R^a)_2$, N($R^a$)C(N$R^a$)N($R^a)_2$, —N($R^a$)S(O)$_t R^a$ (where t is 1 or 2), —S(O)$_t OR^a$ (where t is 1 or 2), —S(O)$_t$N($R^a)_2$ (where t is 1 or 2), or PO$_3$($R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxy" refers to the group —O-alkyl, including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, $C_1$-$C_4$ alkyl, is an alkyl group which encompasses both straight and branched chain alkyls of from 1 to 4 carbon atoms.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, $SR^a$, —OC(O)—$R^a$, —$N(R^a)_2$, —C(O)$R^a$, —C(O)$OR^a$, —OC(O)N($R^a)_2$, —C(O)N($R^a)_2$, —N($R^a$)C(O)$OR^a$, —N($R^a$)C(O)$R^a$, —N($R^a$)C(O)N($R^a)_2$, N($R^a$)C(N$R^a$)N($R^a)_2$, —N($R^a$)S(O)$_t R^a$ (where t is 1 or 2), —S(O)$_t OR^a$ (where t is 1 or 2), —S(O)$_t$N($R^a)_2$ (where t is 1 or 2), or PO$_3$($R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C=O)— attached through the carbonyl carbon wherein the alkoxy group has the indicated number of carbon atoms. Thus a $C_1$-$C_6$ alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group. In some embodiments, $C_1$-$C_4$ alkoxy, is an alkoxy group which encompasses both straight and branched chain alkoxy groups of from 1 to 4 carbon atoms.

The term "substituted alkoxycarbonyl" refers to the group (substituted alkyl)-O—C(O)— wherein the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)$OR^a$, —OC(O)N($R^a)_2$, —C(O)N($R^a)_2$, —N($R^a$)C(O)$OR^a$, —N($R^a$)C(O)$R^a$, —N($R^a$)C(O)N($R^a)_2$, N($R^a$)C(N$R^a$)N($R^a)_2$, —N($R^a$)S(O)$_t R^a$ (where t is 1 or 2), —S(O)$_t OR^a$ (where t is 1 or 2), —S(O)$_t$N($R^a)_2$ (where t is 1 or 2), or PO$_3$($R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)—, and (heterocycloalkyl)-C(O)—, wherein the group is attached to the parent structure through the carbonyl functionality. In some embodiments, it is a $C_1$-$C_{10}$ acyl radical which refers to the total number of chain or ring atoms of the alkyl, aryl, heteroaryl or heterocycloalkyl portion of the acyloxy group plus the carbonyl carbon of acyl, i.e. three other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, $SR^a$, —OC(O)—$R^a$, —$N(R^a)_2$, —C(O)$R^a$, —C(O)$OR^a$, —OC(O)N($R^a)_2$, —C(O)N($R^a)_2$, —N$R^a$)C(O)$OR^a$, —N($R^a$)C(O)$R^a$, —N($R^a$)C(O)N($R^a)_2$, N($R^a$)C(N$R^a$)N($R^a)_2$, —N($R^a$)S(O)$_t R^a$ (where t is 1 or 2), —S(O)$_t OR^a$ (where t is 1 or 2), —S(O)$_t$N($R^a)_2$ (where t is 1 or 2), or PO$_3$($R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C=O)O— radical wherein "R" is alkyl, aryl, heteroaryl, heteroalkyl, or heterocycloalkyl, which are as described herein. In some embodiments, it is a $C_1$-$C_4$ acyloxy radical which refers to the total number of chain or ring atoms of the alkyl, aryl, heteroaryl or heterocycloalkyl portion of the acyloxy group plus the carbonyl carbon of acyl, i.e. three other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)$OR^a$, —OC(O)N($R^a)_2$, —C(O)N($R^a)_2$, —N($R^a$)C(O)$OR^a$, —N($R^a$)C(O)$R^a$, —N($R^a$)C(O)N($R^a)_2$, N($R^a$)C(N$R^a$)N($R^a)_2$, —N($R^a$)S(O)$_t R^a$ (where t is 1 or 2-S(O)$_t OR^a$ (where t is 1 or 2), —S(O)$_t$N($R^a)_2$ (where t is 1 or 2), or PO$_3$($R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amino" or "amine" refers to a —N($R^a$)$_2$ radical group, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N($R^a$)$_2$ group has two $R^a$ other than hydrogen they can be combined with the nitrogen atom to form a 4-, 5-, 6-, or 7-membered ring. For example, —N($R^a$)$_2$ is meant to include, but not be limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl and each of these moieties may be optionally substituted as defined herein.

The term "substituted amino" also refers to N-oxides of the groups —NH$R^a$, and N$R^a$$R^a$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. In some embodiments it is a $C_1$-$C_4$ amido or amide radical, which includes the amide carbonyl in the total number of carbons in the radical. The $R_2$ of —N(R)$_2$ of the amide may optionally be taken together with the nitrogen to which it is attached to form a 4-, 5-, 6-, or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound of Formula (I), thereby forming a prodrug. Any amine, hydroxy, or carboxyl side chain on the compounds described herein can be amidified. The procedures and specific groups to make such amides are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

"Aromatic" or "aryl" refers to an aromatic radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl-radical wherein the arylalkyl moiety is attached via the alkyl portion of the moiety. Aryl and alkyl are as disclosed herein and are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). Any amine, hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl", "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given, e.g., $C_1$-$C_4$ heteroalkyl which refers to the chain length in total, which in this example is 4 atoms long. For example, a —CH$_2$OCH$_2$CH$_3$ radical is referred to as a "$C_4$" heteroalkyl, which includes the heteroatom center in the atom chain length description. Connection to the rest of the molecule may be through either a heteroatom or a carbon in the heteroalkyl chain. A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers "to an -(heteroalkyl)aryl radical where heteroalkyl and aryl are as disclosed herein and which are optionally substituted by one or more of the substituents described as suitable substituents for heteroalkyl and aryl respectively.

"Heteroaryl" or, alternatively, "heteroaromatic" refers to a 5- to 18-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indolizinyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as pyridinyl N-oxides.

"Heteroarylalkyl" refers to a moiety having a heteroaryl moiety, as described herein, connected to an alkyl moiety, as described herein, wherein the connection to the remainder of the molecule is through the alkyl group. Heteroaryl and alkyl are as disclosed herein and are optionally substituted by one or more of the substituents described as suitable substituents for heteroaryl and alkyl respectively.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range; e.g., "3 to 18 ring atoms" means that the heterocycloalkyl group may consist of 3 ring atoms, 4 ring atoms, etc., up to and including 18 ring atoms. In some embodiments, it is a $C_5$-$C_{10}$ heterocycloalkyl. In some embodiments, it is a $C_4$-$C_{10}$ heterocycloalkyl. In some embodiments, it is a $C_3$-$C_{10}$ heterocycloalkyl. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —$N(R^a)C(O)R^a$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Heterocycloalkyloxy" refers to a (heterocycloalkyl)-O— moiety, where the heterocycloalkyl moiety is attached via a carbon atom to oxygen, wherein the oxygen functions as a linker to attach the moiety to a compound. The heterocycloalkyl is as described herein and is optionally substituted by one or more substituents described herein as suitable for heterocycloalkyl.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

When the compounds described herein contain olefinic double bonds or other centers of geometric asymmetry, and unless specified otherwise, it is intended that the compounds include both E and Z geometric isomers.

"Moiety" refers to a specific segment or functional group of a molecule. Chemical moieties are often recognized chemical entities embedded in or appended to a molecule.

"Nitro" refers to the —$NO_2$ radical.

"Oxa" refers to the —O— radical.

"Oxo" refers to the =O radical.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

The compounds of the present invention may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

A "leaving group or atom" is any group or atom that will, under the reaction conditions, cleave from the starting material, thus promoting reaction at a specified site. Suitable examples of such groups unless otherwise specified are halogen atoms, mesyloxy, p-nitrobenzensulphonyloxy and tosyloxy groups.

"Protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, Protective Groups in Organic Synthesis, Third Edition, John Wiley & Sons, New York (1999). For example, a hydroxy protected form is where at least one of the hydroxy groups present in a compound is protected with a hydroxy protecting group. Likewise, amines and other reactive groups may similarly be protected.

"Solvate" refers to a compound (e.g., a compound selected from Formula I or a pharmaceutically acceptable salt thereof) in physical association with one or more molecules of a pharmaceutically acceptable solvent. It will be understood that "a compound of Formula I" encompass the compound of Formula I and solvates of the compound, as well as mixtures thereof.

"Substituted" means that the referenced group may be substituted with one or more additional group(s) individually and independently selected from acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and the protected derivatives thereof. Di-substituted amino groups encompass those which form a ring together with the nitrogen of the amino group, such as for instance, morpholino. The substituents themselves may be substituted, for example, a cycloakyl substituent may have a halide substituted at one or more ring carbons, and the like. The protecting groups that may form the protective derivatives of the above substituents are known to those of skill in the art and may be found in references such as Greene and Wuts, above.

"Sulfonyl" refers to the groups: —S(O₂)—H, —S(O₂)-(optionally substituted alkyl), —S(O₂)-(optionally substituted amino), —S(O₂)-(optionally substituted aryl), —S(O₂)-(optionally substituted heteroaryl), and —S(O₂)-(optionally substituted heterocycloalkyl).

"Sulfonamidyl" or "sulfonamido" refers to a —S(=O)₂—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S(=O)₂—NRR radical may be taken together with the nitrogen to which it is attached to form a 4-, 5-, 6-, or 7-membered ring. In some embodiments, it is a $C_1$-$C_{10}$ sulfonamido, wherein each R in sulfonamido contains 1 carbon, 2 carbons, 3 carbons, or 4 carbons total. A sulfonamido group is optionally substituted by one or more of the substituents described for alkyl, cycloalkyl, aryl, heteroaryl respectively "Sulfoxyl" refers to a —S(=O)₂OH radical.

"Sulfonate" refers to a —S(=O)₂—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl respectively.

Where substituent groups are specified by their conventional chemical formulae, written from left to right, they equally encompass the chemically identical substituents that would result from writing the structure from right to left, e.g., —CH₂O— is equivalent to —OCH₂—.

Compounds of the present invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

"Solvent," "organic solvent," and "inert solvent" each means a solvent inert under the conditions of the reaction being described in conjunction therewith including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like. Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can also be used.

When desired, the (R)- and (S)-isomers of the compounds of the present invention, if present, may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Pharmaceutically acceptable forms of the compounds recited herein include pharmaceutically acceptable salts, chelates, non-covalent complexes, prodrugs, and mixtures thereof. In certain embodiments, the compounds described herein are in the form of pharmaceutically acceptable salts. In addition, if the compound described herein is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, the present invention provides various compounds that are useful as antagonists for one or more lipid kinases and/or protein kinases.

In one aspect, the present invention provides a compound of Formula I:

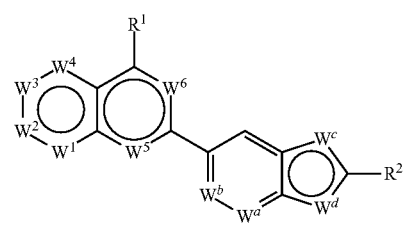

Formula I or its pharmaceutically acceptable salts thereof, wherein:
$W^1$ is N, $NR^3$, or $CR^3$; $W^2$ is N, $NR^4$, $CR^4$, or C=O; $W^3$ is N, $NR^5$ or $CR^5$; $W^4$ is N, wherein no more than two N atoms and no more than two C=O groups are adjacent;
$W^5$ is N;
$W^6$ is N or $CR^8$;

$W^a$ and $W^b$ are independently N or $CR^9$;

one of $W^c$ and $W^d$ is N, and the other is O, $NR^{10}$, or S;

$R^1$ and $R^2$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;

$R^3$ and $R^4$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; or $R^3$ and $R^4$ taken together form a cyclic moiety;

$R^5$, $R^6$, $R^7$ and $R^8$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;

$R^9$ is alkyl or halo; and $R^{10}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety.

In some embodiments, the compound of Formula I exists as a tautomer, and such tautomers are contemplated by the present invention.

In some embodiments, $R^1$ is hydrogen. In other embodiments, $R^1$ is alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R", wherein R' and R" are taken together with nitrogen to form a cyclic moiety.

In some embodiments, $R^2$ is hydrogen. In other embodiments, $R^2$ is, for example, unsubstituted or substituted alkyl (including but not limited to $CH_3$, —$CH_2CH_3$, n-propyl, isopropyl, n-butyl, tert-butyl, sec-butyl, pentyl, hexyl, and heptyl). In other embodiments, $R^2$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^2$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, —$CH_2CH_3$, n-propyl, isopropyl, n-butyl, sec-butyl, and pentyl). In some other embodiments, $R^2$ is unsubstituted or substituted heteroaryl, including but not limited to monocyclic and bicyclic heteroaryl. Monocyclic heteroaryl $R^2$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^2$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl. The present invention also provides compounds wherein $R^2$ is unsubstituted or substituted heteroarylalkyl, including but not limited to monocyclic and bicyclic heteroaryl as described above, that are linked to alkyl, which in turn includes but is not limited to $CH_3$, —$CH_2CH_3$, n-propyl, isopropyl, n-butyl, sec-butyl, and pentyl. In some embodiments, $R^2$ is unsubstituted or substituted cycloalkyl (including but not limited to cyclopropyl, cyclobutyl, and cyclopentyl) or unsubstituted or substituted heteroalkyl (non-limiting examples include ethoxymethyl, methoxymethyl, and diethylaminomethyl). In some further embodiments, $R^2$ is unsubstituted or substituted heterocycloalkyl which includes but is not limited to pyrrolidinyl, tetrahydrofuranyl, piperidinyl, tetrahydropyranyl, thiazolidinyl, imidazolidinyl, morpholinyl, and piperazinyl. In yet other embodiments of the compounds of Formula I, $R^2$ is unsubstituted or substituted alkoxy including but not limited to $C_1$-$C_4$alkoxy such as methoxy, ethoxy, propoxy or butoxy. $R^2$ can also be unsubstituted or substituted heterocycloalkyloxy, including but not limited to 4-NH piperidin-1-yl-oxy, 4-methyl piperidin-1-yl-oxy, 4-ethyl piperidin-1-yl-oxy, 4-isopropyl-piperidin-1-yl-oxy, and pyrrolidin-3-yl-oxy. In other embodiments, $R^2$ is unsubstituted or substituted amino, wherein the substituted amino includes but is not limited to dimethylamino, diethylamino, di-isopropyl amino, N-methyl N-ethyl amino, and dibutylamino. In some embodiments, $R^2$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted amido, or unsubstituted or substituted sulfonamido. In other embodiments, $R^2$ is halo, which is —I, —F, —Cl, or —Br. In some embodiments, $R^2$ is selected from the group consisting of cyano, hydroxy, nitro, phosphate, urea, and carbonate. Also contemplated are $R^2$ being —$CH_3$, —$CH_2CH_3$, n-propyl, isopropyl, n-butyl, tert-butyl, sec-butyl, pentyl, hexyl, heptyl, —$OCH_3$, —$OCH_2CH_3$, or —$CF_3$.

In some embodiments of the compound of Formula I, $W^1$ is $CR^3$. $R^3$ can be, for example, hydrogen, unsubstituted or substituted alkyl (including but not limited to $CH_3$, —$CH_2CH_3$, n-propyl, isopropyl, n-butyl, tert-butyl, sec-butyl, pentyl, hexyl, and heptyl). In other embodiments, $R^3$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^3$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, —$CH_2CH_3$, n-propyl, isopropyl, n-butyl, sec-butyl, and pentyl). In some other embodiments, $R^3$ is unsubstituted or substituted heteroaryl, including but not limited to monocyclic and bicyclic heteroaryl. Monocyclic heteroaryl $R^3$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^3$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl. The present invention also provides compounds of Formula I wherein R³ is unsubstituted or substituted heteroarylalkyl, including but not limited to monocyclic and bicyclic heteroaryl as described above, that are linked to alkyl, which in turn includes but is not limited to CH₃, —CH₂CH₃, n-propyl, isopropyl, n-butyl, sec-butyl, and pentyl. In some embodiments, R³ is unsubstituted or substituted cycloalkyl (including but not limited to cyclopropyl, cyclobutyl, and cyclopentyl) or unsubstituted or substituted heteroalkyl (non-limiting examples include ethoxymethyl, methoxymethyl, and diethylaminomethyl). In some further embodiments, R³ is unsubstituted or substituted heterocycloalkyl which includes but is not limited to pyrrolidinyl, tetrahydrofuranyl, piperidinyl, tetrahydropyranyl, thiazolidinyl, imidazolidinyl, morpholinyl, and piperazinyl. In yet other embodiments of the compounds of Formula I, R³ is unsubstituted or substituted alkoxy including but not limited to C₁-C₄alkoxy such as methoxy, ethoxy, propoxy or butoxy. R³ can also be unsubstituted or substituted heterocycloalkyloxy, including but not limited to 4-NH piperidin-1-yl-oxy, 4-methyl piperidin-1-yl-oxy, 4-ethyl piperidin-1-yl-oxy, 4-isopropyl-piperidin-1-yl-oxy, and pyrrolidin-3-yl-oxy. In other embodiments, R³ is unsubstituted or substituted amino, wherein the substituted amino includes but is not limited to dimethylamino, diethylamino, di-isopropyl amino, N-methyl N-ethyl amino, and dibutylamino. In some embodiments, R³ is unsubstituted or substituted acyl, unsubstituted or substituted acyloxy, unsubstituted or substituted C₁-C₄acyloxy, unsubstituted or substituted alkoxycarbonyl, unsubstituted or substituted amido, or unsubstituted or substituted sulfonamido. In other embodiments, R³ is halo, which is —I, —F, —Cl, or —Br. In some embodiments, R³ is selected from the group consisting of cyano, hydroxy, nitro, phosphate, urea, and carbonate. Also contemplated are R³ being —CH₃, —CH₂CH₃, n-propyl, isopropyl, n-butyl, tert-butyl, sec-butyl, pentyl, hexyl, heptyl, —OCH₃, —OCH₂CH₃, or —CF₃.

R³ of the compounds of Formula I, can also be NR'R" wherein R' and R" are taken together with the nitrogen to form a cyclic moiety having from 3 to 8 ring atoms. The cyclic moiety so formed may further include one or more heteroatoms which are selected from the group consisting of S, O, and N. The cyclic moiety so formed is unsubstituted or substituted, including but not limited to morpholinyl, azetidinyl, pyrrolidinyl, piperidinyl, piperazinyl, isothiazolidinyl 1,2, dioxide, and thiomorpholinyl. Further non-limiting exemplary cyclic moieties are the following:

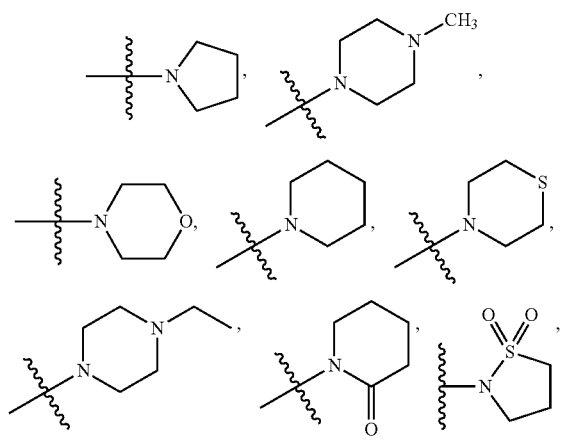

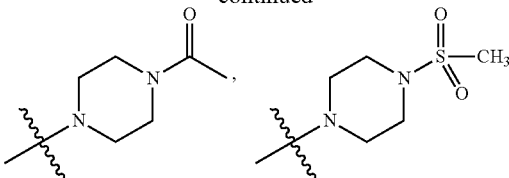

The invention also provides compounds of Formula I, wherein when R³ is a member of the group consisting of alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, alkoxycarbonyl, and NR'R" (wherein R' and R" are taken together with nitrogen to form a cyclic moiety), then R³ is optionally substituted with one or more of the following substituents: alkyl, alkenyl, alkynyl, cycloalkyl, heteroalkyl, heterocycloalkyl, heterocycloalkyloxy, aryl, arylalkyl, heteroaryl, heteroarylalkyl, acyl, heterocycloalkyloxy, alkoxy, amido, amino, sulfonamido, acyloxy, alkoxycarbonyl, halo, cyano, hydroxy, nitro, phosphate, urea, carbonate, or NR'R" wherein R' and R" are taken together with nitrogen to form a cyclic moiety. Each of the above substituents may be further substituted with one or more substituents chosen from the group consisting of alkyl, alkoxy, amido, amino, sulfonamido, acyloxy, alkoxycarbonyl, halo, cyano, hydroxy, nitro, oxo, phosphate, urea, and carbonate.

For example, the invention provides compounds wherein when R³ is alkyl, the alkyl is substituted with NR'R" wherein R' and R" are taken together with the nitrogen to form a cyclic moiety. The cyclic moiety so formed can be unsubstituted or substituted. Non-limiting exemplary cyclic moieties includes but are not limited to morpholinyl, azetidinyl, pyrrolidinyl, piperidinyl, piperazinyl, and thiomorpholinyl. In other examples of the compounds of Formula I, when R³ is alkyl, the alkyl is substituted with heterocycloalkyl, which includes oxetanyl, azetidinyl, tetrahydrofuranyl, pyrrolyl, tetrahydropyranyl, piperidinyl, morpholinyl, and piperazinyl. All of the above listed heterocycloaklyl substituents can be unsubstituted or substituted.

In yet other examples of the compounds of Formula I, when R³ is alkyl, the alkyl is substituted with a 5, 6, 7, 8, 9, or 10 membered monocyclic or bicyclic heteroaryl, which is unsubstituted or substituted. The monocyclic heteroaryl includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. The bicyclic heteroaryl includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl.

In other embodiments of the compound of Formula I, R³ is —NHR³', —N(CH₃)R³', —N(CH₂CH₃)R³', —N(CH(CH₃)₂) R³', or —OR³', wherein R³' is unsubstituted or substituted heterocycloalkyl(nonlimiting examples thereof include 4-NH piperidin-1-yl, 4-methyl piperidin-1-yl, 4-ethyl piperidin-1-yl, 4-isopropyl-piperidin-1-yl, and pyrrolidin-3-yl), unsubstituted or substituted monocyclic aryl, or unsubstituted or substituted monocyclic heteroaryl (including but not limited to pyrrolyl, thienyl, furyl, pyridinyl, pyranyl, pyrimidinyl, pyrazinyl, pyridazinyl, imidazolyl, thiazolyl, pyrazolyl, and oxazolyl). In one example, R³ is —O-aryl, i.e.

phenoxy. In another example, $R^3$ is —O-(4-methyl)piperidin-1-yl or —O-(4-isopropyl)piperidin-1-yl.
In some embodiments of the compound of Formula I, $R^3$ is one of the following moieties:
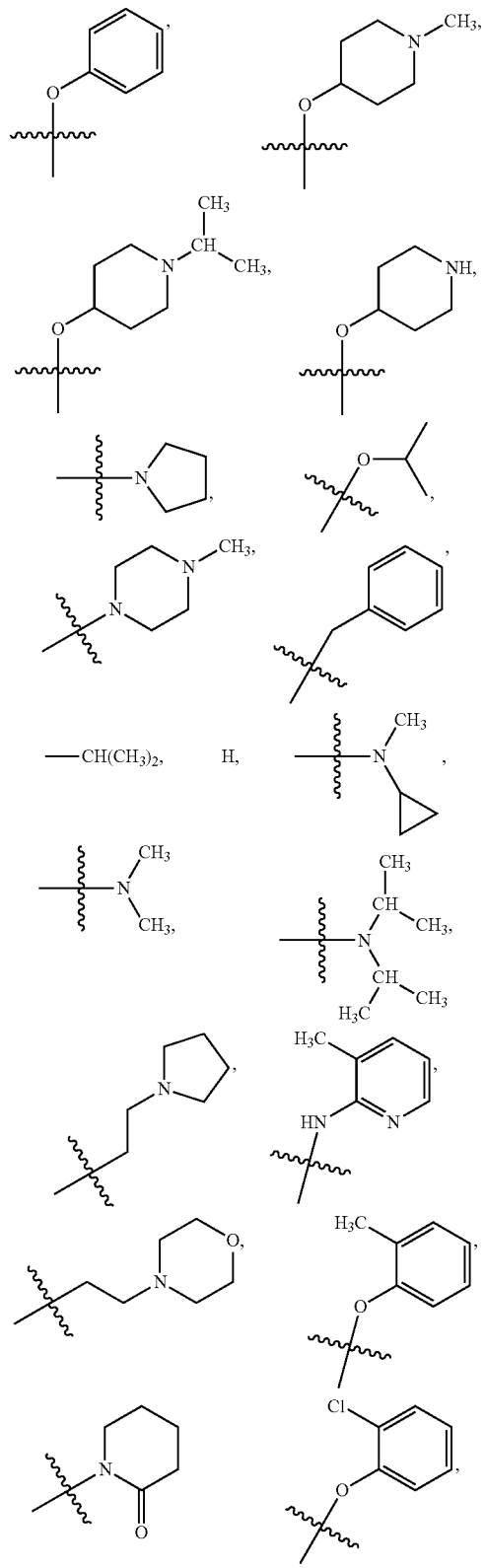
-continued
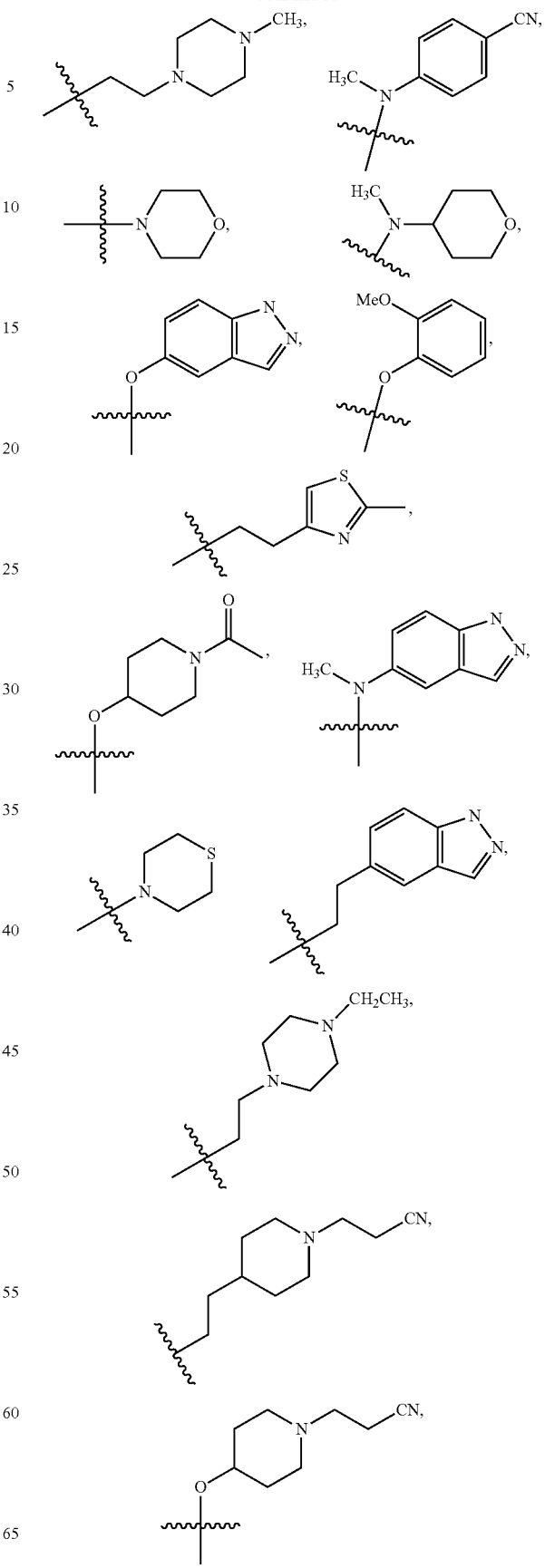

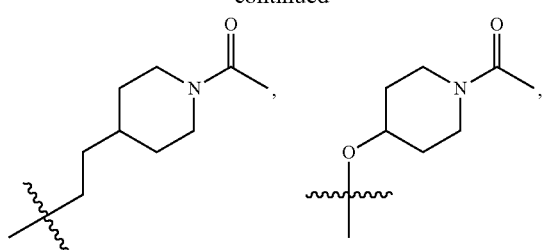
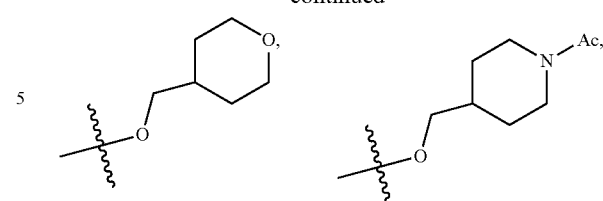
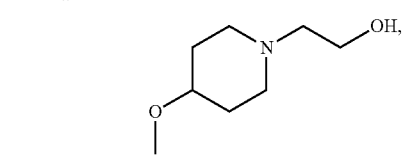
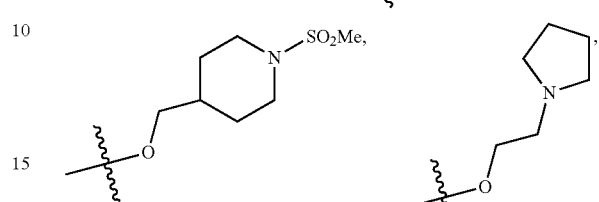
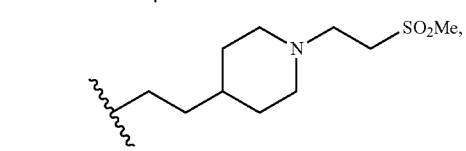
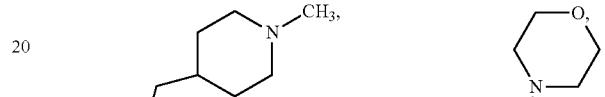
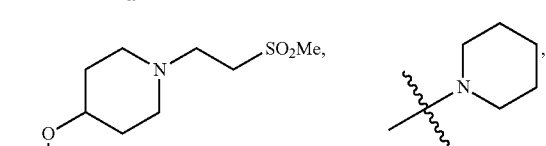
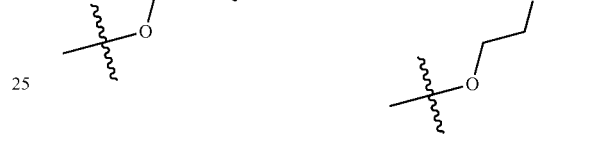
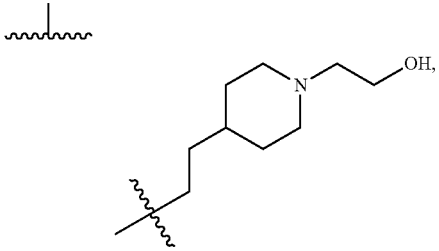
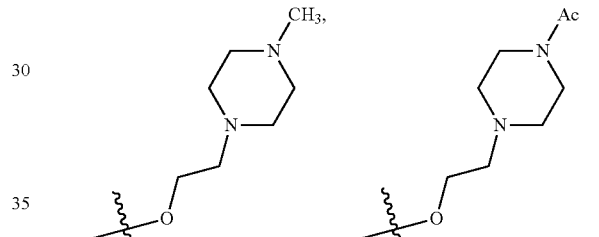
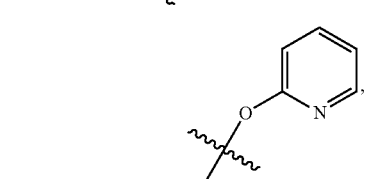
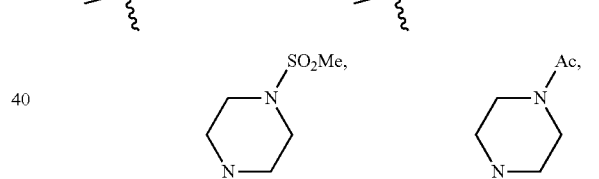
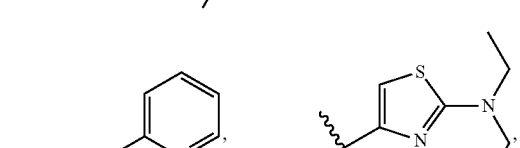
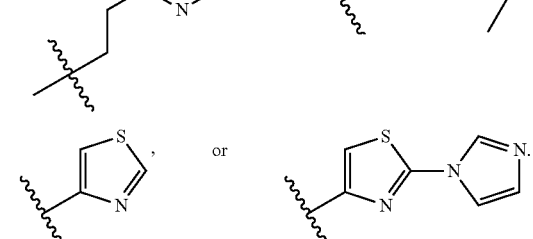
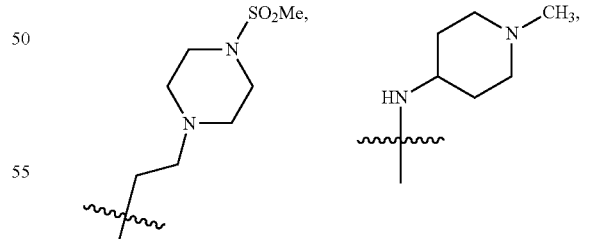
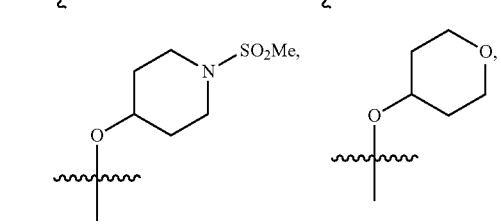
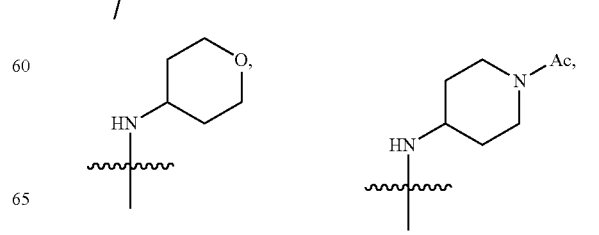

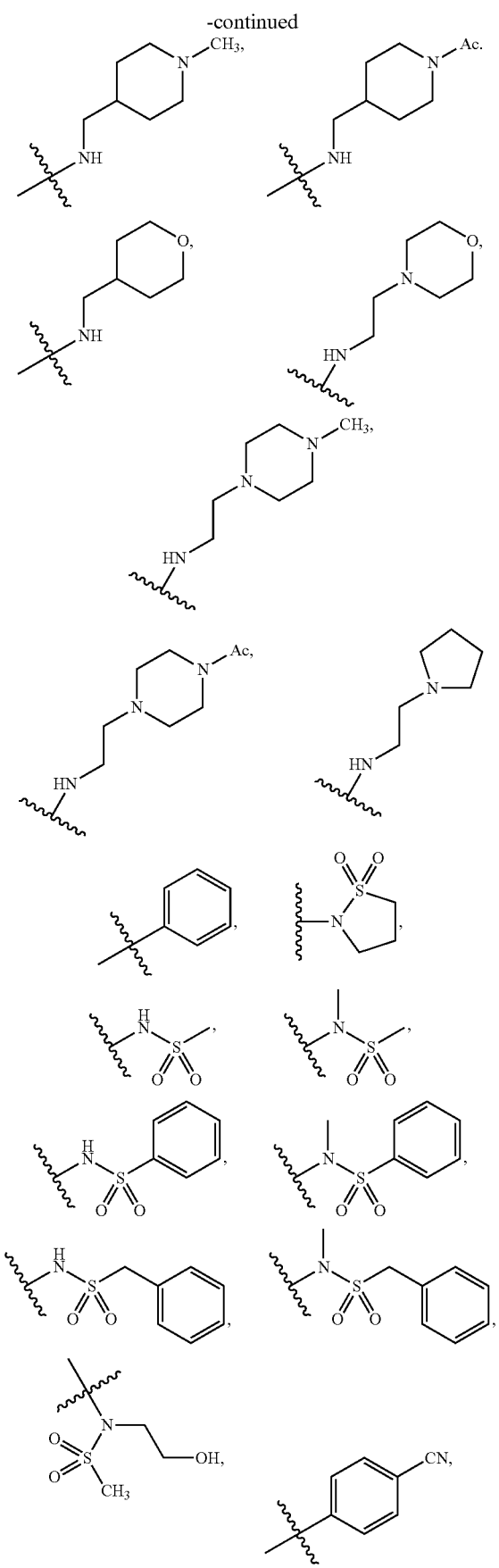

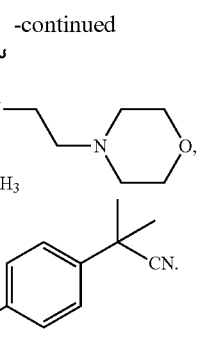

In some embodiments of the compound of Formula I, $W^1$ is $NR^3$, wherein $R^3$ is hydrogen, unsubstituted or substituted $C_1$-$C_{10}$alkyl (which includes but is not limited to —$CH_3$, —$CH_2CH_3$, n-propyl, isopropyl, n-butyl, tert-butyl, sec-butyl, pentyl, hexyl, and heptyl), or unsubstituted or substituted $C_3$-$C_7$cycloalkyl (which includes but is not limited to cyclopropyl, cyclobutyl, cyclopentyl, and cyclohexyl). In other embodiments of the compound of Formula I, $R^3$ is unsubstituted or substituted heterocycloalkyl (which includes but is not limited to oxetanyl, tetrahydrofuranyl, pyrrolidinyl, tetrahydropyranyl, piperidinyl, and piperazinyl), or unsubstituted or substituted $C_2$-$C_{10}$heteroalkyl (which includes but is not limited to methoxyethoxy, methoxymethyl, and diethylaminoethyl). Alternatively, $R^3$ is unsubstituted or substituted monocyclic heteroaryl (which includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl) or unsubstituted or substituted monocyclic aryl.

In still other embodiments, $W^1$ is C=O.

In some embodiments of the compound of Formula I, $W^2$ is $CR^4$. $R^4$ can be, for example, hydrogen, or unsubstituted or substituted alkyl (including but not limited to $CH_3$, —$CH_2CH_3$, n-propyl, isopropyl, n-butyl, tert-butyl, sec-butyl, pentyl, hexyl, and heptyl). In other embodiments, $R^4$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^4$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, —$CH_2CH_3$, n-propyl, isopropyl, n-butyl, sec-butyl, and pentyl). In some other embodiments, $R^4$ is unsubstituted or substituted heteroaryl, including but not limited to monocyclic and bicyclic heteroaryl. Monocyclic heteroaryl $R^4$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^4$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl.

The present invention also provides compounds of Formula I wherein $R^4$ is unsubstituted or substituted heteroarylalkyl, including but not limited to monocyclic and bicyclic heteroaryl as described above, that are linked to alkyl, which in turn includes but is not limited to CH₃, —CH₂CH₃, n-propyl, isopropyl, n-butyl, sec-butyl, and pentyl. In some embodiments, R⁴ is unsubstituted or substituted cycloalkyl (including but not limited to cyclopropyl, cyclobutyl, and cyclopentyl) or unsubstituted or substituted heteroalkyl (non-limiting examples include ethoxymethyl, methoxymethyl, and diethylaminomethyl). In some further embodiments, R⁴ is unsubstituted or substituted heterocycloalkyl which includes but is not limited to pyrrolidinyl, tetrahydrofuranyl, piperidinyl, tetrahydropyranyl, thiazolidinyl, imidazolidinyl, morpholinyl, and piperazinyl. In yet other embodiments of the compounds of Formula I, R⁴ is unsubstituted or substituted alkoxy including but not limited to $C_1$-$C_4$alkoxy such as methoxy, ethoxy, propoxy or butoxy. R⁴ can also be unsubstituted or substituted heterocycloalkyloxy, including but not limited to 4-NH piperidin-1-yl-oxy, 4-methyl piperidin-1-yl-oxy, 4-ethyl piperidin-1-yl-oxy, 4-isopropyl-piperidin-1-yl-oxy, and pyrrolidin-3-yl-oxy. In other embodiments, R⁴ is unsubstituted or substituted amino, wherein the substituted amino includes but is not limited to dimethylamino, diethylamino, di-isopropyl amino, N-methyl N-ethyl amino, and dibutylamino. In some embodiments, R⁴ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted amido, or unsubstituted or substituted sulfonamido. In some embodiments, R⁴ is halo, which is —I, —F, —Cl, or —Br. In some embodiments, R⁴ is selected from the group consisting of cyano, hydroxy, nitro, phosphate, urea, or carbonate. Also contemplated are R⁴ being —CH₃, —CH₂CH₃, n-propyl, isopropyl, n-butyl, tert-butyl, sec-butyl, pentyl, hexyl, heptyl, —OCH₃, —OCH₂CH₃, or —CF₃.

R⁴ of the compounds of Formula I, can also be NR'R" wherein R' and R" are taken together with the nitrogen to form a cyclic moiety having from 3 to 8 ring atoms. The cyclic moiety so formed may further include one or more heteroatoms which are selected from the group consisting of S, O, and N. The cyclic moiety so formed is unsubstituted or substituted, including but not limited to morpholinyl, azetidinyl, pyrrolidinyl, piperidinyl, piperazinyl, isothiazolidinyl 1,2, dioxide, and thiomorpholinyl. Further non-limiting exemplary cyclic moieties are the following:

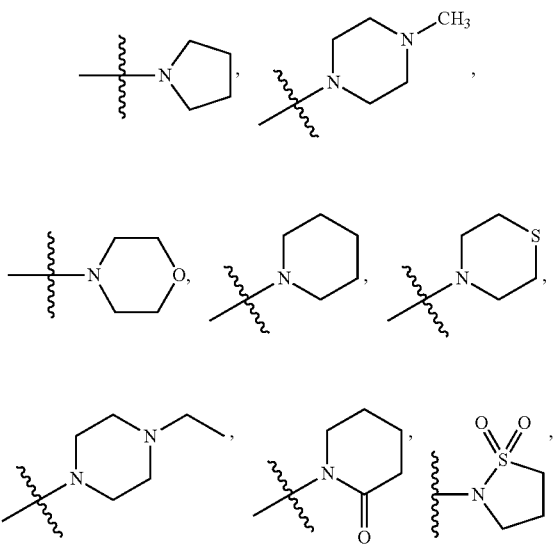

-continued

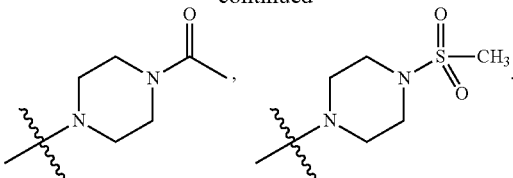

The invention also provides compounds of Formula I, wherein when R⁴ is a member of the group consisting of alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, alkoxycarbonyl, and NR'R" (wherein R' and R" are taken together with nitrogen to form a cyclic moiety), then R⁴ is optionally substituted with one or more of the following substituents: alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, alkoxycarbonyl, halo, cyano, hydroxy, nitro, phosphate, urea, carbonate, or NR'R" wherein R' and R" are taken together with nitrogen to form a cyclic moiety. Each of the above substituents may be further substituted with one or more substituents chosen from the group consisting of alkyl, alkoxy, amido, amino, sulfonamido, acyloxy, alkoxycarbonyl, halo, cyano, hydroxy, nitro, oxo, phosphate, urea, and carbonate.

For example, the invention provides compounds wherein when R⁴ is alkyl, the alkyl is substituted with NR'R" wherein R' and R" are taken together with the nitrogen to form a cyclic moiety. The cyclic moiety so formed can be unsubstituted or substituted. Non-limiting exemplary cyclic moieties includes but are not limited to morpholinyl, azetidinyl, pyrrolidinyl, piperidinyl, piperazinyl, isothiazolidinyl 1,2, dioxide, and thiomorpholinyl. In other examples of the compounds of Formula I, when R⁴ is alkyl, the alkyl is substituted with heterocycloalkyl, which includes oxetanyl, azetidinyl, tetrahydrofuranyl, pyrrolyl, tetrahydropyranyl, piperidinyl, morpholinyl, and piperazinyl. All of the above listed heterocycloaklyl substituents can be unsubstituted or substituted.

In yet other examples of the compounds of Formula I, when R⁴ is alkyl, the alkyl is substituted with a 5, 6, 7, 8, 9, or 10 membered monocyclic or bicyclic heteroaryl, which is unsubstituted or substituted. The monocyclic heteroaryl includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. The bicyclic heteroaryl includes but is not limited benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl.

In some embodiments of the compound of Formula I, W² is NR⁴, wherein R⁴ is hydrogen, unsubstituted or substituted $C_1$-$C_{10}$alkyl (which includes but is not limited to —CH₃, —CH₂CH₃, n-propyl, isopropyl, n-butyl, tert-butyl, sec-butyl, pentyl, hexyl, and heptyl), or unsubstituted or substituted $C_3$-$C_7$cycloalkyl (which includes but is not limited to cyclopropyl, cyclobutyl, cyclopentyl, and cyclohexyl). In other embodiments of the compound of Formula I, R⁴ is unsubstituted or substituted heterocycloalkyl (which includes but is not limited to oxetanyl, tetrahydrofuranyl, pyrrolidinyl, tetrahydropyranyl, piperidinyl, and piperazinyl), or unsubstituted or substituted $C_2$-$C_{10}$heteroalkyl (which includes but is not limited to methoxyethoxy, methoxymethyl, and diethylaminoethyl). Alternatively, $R^4$ is unsubstituted or substituted monocyclic heteroaryl (which includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl) or unsubstituted or substituted monocyclic aryl.

In some embodiments $R^3$ and $R^4$ taken together form a cyclic moiety. Such a moiety may have, for example, from 3 to 8 ring atoms. The cyclic moiety so formed may further include one or more heteroatoms which are selected from the group consisting of S, O, and N. The cyclic moiety so formed is unsubstituted or substituted. In some embodiments, the substituent is $C_1$-$C_{10}$alkyl (which includes but is not limited to —$CH_3$, —$CH_2CH_3$, n-propyl, isopropyl, n-butyl, tert-butyl, sec-butyl, pentyl, hexyl, and heptyl), or $C_3$-$C_7$cycloalkyl (which includes but is not limited to cyclopropyl, cyclobutyl, cyclopentyl, and cyclohexyl); heterocycloalkyl (which includes but is not limited to oxetanyl, tetrahydrofuranyl, pyrrolidinyl, tetrahydropyranyl, piperidinyl, and piperazinyl), $C_2$-$C_{10}$heteroalkyl (which includes but is not limited to methoxyethoxy, methoxymethyl, and diethylaminoethyl); monocyclic heteroaryl (which includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl) or unsubstituted or substituted monocyclic aryl. The cyclic moiety may have one or more substituents, which may be the same or different.

In some embodiments, the cyclic moiety formed by $R^3$ and $R^4$ is substituted with at least one of the following substituents:

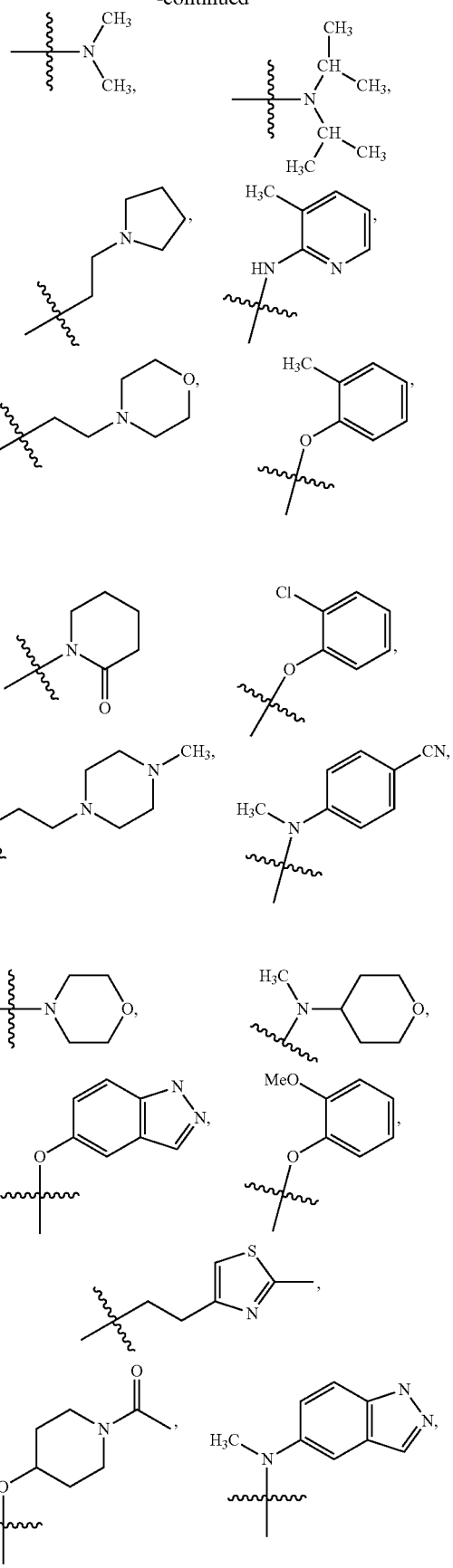

-continued

-continued

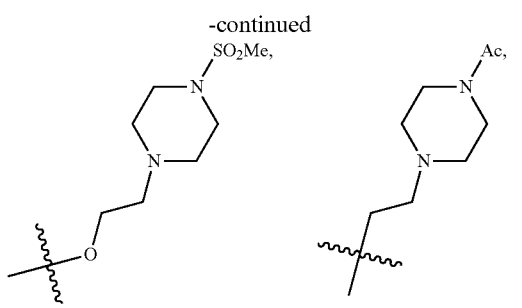

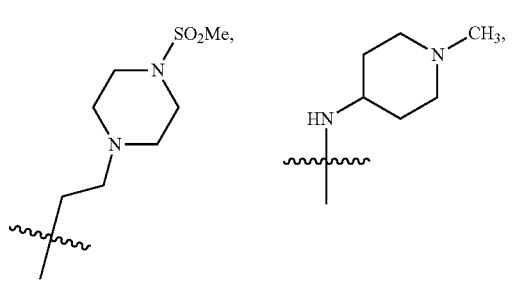

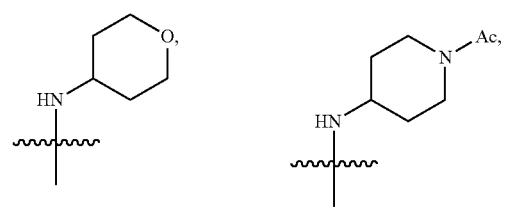

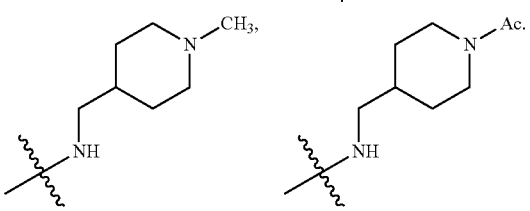

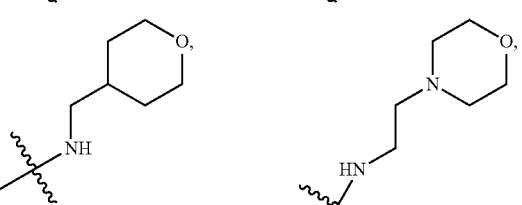

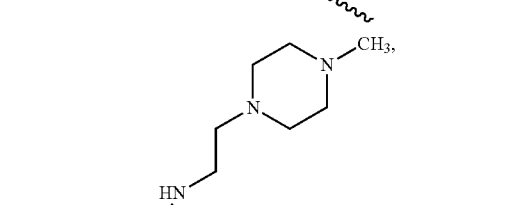

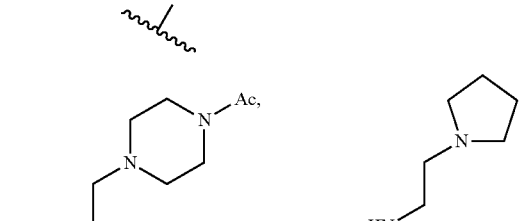

-continued

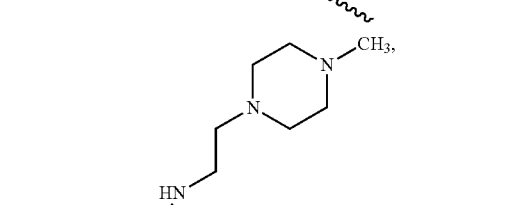

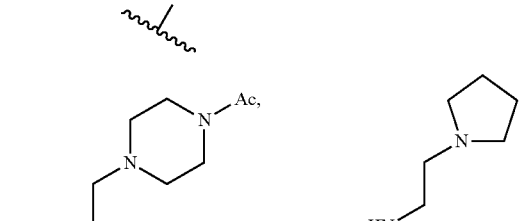

In some embodiments of the compound of Formula I, $W^3$ is $CR^5$. $R^5$ can be, for example, hydrogen, or unsubstituted or substituted alkyl (including but not limited to $CH_3$, —$CH_2CH_3$, n-propyl, isopropyl, n-butyl, tert-butyl, sec-butyl, pentyl, hexyl, and heptyl). In one embodiment, $R^5$ is H. In other embodiments, $R^5$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^5$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, —$CH_2CH_3$, n-propyl, isopropyl, n-butyl, sec-butyl, and pentyl). In some other embodiments, $R^5$ is unsubstituted or substituted heteroaryl, including but not limited to monocyclic and bicyclic heteroaryl. Monocyclic heteroaryl $R^5$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^5$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl.

In some embodiments of the compound of Formula I, $W^3$ is N or $NR^5$, wherein $R^5$ is hydrogen, unsubstituted or substituted $C_1$-$C_{10}$alkyl (which includes but is not limited to —$CH_3$, —$CH_2CH_3$, n-propyl, isopropyl, n-butyl, tert-butyl, sec-butyl, pentyl, hexyl, and heptyl), or unsubstituted or substituted $C_3$-$C_7$cycloalkyl (which includes but is not limited to cyclopropyl, cyclobutyl, cyclopentyl, and cyclohexyl). In other embodiments of the compound of Formula I, $R^5$ is unsubstituted or substituted heterocycloalkyl (which includes but is not limited to oxetanyl, tetrahydrofuranyl, pyrrolidinyl, tetrahydropyranyl, piperidinyl, and piperazinyl), or unsubstituted or substituted $C_2$-$C_{10}$heteroalkyl (which includes but is not limited to methoxyethoxy, methoxymethyl, and diethylaminoethyl). Alternatively, $R^5$ is unsubstituted or substituted monocyclic heteroaryl (which includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl) or unsubstituted or substituted monocyclic aryl.

In some embodiments of the compound of Formula I, $W^4$ is N or $NR^6$, wherein $R^6$ is hydrogen, unsubstituted or substituted $C_1$-$C_{10}$alkyl (which includes but is not limited to —$CH_3$, —$CH_2CH_3$, n-propyl, isopropyl, n-butyl, tert-butyl, sec-butyl, pentyl, hexyl, and heptyl), or unsubstituted or substituted $C_3$-$C_7$cycloalkyl (which includes but is not limited to cyclopropyl, cyclobutyl, cyclopentyl, and cyclohexyl). In other embodiments of the compound of Formula I, $R^6$ is unsubstituted or substituted heterocycloalkyl (which includes but is not limited to oxetanyl, tetrahydrofuranyl, pyrrolidinyl, tetrahydropyranyl, piperidinyl, and piperazinyl), or unsubstituted or substituted $C_2$-$C_{10}$heteroalkyl (which includes but is not limited to methoxyethoxy, methoxymethyl, and diethylaminoethyl). Alternatively, $R^6$ is unsubstituted or substituted monocyclic heteroaryl (which includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl) or unsubstituted or substituted monocyclic aryl.

In some embodiments of the compound of Formula I, $W^6$ is N. In other embodiments of the compound of Formula I, $W^6$ is $CR^8$. $R^8$ can be, for example, hydrogen, or unsubstituted or substituted alkyl (including but not limited to $CH_3$, —$CH_2CH_3$, n-propyl, isopropyl, n-butyl, tert-butyl, sec-butyl, pentyl, hexyl, and heptyl). In one embodiment, $R^8$ is H. In other embodiments, $R^8$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^8$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, —$CH_2CH_3$, n-propyl, isopropyl, n-butyl, sec-butyl, and pentyl). In some other embodiments, $R^8$ is unsubstituted or substituted heteroaryl, including but not limited to monocyclic and bicyclic heteroaryl. Monocyclic heteroaryl $R^8$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^8$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl.

In some embodiments, the compound of Formula I has the formula:

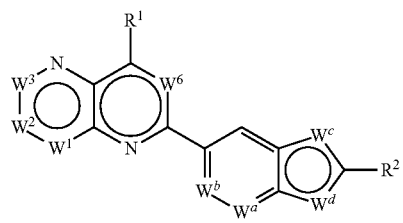

In other embodiments, the compound of Formula I is:

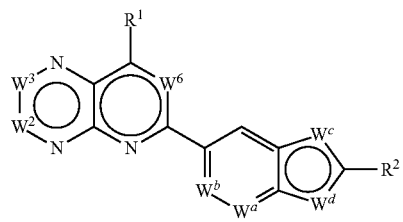

For example, the compound of Formula I is:

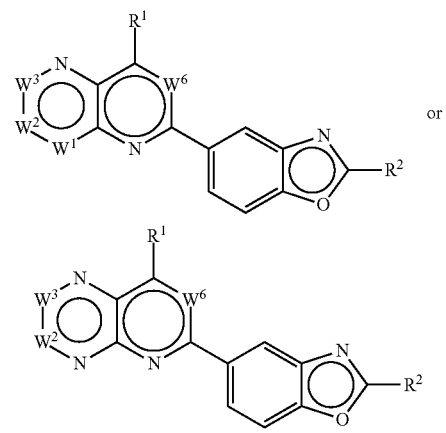

In some embodiments, the compound of Formula I is:

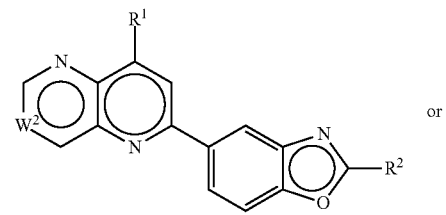

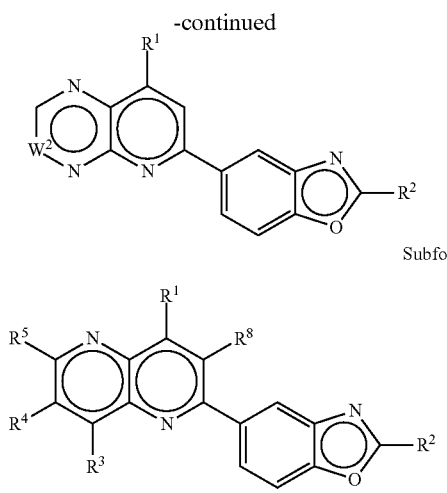

In another aspect, the invention provides compounds of Subformula Ia. In one embodiment, $R^1$, $R^3$, $R^4$, $R^5$, and $R^8$ are hydrogen. In another embodiment, $R^1$, $R^3$, $R^5$, and $R^8$ are hydrogen and $R^4$ is alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety. $R^4$ can be, for example, hydrogen, unsubstituted or substituted alkyl (including but not limited to $CH_3$, $-CH_2CH_3$, n-propyl, isopropyl, n-butyl, tert-butyl, sec-butyl, pentyl, hexyl, and heptyl). In other embodiments, $R^4$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^4$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, $-CH_2CH_3$, n-propyl, isopropyl, n-butyl, sec-butyl, and pentyl). In some other embodiments, $R^4$ is unsubstituted or substituted heteroaryl, including but not limited to monocyclic and bicyclic heteroaryl. Monocyclic heteroaryl $R^4$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^4$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl. The present invention also provides compounds of Subformula Ia wherein $R^4$ is unsubstituted or substituted heteroarylalkyl, including but not limited to monocyclic and bicyclic heteroaryl as described above, that are linked to alkyl, which in turn includes but is not limited to $CH_3$, $-CH_2CH_3$, n-propyl, isopropyl, n-butyl, sec-butyl, and pentyl. In some embodiments, $R^4$ is unsubstituted or substituted cycloalkyl (including but not limited to cyclopropyl, cyclobutyl, and cyclopentyl) or unsubstituted or substituted heteroalkyl (non-limiting examples include ethoxymethyl, methoxymethyl, and diethylaminomethyl). In some further embodiments, $R^4$ is unsubstituted or substituted heterocycloalkyl which includes but is not limited to pyrrolidinyl, tetrahydrofuranyl, piperidinyl, tetrahydropyranyl, thiazolidinyl, imidazolidinyl, morpholinyl, and piperazinyl. In yet other embodiments of the compounds of Formula I, $R^4$ is unsubstituted or substituted alkoxy including but not limited to $C_1$-$C_4$alkoxy such as methoxy, ethoxy, propoxy or butoxy. $R^4$ can also be unsubstituted or substituted heterocycloalkyloxy, including but not limited to 4-NH piperidin-1-yl-oxy, 4-methyl piperidin-1-yl-oxy, 4-ethyl piperidin-1-yl-oxy, 4-isopropyl-piperidin-1-yl-oxy, and pyrrolidin-3-yl-oxy. In other embodiments, $R^4$ is unsubstituted or substituted amino, wherein the substituted amino includes but is not limited to dimethylamino, diethylamino, di-isopropyl amino, N-methyl N-ethyl amino, and dibutylamino. In some embodiments, $R^4$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted amido, or unsubstituted or substituted sulfonamido. In other embodiments, $R^4$ is halo, which is —I, —F, —Cl, or —Br. In some embodiments, $R^4$ is selected from the group consisting of cyano, hydroxy, nitro, phosphate, urea, and carbonate. Also contemplated are $R^4$ being —$CH_3$, —$CH_2CH_3$, n-propyl, isopropyl, n-butyl, tert-butyl, sec-butyl, pentyl, hexyl, heptyl, —$OCH_3$, —$OCH_2CH_3$, or —$CF_3$. In some embodiments $R^4$ can also be NR'R" wherein R' and R" are taken together with the nitrogen to form a cyclic moiety having from 3 to 8 ring atoms. The cyclic moiety so formed may further include one or more heteroatoms which are selected from the group consisting of S, O, and N. The cyclic moiety so formed is unsubstituted or substituted, including but not limited to morpholinyl, azetidinyl, pyrrolidinyl, piperidinyl, piperazinyl, isothiazolidinyl 1,2, dioxide, and thiomorpholinyl. Further non-limiting exemplary cyclic moieties are the following:

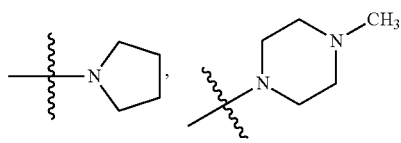

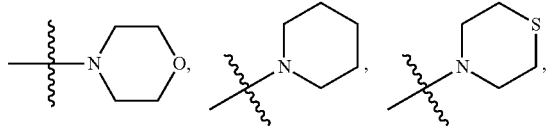

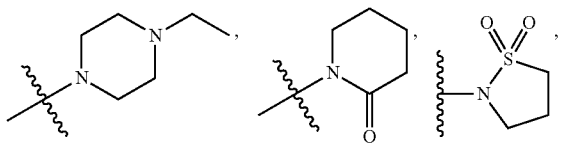

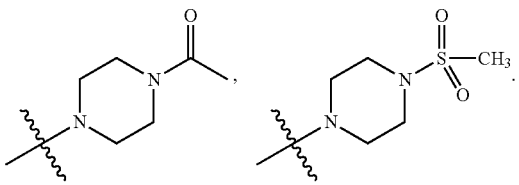

Subformula Ib

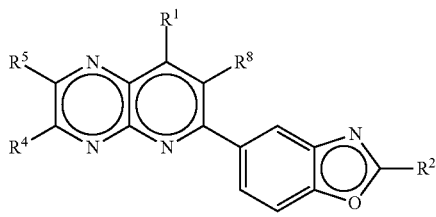

In another aspect, the invention provides compounds of Subformula Ib. In one embodiment, $R^1$, $R^4$, $R^5$ and $R^8$ are hydrogen. In another embodiment, $R^1$, $R^5$, and $R^8$ are hydrogen and $R^4$ is alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety. $R^4$ can be, for example, hydrogen, unsubstituted or substituted alkyl (including but not limited to $CH_3$, $-CH_2CH_3$, n-propyl, isopropyl, n-butyl, tert-butyl, sec-butyl, pentyl, hexyl, and heptyl). In other embodiments, $R^4$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^4$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, $-CH_2CH_3$, n-propyl, isopropyl, n-butyl, sec-butyl, and pentyl). In some other embodiments, $R^4$ is unsubstituted or substituted heteroaryl, including but not limited to monocyclic and bicyclic heteroaryl. Monocyclic heteroaryl $R^4$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^4$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl. The present invention also provides compounds of Formula I wherein $R^4$ is unsubstituted or substituted heteroarylalkyl, including but not limited to monocyclic and bicyclic heteroaryl as described above, that are linked to alkyl, which in turn includes but is not limited to $CH_3$, $-CH_2CH_3$, n-propyl, isopropyl, n-butyl, sec-butyl, and pentyl. In some embodiments, $R^4$ is unsubstituted or substituted cycloalkyl (including but not limited to cyclopropyl, cyclobutyl, and cyclopentyl) or unsubstituted or substituted heteroalkyl (non-limiting examples include ethoxymethyl, methoxymethyl, and diethylaminomethyl). In some further embodiments, $R^4$ is unsubstituted or substituted heterocycloalkyl which includes but is not limited to pyrrolidinyl, tetrahydrofuranyl, piperidinyl, tetrahydropyranyl, thiazolidinyl, imidazolidinyl, morpholinyl, and piperazinyl. In yet other embodiments of the compounds of Formula I, $R^4$ is unsubstituted or substituted alkoxy including but not limited to $C_1$-$C_4$alkoxy such as methoxy, ethoxy, propoxy or butoxy. $R^3$ can also be unsubstituted or substituted heterocycloalkyloxy, including but not limited to 4-NH piperidin-1-yl-oxy, 4-methyl piperidin-1-yl-oxy, 4-ethyl piperidin-1-yl-oxy, 4-isopropyl-piperidin-1-yl-oxy, and pyrrolidin-3-yl-oxy. In other embodiments, $R^4$ is unsubstituted or substituted amino, wherein the substituted amino includes but is not limited to dimethylamino, diethylamino, di-isopropyl amino, N-methyl N-ethyl amino, and dibutylamino. In some embodiments, $R^4$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted amido, or unsubstituted or substituted sulfonamido. In other embodiments, $R^4$ is halo, which is —I, —F, —Cl, or —Br. In some embodiments, $R^4$ is selected from the group consisting of cyano, hydroxy, nitro, phosphate, urea, and carbonate. Also contemplated are $R^4$ being —$CH_3$, —$CH_2CH_3$, n-propyl, isopropyl, n-butyl, tert-butyl, sec-butyl, pentyl, hexyl, heptyl, —$OCH_3$, —$OCH_2CH_3$, or —$CF_3$. In some embodiments $R^4$ can also be NR'R" wherein R' and R" are taken together with the nitrogen to form a cyclic moiety having from 3 to 8 ring atoms. The cyclic moiety so formed may further include one or more heteroatoms which are selected from the group consisting of S, O, and N. The cyclic moiety so formed is unsubstituted or substituted, including but not limited to morpholinyl, azetidinyl, pyrrolidinyl, piperidinyl, piperazinyl, isothiazolidinyl 1,2, dioxide, and thiomorpholinyl. Further non-limiting exemplary cyclic moieties are the following:

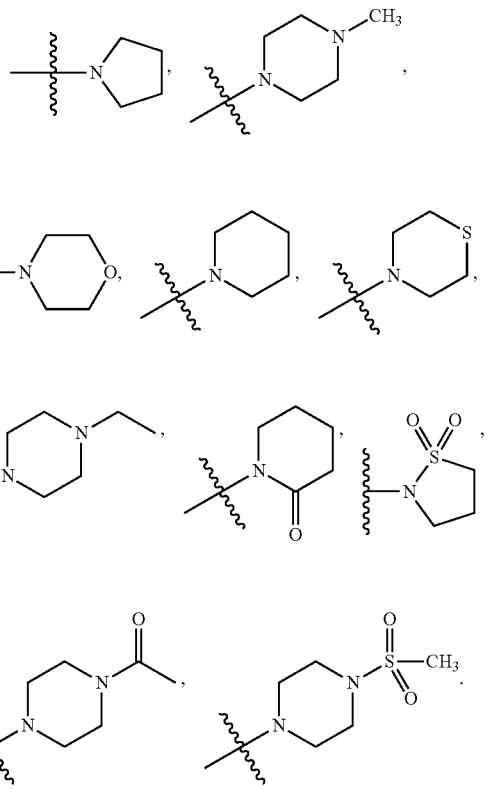

In some embodiments, the substituents $R^3$, $R^4$, $R^5$, or $R^8$ may be any of the substituents shown in Table 1:

TABLE 1
R³, R⁴, R⁵, R⁸ moieties of the compounds of Formula I, each independently includes but is not limited to the following:
| Subclass # | R |
|---|---|
| R-1 | 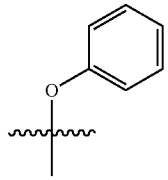 [SMILES: *Oc1ccccc1] |
| R-2 | 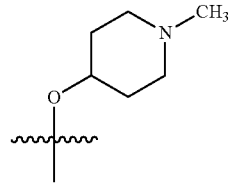 [SMILES: *OC1CCN(C)CC1] |
| R-3 | 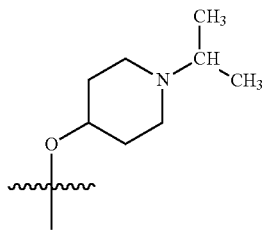 [SMILES: *OC1CCN(C(C)C)CC1] |
| R-4 | 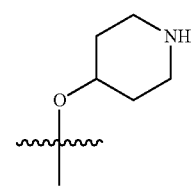 [SMILES: *OC1CCNCC1] |
| R-5 | 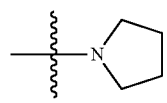 |
| R-6 | 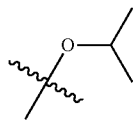 |
| R-7 | 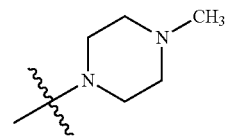 [SMILES: *N1CCN(C)CC1] |
| R-8 | 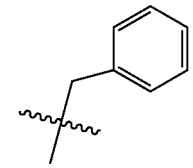 [SMILES: *Cc1ccccc1] |
| R-9 | —CH(CH₃)₂ |
| R-10 | 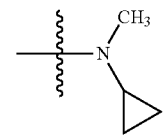 [SMILES: *N(C)C1CC1] |
| R-11 | 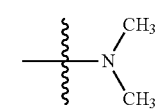 |
| R-12 | 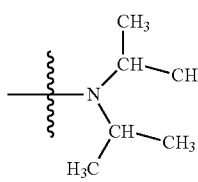 |
| R-13 | 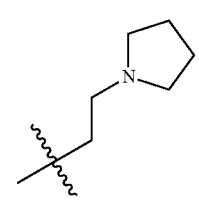 [SMILES: *CCN1CCCC1] |
| R-14 | 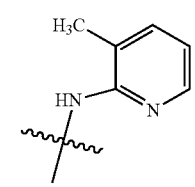 [SMILES: *Nc1ncccc1C] |
| R-15 | 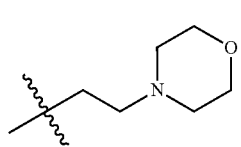 [SMILES: *CCN1CCOCC1] |
| R-16 | 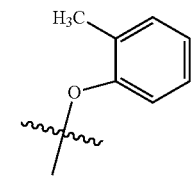 [SMILES: *Oc1ccccc1C] |
| R-17 | 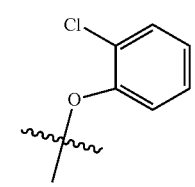 [SMILES: *Oc1ccccc1Cl] |
| R-18 | 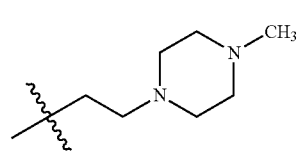 [SMILES: *CCN1CCN(C)CC1] |

TABLE 1-continued

R³, R⁴, R⁵, R⁸ moieties of the compounds of Formula I, each independently includes but is not limited to the following:

| Subclass # | R |
|---|---|
| R-19 | 4-(N-methylamino)benzonitrile |
| R-20 | morpholine |
| R-21 | N-methyl-4-aminotetrahydropyran |
| R-22 | 5-(indazolyloxy) |
| R-23 | 2-methoxyphenoxy |
| R-24 | 2-methylthiazol-4-yl propyl |
| R-25 | 1-acetylpiperidin-4-yloxy |
| R-26 | 5-(N-methylamino)indazole |
| R-27 | 5-(indazolyl)propyl |
| R-28 | 4-(4-ethylpiperazin-1-yl)propyl |
| R-29 | 4-(2-cyanoethyl)piperidin-1-yl propyl |
| R-30 | 1-(2-cyanoethyl)piperidin-4-yloxy |
| R-31 | 1-acetylpiperidin-4-yl propyl |
| R-32 | 1-acetylpiperidin-4-yloxy |
| R-33 | 1-(2-hydroxyethyl)piperidin-4-yloxy |

TABLE 1-continued

R³, R⁴, R⁵, R⁸ moieties of the compounds of Formula I, each independently includes but is not limited to the following:

| Subclass # | R |
| --- | --- |
| R-34 | piperidine with 4-CH₂CH₂- linker to stereocenter and N-CH₂CH₂OH |
| R-35 | 4-O-piperidine with N-CH₂CH₂SO₂Me |
| R-36 | piperidine with 4-CH₂CH₂- linker and N-CH₂CH₂SO₂Me |
| R-37 | 2-pyridyloxy |
| R-38 | 2-(2-pyridyl)ethyl |
| R-39 | thiazol-4-yl |
| R-40 | H |
| R-41 | 2-(diethylamino)thiazol-4-yl |
| R-42 | 2-(imidazol-1-yl)thiazol-4-yl |
| R-43 | piperidin-1-yl |
| R-44 | 2-oxopiperidin-1-yl |
| R-45 | thiomorpholin-4-yl |
| R-46 | 4-ethylpiperazin-1-yl |
| R-47 | 4-(N-methylsulfonyl)piperidin-4-yloxy |
| R-48 | tetrahydropyran-4-yloxy |
| R-49 | (tetrahydropyran-4-yl)methoxy |
| R-50 | (1-acetylpiperidin-4-yl)methoxy |

TABLE 1-continued

R³, R⁴, R⁵, R⁸ moieties of the compounds of Formula I, each independently includes but is not limited to the following:

| Subclass # | R |
|---|---|
| R-51 | 4-((methylsulfonyl)piperidin-4-yl)methoxy group |
| R-52 | 2-(pyrrolidin-1-yl)ethoxy group |
| R-53 | (1-methylpiperidin-4-yl)methoxy group |
| R-54 | 2-(4-acetylpiperazin-1-yl)ethoxy group |
| R-55 | 2-morpholinoethoxy group |
| R-56 | 2-(4-methylpiperazin-1-yl)ethoxy group |
| R-57 | 3-(4-(methylsulfonyl)piperazin-1-yl)propyl group |
| R-58 | 2-(4-(methylsulfonyl)piperazin-1-yl)ethoxy group |
| R-59 | 3-(4-acetylpiperazin-1-yl)propyl group |
| R-60 | (1-acetylpiperidin-4-yl)amino group |
| R-61 | (1-methylpiperidin-4-yl)amino group |
| R-62 | (tetrahydro-2H-pyran-4-yl)amino group |

TABLE 1-continued
R³, R⁴, R⁵, R⁸ moieties of the compounds of Formula I, each independently includes but is not limited to the following:
| Subclass # | R |
|---|---|
| R-63 | 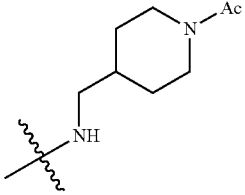 [SMILES: *NCC1CCN(C(C)=O)CC1] |
| R-64 | 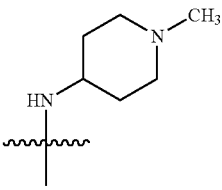 [SMILES: *NC1CCN(C)CC1] |
| R-65 | 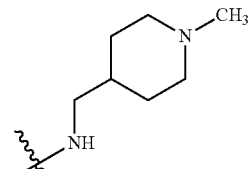 |
| R-66 | 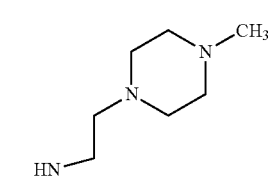 |
| R-67 | 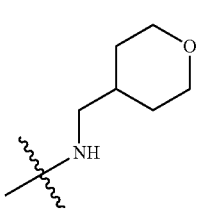 [SMILES: *NCC1CCOCC1] |
| R-68 | 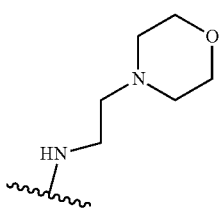 [SMILES: *NCCN1CCOCC1] |
| R-69 | 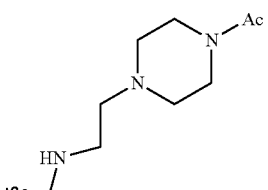 |
| R-70 | 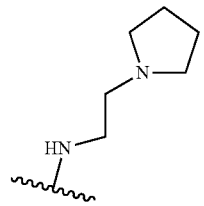 [SMILES: *NCCN1CCCC1] |
| R-71 | 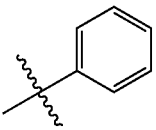 [SMILES: *c1ccccc1] |
| R-72 | 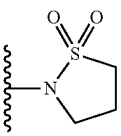 |
| R-73 | 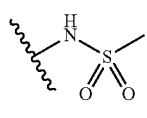 |
| R-74 | 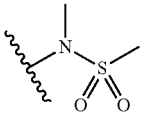 [SMILES: *N(C)S(C)(=O)=O] |
| R-75 | 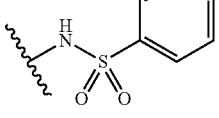 |
| R-76 | 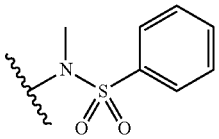 [SMILES: *N(C)S(=O)(=O)c1ccccc1] |
| R-77 | 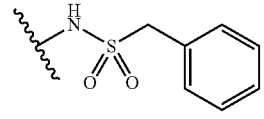 [SMILES: *NS(=O)(=O)Cc1ccccc1] |
| R-78 | 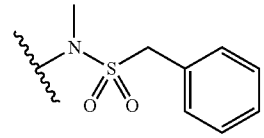 [SMILES: *N(C)S(=O)(=O)Cc1ccccc1] |
| R-79 | 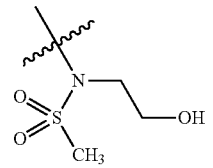 |

TABLE 1-continued

R³, R⁴, R⁵, R⁸ moieties of the compounds of Formula I, each
independently includes but is not limited to the following:

| Subclass # | R |
|---|---|
| R-80 | (4-cyanophenyl)methyl |
| R-81 | N-(2-morpholinoethyl)methanesulfonamide |
| R-82 | 3-(4-methylpiperazin-1-yl)azetidine |
| R-83 | 3-((S)-3-methylpiperazin-1-yl)azetidine |
| R-84 | 3-((R)-3-methylpiperazin-1-yl)azetidine |
| R-85 | 3-(4-ethylpiperazin-1-yl)azetidine |
| R-86 | 3-(4-isopropylpiperazin-1-yl)azetidine |

In general, compounds of the invention may be prepared by the following reaction scheme:

Scheme A:

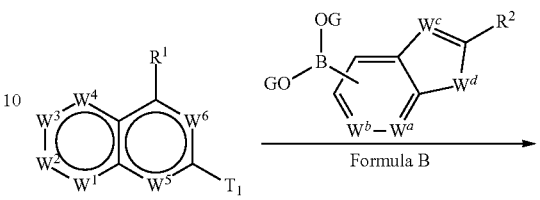

Formula A

Formula B

Formula C

The compounds of the invention may be synthesized via a reaction scheme represented generally in Schemes A and B. The synthesis proceeds via coupling a compound of Formula A with a compound of Formula B to yield a compound of Formula C. The coupling step is typically catalyzed by using a palladium catalyst, including but not limited to palladium tetrakis (triphenylphosphine). The coupling is generally performed in the presence of a suitable base, a nonlimiting example being sodium carbonate. One example of a suitable solvent for the reaction is aqueous dioxane.

A compound of Formula A for use in Scheme A has a structure of Formula A, wherein $T_1$ is halo including bromo, chloro, fluoro, and iodo, and wherein the remaining substituents are defined for Formulas I and II of compounds of the invention. For boronic acids and acid derivatives as depicted in Formula B, X is either O or S, and the benzoxazole or benzothiazole moiety can be attached at the 4-, 5-, 6- or 7-position.

For a compound of Formula B, G is hydrogen or $R_{G1}$, wherein $R_{G1}$ is alkyl, alkenyl, or aryl. Alternatively, $B(OG)_2$ is taken together to form a 5- or 6-membered cyclic moiety. In some embodiments, the compound of Formula B is a compound having a structure of Formula E:

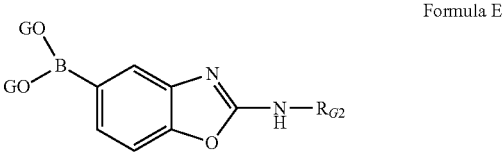

Formula E wherein G is H or $R_{G1}$; $R_{G1}$ is alkyl, alkenyl, or aryl. Alternatively, $B(OG)_2$ is taken together to form a 5- or 6-membered cyclic moiety; and $R_{G2}$ is H, tert-butyl carbamate, or acyl.

Scheme B:

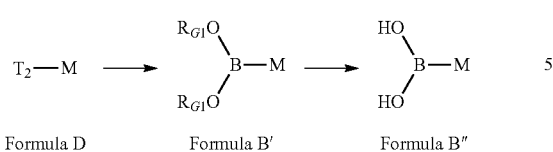

Formula D     Formula B'     Formula B"

Scheme B depicts an exemplary scheme for synthesizing a compound of Formula B' or, optionally, Formula B" for use in Reaction Scheme B. M is a heterocyclic moiety, such as benzoxazolyl or benzothiazolyl, as described by Formula B. This reaction proceeds via reacting a compound of Formula D with a trialkyl borate or a boronic acid derivative to produce a compound of Formula B'. The trialkyl borate includes but is not limited to triisopropyl borate and the boronic acid derivative includes but is not limited to bis(pinacolato)diboron. The reaction typically is run in the presence of a base, a nonlimiting example being potassium acetate. The reaction may be run in a solvent such as dioxane or tetrahydrofuran.

A compound of Formula D for use in Scheme B is a compound wherein $T_2$ is halo or another leaving group, and M is as defined above. The compound of Formula B' may further be converted to a compound of Formula B" by treatment with an acid such as hydrochloric acid.

Some exemplary compounds of Formula B that can be synthesized via Scheme B include but are not limited to compounds of the following formulae:

H-7

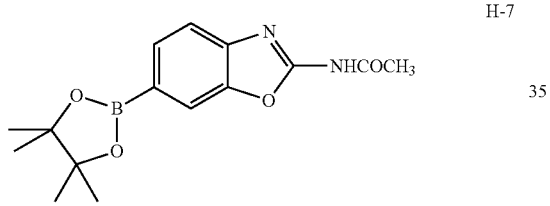

F-7

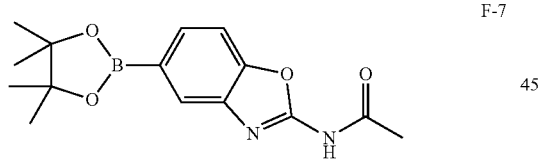

G-6

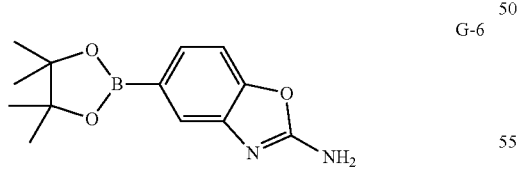

I-4

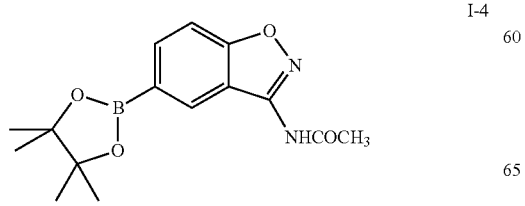

G-7

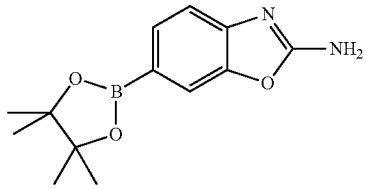

G-8

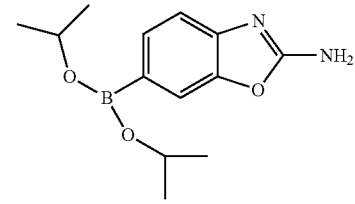

G-9

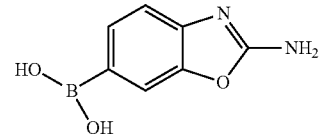

J-4

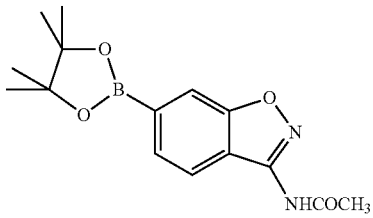

K-6

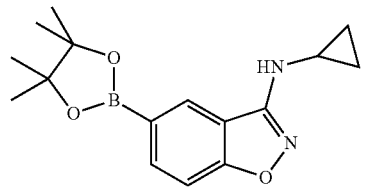

L-6

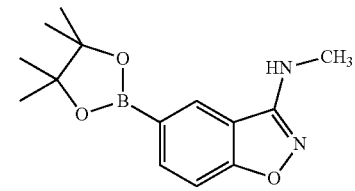

H-7-B

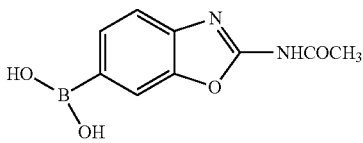

F-7-B

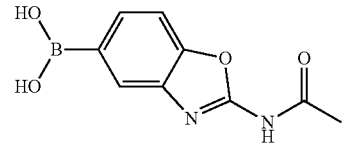

-continued

G-6-B
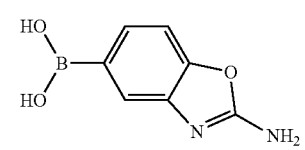

I-4-B
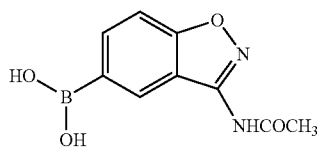

J-4-B

K-6-B

L-6-B
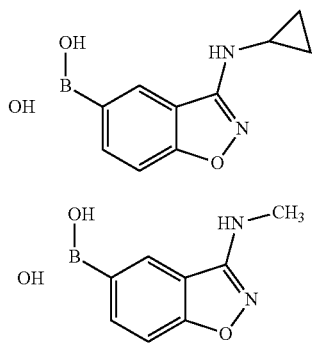

Where desired, deprotection of a substituent (e.g., removal of Boc protection from an amino substituent) on the benzoxazolyl moiety (i.e. $M_1$ of Formula C) is performed after coupling the compound of Formula B to the compound of Formula A.

Some exemplary compounds with such protecting groups, include but are not limited to compounds of the following formulae:

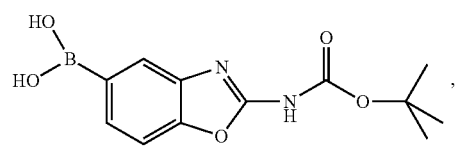

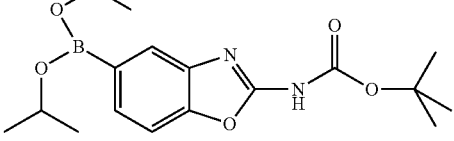

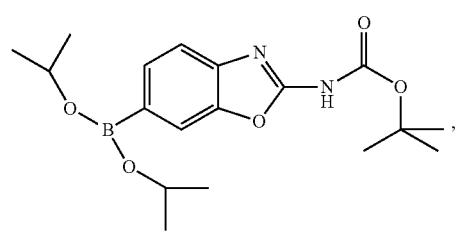

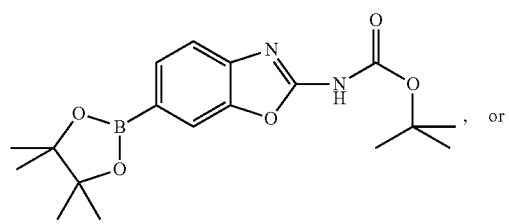
, or

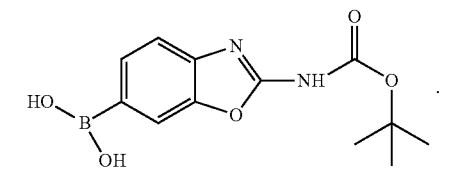
.

The following Reaction Schemes illustrate the preparation of several compounds of the invention.

Scheme C: Synthesis of 5-(7-(3-(4-isopropylpiperazin-1-yl)azetidin-1-yl)-1,5-naphthyridin-2-yl)benzo[d]oxazol-2-amine

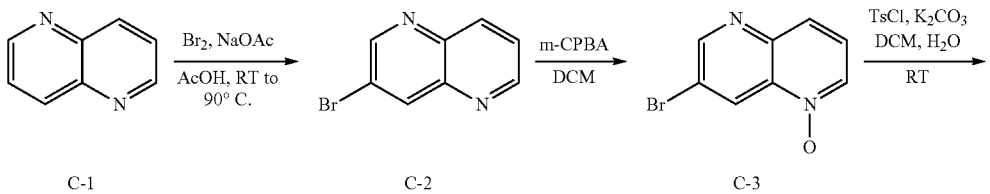

-continued
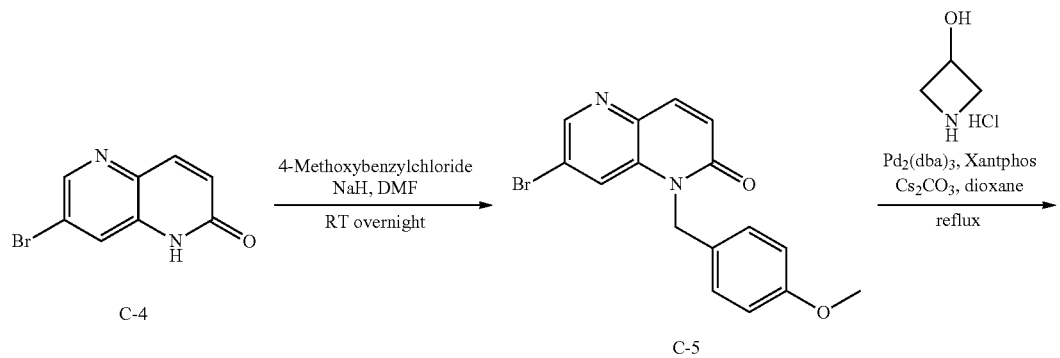
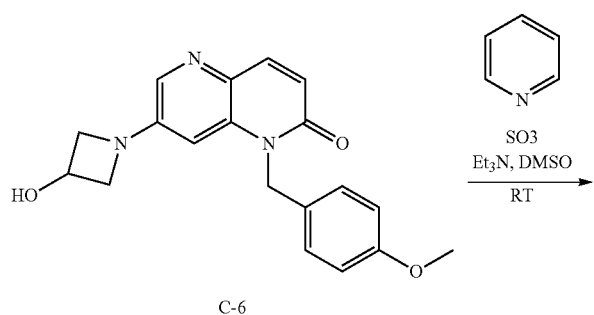
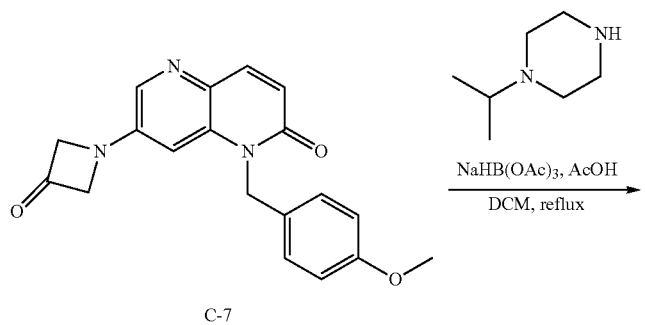
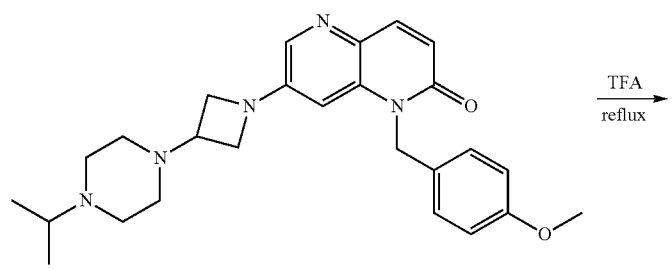
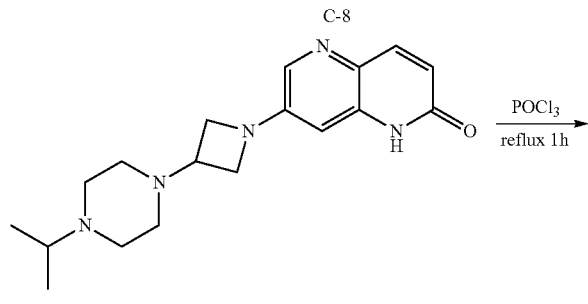

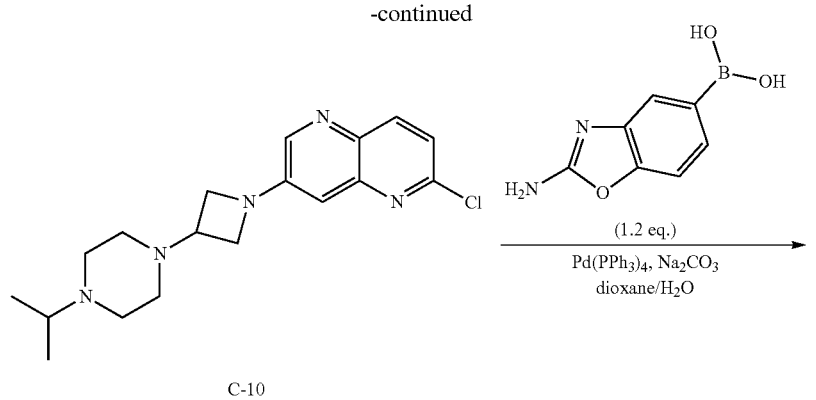
C-10
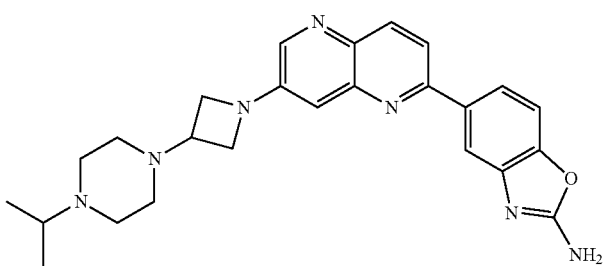
72
Scheme D: Synthesis of 2-amino-1-(4-(6-(2-aminobenzo[d]oxazol-5-yl)-1,5-naphthyridin-3-yl)piperazin-1-yl)-2-methylpropan-1-one
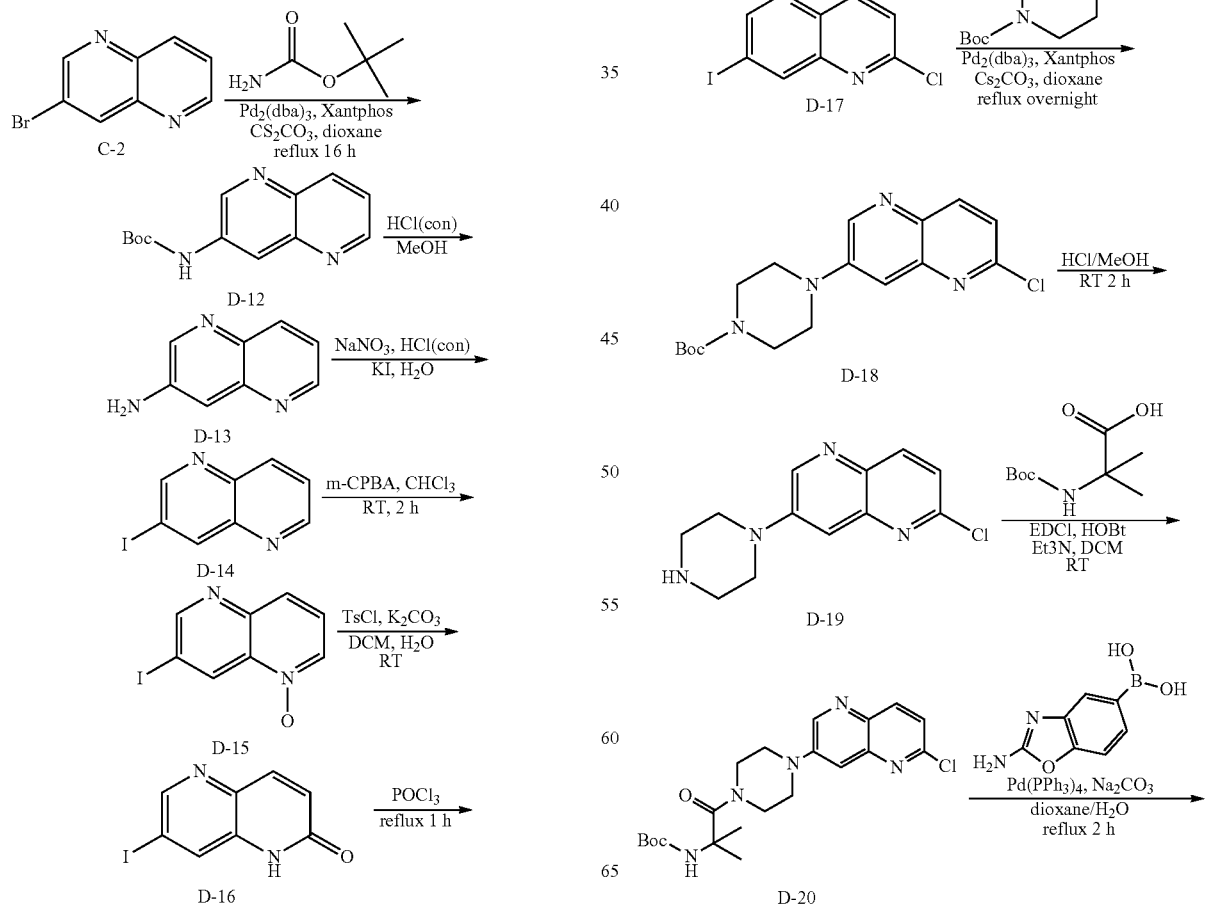

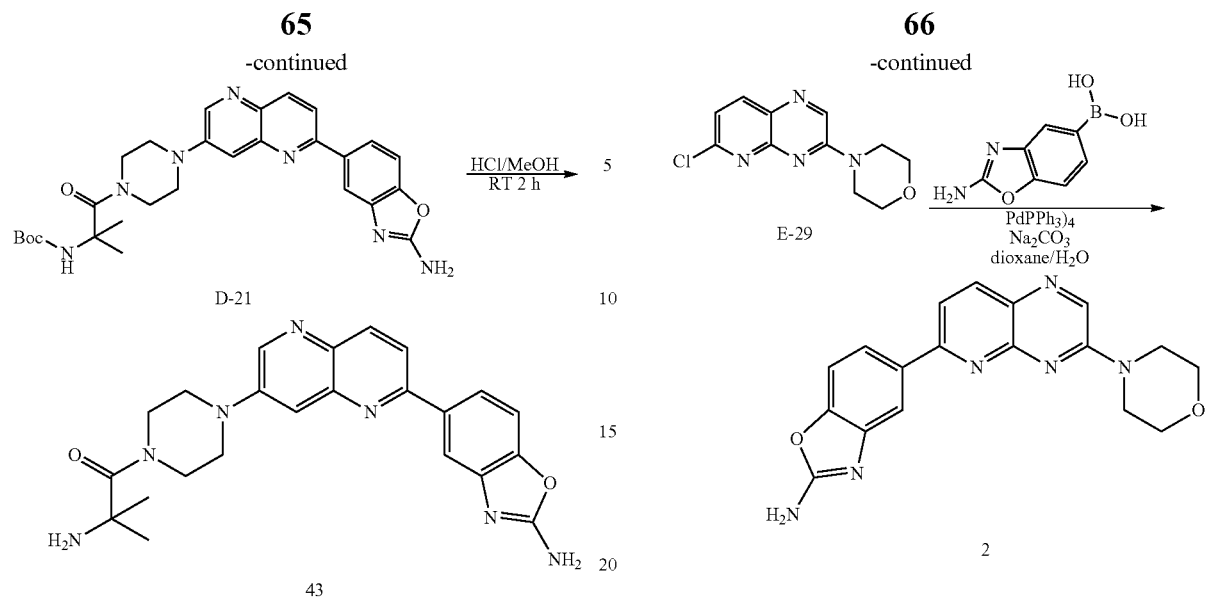

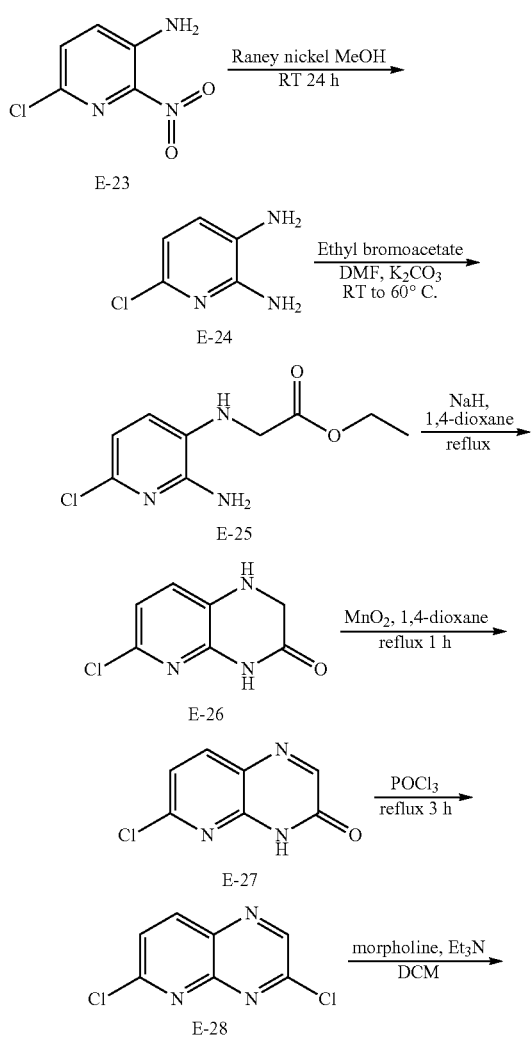

Scheme E: Synthesis of 5-(3-morpholinopyrido[2,3-b]pyrazin-6-yl)benzo[d]oxazol-2-amine

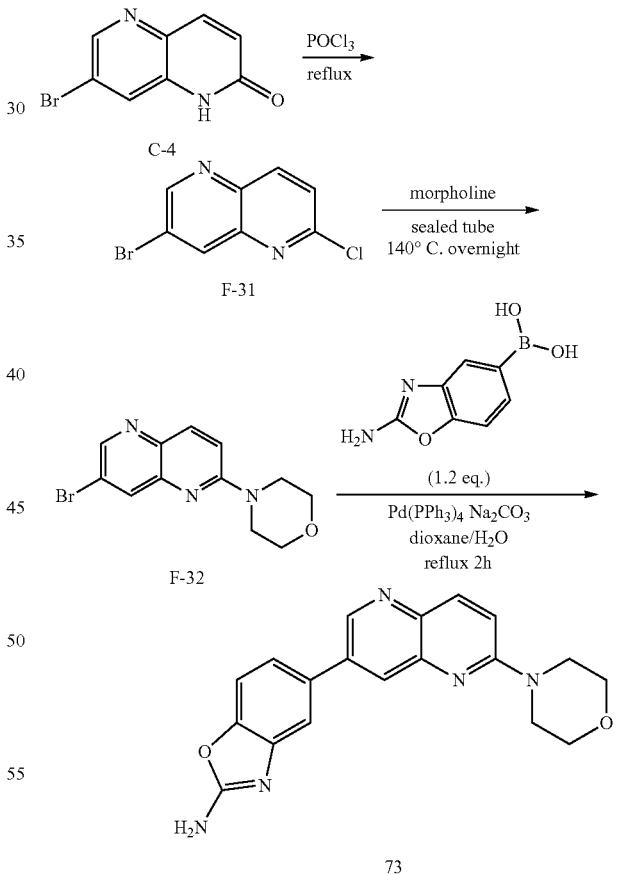

Scheme F: Synthesis of 5-(6-morpholino-1,5-napththyridin-3-yl)benzo[d]oxazol-2-amine The invention provides pharmaceutical compositions comprising one or more compounds of the present invention.

In some embodiments, the invention provides pharmaceutical compositions for the treatment of disorders such as hyperproliferative disorder including but not limited to cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, Induced cancer. In some embodiments, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

In some embodiments, the invention provides pharmaceutical compositions for treating diseases or conditions related to an undesirable, over-active, harmful or deleterious immune response in a mammal. Such undesirable immune response can be associated with or result in, e.g., asthma, emphysema, bronchitis, psoriasis, allergy, anaphylaxis, auto-immune diseases, rheumatoid arthritis, graft versus host disease, transplantation rejection, lung injuries, and lupus erythematosus. The pharmaceutical compositions of the present invention can be used to treat other respiratory diseases including but not limited to diseases affecting the lobes of lung, pleural cavity, bronchial tubes, trachea, upper respiratory tract, or the nerves and muscle for breathing. The compositions of the invention can be further used to treat multiorgan failure.

The invention also provides compositions for the treatment of liver diseases (including diabetes), pancreatitis or kidney disease (including proliferative glomerulonephritis and diabetes-induced renal disease) or pain in a mammal.

The invention also provides compositions for the treatment of sperm motility. The invention further provides compositions for the treatment of neurological or neurodegenerative diseases including, but not limited to, Alzheimer's disease, Huntington's disease, CNS trauma, and stroke.

The invention further provides a composition for the prevention of blastocyte implantation in a mammal.

The invention also relates to a composition for treating a disease related to vasculogenesis or angiogenesis in a mammal which can manifest as tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention further provides compositions for the treatment of disorders involving platelet aggregation or platelet adhesion, including but not limited to Bernard-Soulier syndrome, Glanzmann's thrombasthenia, Scott's syndrome, von Willebrand disease, Hermansky-Pudlak Syndrome, and Gray platelet syndrome.

In some embodiments, compositions are provided for treating a disease which is skeletal muscle atrophy, skeletal muscle hypertrophy, leukocyte recruitment in cancer tissue, invasion metastasis, melanoma, Kaposi's sarcoma, acute and chronic bacterial and viral infections, sepsis, glomerulo sclerosis, glomerulo, nephritis, or progressive renal fibrosis.

The subject pharmaceutical compositions are typically formulated to provide a therapeutically effective amount of a compound of the present invention as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the subject compounds and other agent(s) may be mixed into a preparation or both components may be formulated into separate preparations to use them in combination separately or at the same time.

In some embodiments, the concentration of one or more of the compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more of the compounds of the present invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more of the compounds of the present invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v. v/v.

In some embodiments, the concentration of one or more of the compounds of the present invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more of the compounds of the present invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more of the compounds of the present invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more of the compounds of the present invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition of the present invention typically contains an active ingredient (e.g., a compound of the present invention or a pharmaceutically acceptable salt and/or coordination complex thereof, and one or more pharmaceutically acceptable excipients, carriers, including but not limited inert solid diluents and fillers, diluents, sterile aqueous solution and various organic solvents, permeation enhancers, solubilizers and adjuvants.

Described below are non-limiting exemplary pharmaceutical compositions and methods for preparing the same.

Pharmaceutical Compositions for Oral Administration

In some embodiments, the invention provides a pharmaceutical composition for oral administration containing a compound of the present invention, and a pharmaceutical excipient suitable for oral administration.

In some embodiments, the invention provides a solid pharmaceutical composition for oral administration containing: (i) an effective amount of a compound of the present invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, .epsilon.-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, antifoaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Examples may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical (e.g., Transdermal) Delivery.

In some embodiments, the invention provides a pharmaceutical composition for transdermal delivery containing a compound of the present invention and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Compositions for Inhalation.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., See, e.g., Anderson, Philip O.; Knoben, James E.; Troutman, William G, eds., Handbook of Clinical Drug Data, Tenth Edition, McGraw-Hill, 2002; Pratt and Taylor, eds., *Principles of Drug Action*, Third Edition, Churchill Livingston, New York, 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. Compounds can also be administered intraadiposally or intrathecally.

The amount of the compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g., by dividing such larger doses into several small doses for administration throughout the day.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly(ether-ester)copolymers (e.g., PEO-PLLA); polydimethylsiloxane, poly(ethylene-vinylacetate), acrylate-based polymers or copolymers (e.g., polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. No. 5,451,233; U.S. Pat. No. 5,040,548; U.S. Pat. No. 5,061,273; U.S. Pat. No. 5,496,346; U.S. Pat. No. 5,292,331; U.S. Pat. No. 5,674,278; U.S. Pat. No. 3,657,744; U.S. Pat. No. 4,739,762; U.S. Pat. No. 5,195,984; U.S. Pat. No. 5,292,331; U.S. Pat. No. 5,674,278; U.S. Pat. No. 5,879,382; U.S. Pat. No. 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention, is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

The invention also provides kits. The kits include a compound or compounds of the present invention as described herein, in suitable packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, the compound of the present invention and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

The invention also provides methods of using the compounds or pharmaceutical compositions of the present invention to treat disease conditions, including but not limited to diseases associated with malfunctioning of one or more types of PI3 kinase (particularly PI3 kinase α), and/or mTOR. A detailed description of conditions and disorders mediated by p110δ kinase activity is set forth in Sadu et al., WO 01/81346, which is incorporated herein by reference in its entirety for all purposes.

The invention also relates to a method of treating a hyperproliferative disorder in a mammal that comprises administering to said mammal a therapeutically effective amount of a compound of the present invention, or a pharmaceutically acceptable salt, ester, prodrug, solvate, hydrate or derivative thereof. In some embodiments, said method relates to the treatment of cancer such as leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g., Lymphoma and Kaposi's Sarcoma) or viral-induced cancer. In some embodiments, the cancer is a brain glioma, glioblastoma, leukemia, Bannayan-Zonana syndrome, Cowden disease, Lhermitte-Duclos disease, breast cancer, inflammatory breast cancer, Wilm's tumor, Ewing's sarcoma, rhabdomyosarcoma, ependymoma, medulloblastoma, sarcoma, osteosarcoma, or a giant cell tumor of the bone or thyroid. In other embodiments, a compound of the invention is used to treat lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, immunoblastic large cell leukemia, multiple myeloma, mantle cell leukemia, megakaryoblastic leukemia, acute megakaryocytic leukemia, promyelocytic leukemia or erythroleukemia. In still other embodiments, the invention provides compounds for the treatment of malignant lymphoma, Hodgkins lymphoma, Non-Hodgkins lymphoma, lymphoblastic T cell lymphoma, Burkitt's lymphoma or follicular lymphoma. In other embodiments, the invention relates to treatment of a cancer which is neuroblastoma, bladder cancer, urothelial cancer, vulval cancer, endometrial cancer, mesothelioma, salivary gland cancer, hepatocellular cancer, nasopharangeal cancer, buccal cancer, and gastrointestinal stromal tumors.

In some embodiments, said method relates to the treatment of a non-cancerous hyperproliferative disorder such as benign hyperplasia of the skin (e. g., psoriasis), restenosis, or prostate (e. g., benign prostatic hypertrophy (BPH)).

The treatment methods provided herein comprise administering to the subject a therapeutically effective amount of a compound of the invention. In one embodiment, the present invention provides a method of treating an inflammation disorder, including autoimmune diseases in a mammal. The method comprises administering to said mammal a therapeutically effective amount of a compound of the present invention, or a pharmaceutically acceptable salt, ester, prodrug, solvate, hydrate or derivative thereof. Examples of autoimmune diseases include but are not limited to acute disseminated encephalomyelitis (ADEM), Addison's disease, antiphospholipid antibody syndrome (APS), aplastic anemia, autoimmune hepatitis, coeliac disease, Crohn's disease, Diabetes mellitus (type 1), Goodpasture's syndrome, Graves' disease, Guillain-Barré syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, Reiter's syndrome, Takayasu's arteritis, temporal arteritis (also known as "giant cell arteritis"), warm autoimmune hemolytic anemia, Wegener's granulomatosis, alopecia universalis, Chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders, thrombosis, lung inflammation, brain infection/inflammation, meningitis and encephalitis.

In one aspect, one or more of the subject methods may be effective in ameliorating symptoms associated with rheumatoid arthritis including but not limited to a reduction in the swelling of joints, a reduction in serum anti-collagen levels, and/or a reduction in joint pathology such as bone resorption, cartilage damage, pannus, and/or inflammation. In another aspect, the subject methods are effective in reducing ankle inflammation by at least about 2%, 5%, 10%, 15%, 20%, 25%, 30%, 50%, 60%, or about 75% to 90%. In another aspect, the subject methods are effective in reducing knee inflammation by at least about 2%, 5%, 10%, 15%, 20%, 25%, 30%, 50%, 60%, or about 75% to 90% or more. In still another aspect, the subject methods are effective in reducing serum anti-type II collagen levels by at least about 10%, 12%, 15%, 20%, 24%, 25%, 30%, 35%, 50%, 60%, 75%, 80%, 86%, 87%, or about 90% or more. In another aspect, the subject methods are effective in reducing ankle histopathology scores by about 5%, 10%, 15%, 20%, 25%, 30%, 40%, 50%, 60%, 75%, 80%, 90% or more. In still another aspect, the subject methods are effective in reducing knee histopathology scores by about 5%, 10%, 15%, 20%, 25%, 30%, 40%, 50%, 60%, 75%, 80%, 90% or more.

In other embodiments, the present invention provides methods of using the compounds or pharmaceutical compositions to treat respiratory diseases including but not limited to diseases affecting the lobes of lung, pleural cavity, bronchial tubes, trachea, upper respiratory tract, or the nerves and muscle for breathing. For example, methods are provided to treat obstructive pulmonary disease. Chronic obstructive pulmonary disease (COPD) is an umbrella term for a group of respiratory tract diseases that are characterized by airflow obstruction or limitation. Conditions included in this umbrella term are: chronic bronchitis, emphysema, and bronchiectasis.

In another embodiment, the compounds described herein are used for the treatment of asthma. Also, the compounds or pharmaceutical compositions described herein may be used for the treatment of endotoxemia and sepsis. In one embodiment, the compounds or pharmaceutical compositions described herein are used to for the treatment of rheumatoid arthritis (RA). In yet another embodiment, the compounds or pharmaceutical compositions described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

In other embodiments, the compounds described herein are used for the treatment of heart conditions including atherosclerosis, heart hypertrophy, cardiac myocyte dysfunction, elevated blood pressure and vasoconstriction. The invention also relates to a method of treating diseases related to vasculogenesis or angiogenesis in a mammal that comprises administering to said mammal a therapeutically effective amount of a compound of the present invention, or a pharmaceutically acceptable salt, ester, prodrug, solvate, hydrate or derivative thereof. In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with compounds of the present invention, or pharmaceutically acceptable salt, ester, prodrug, solvate, hydrate or derivative of said compounds, according to the methods of this invention include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

The invention also relates to a method of treating diabetes in a mammal that comprises administering to said mammal a therapeutically effective amount of a compound of the present invention, or a pharmaceutically acceptable salt, ester, prodrug, solvate, hydrate or derivative thereof.

In addition, the compounds described herein may be used to treat acne.

In addition, the compounds described herein may be used for the treatment of arteriosclerosis, including atherosclerosis. Arteriosclerosis is a general term describing any hardening of medium or large arteries. Atherosclerosis is a hardening of an artery specifically due to an atheromatous plaque.

Further the compounds described herein may be used for the treatment of glomerulonephritis. Glomerulonephritis is a primary or secondary autoimmune renal disease characterized by inflammation of the glomeruli. It may be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

Additionally, the compounds described herein may be used for the treatment of bursitis, lupus, acute disseminated encephalomyelitis (ADEM), addison's disease, antiphospholipid antibody syndrome (APS), aplastic anemia, autoimmune hepatitis, coeliac disease, crohn's disease, diabetes mellitus (type 1), goodpasture's syndrome, graves' disease, guillain-barré syndrome (GBS), hashimoto's disease, inflammatory bowel disease, lupus erythematosus, myasthenia gravis, opsoclonus myoclonus syndrome (OMS), optic neuritis, ord's thyroiditis, ostheoarthritis, uveoretinitis, pemphigus, polyarthritis, primary biliary cirrhosis, reiter's syndrome, takayasu's arteritis, temporal arteritis, warm autoimmune hemolytic anemia, wegener's granulomatosis, alopecia universalis, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

The invention also relates to a method of treating a cardiovascular disease in a mammal that comprises administering to said mammal a therapeutically effective amount of a compound of the present invention, or a pharmaceutically acceptable salt, ester, prodrug, solvate, hydrate or derivative thereof. Examples of cardiovascular conditions include, but are not limited to, atherosclerosis, restenosis, vascular occlusion, carotid obstructive disease, or ischemic conditions.

In another aspect, the present invention provides methods of disrupting the function of a leukocyte or disrupting a function of an osteoclast. The method includes contacting the leukocyte or the osteoclast with a function disrupting amount of a compound of the invention.

In another aspect of the present invention, methods are provided for treating ophthalmic disease by administering one or more of the subject compounds or pharmaceutical compositions to the eye of a subject.

Methods are further provided for administering the compounds of the present invention via eye drop, intraocular injection, intravitreal injection, topically, or through the use of a drug eluting device, microcapsule, implant, or microfluidic device. In some cases, the compounds of the present invention are administered with a carrier or excipient that increases the intraocular penetrance of the compound such as an oil and water emulsion with colloid particles having an oily core surrounded by an interfacial film.

In some cases, the colloid particles include at least one cationic agent and at least one non-ionic surfactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quaternary ammonium compound, a cationic lipid, an amino alcohol, a biguanidine salt, a cationic compound or a mixture thereof. In some cases the cationic agent is a biguanidine salt such as chlorhexidine, polyaminopropyl biguanidine, phenformin, alkylbiguanidine, or a mixture thereof. In some cases, the quaternary ammonium compound is a benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, rnyristylalkonium halide, stearalkonium halide or a mixture of two or more thereof. In some cases, cationic agent is a benzalkonium chloride, lauralkonium chloride, benzododecinium bromide, benzethonium chloride, hexadecyltrimethylammonium bromide, tetradecyltrimethylammonium bromide, dodecyltrimethylammonium bromide or a mixture of two or more thereof. In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising polyoxyl-40 hydrogenated castor oil, polyoxyl-60 hydrogenated castor oil or polyoxyl-100 hydrogenated castor oil.

The invention further provides methods of modulating a PI3K and/or mTor kinase activity by contacting the kinase with an amount of an effective amount of compound of the invention. Modulate can be inhibiting or activating kinase activity. In some embodiments, the invention provides methods of inhibiting kinase activity by contacting the kinase with an amount of an effective amount of a compound of the invention in solution. In some embodiments, the invention provides methods of inhibiting the kinase activity by contacting a cell, tissue, organ that express the kinase of interest. In some embodiments, the invention provides methods of inhibiting kinase activity in subject including but not limited to rodents and mammal (e.g., human) by administering into the subject an effective amount of a compound of the invention. In some embodiments, the percentage of inhibiting exceeds 50%, 60%, 70%, 80%, or 90%.

In some embodiments, the kinase is selected from the group consisting of PI3 kinase including different isoforms such as PI3 kinase α, PI3 kinase β, PI3 kinaseγ, PI3 kinase δ; DNA-PK; mTor; Abl, VEGFR, Ephrin receptor B4 (EphB4); TEK receptor tyrosine kinase (TIE2); FMS-related tyrosine kinase 3 (FLT-3); Platelet derived growth factor receptor (PDGFR); RET; ATM; ATR; hSmg-1; Hck; Src; Epidermal growth factor receptor (EGFR); KIT; Insulin Receptor (IR) and IGFR.

The present invention also provides methods for combination therapies in which an agent known to modulate other pathways, or other components of the same pathway, or even overlapping sets of target enzymes are used in combination with a compound of the present invention, or a pharmaceutically acceptable salt, ester, prodrug, solvate, hydrate or derivative thereof. In one aspect, such therapy includes but is not limited to the combination of the subject compound with chemotherapeutic agents, therapeutic antibodies, and radiation treatment, to provide a synergistic or additive therapeutic effect.

For treatment of autoimmune diseases, the subject compounds or pharmaceutical compositions can be used in combination with commonly prescribed drugs including but not limited to Enbrel®, Remicade®, Humira®, Avonex®, and Rebif®. For treatment of respiratory diseases, the subject compounds or pharmaceutical compositions can be administered in combination with commonly prescribed drugs including but not limited to Xolair®, Advair®, Singulair®, and Spiriva®.

The compounds of the invention may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g., acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone. Chloroquine (Aralen) or hydroxychloroquine (Plaquenil) may also be very useful in some individuals with lupus. They are most often prescribed for skin and joint symptoms of lupus. Azathioprine (Imuran) and cyclophosphamide (Cytoxan) suppress inflammation and tend to suppress the immune system. Other agents, e.g., methotrexate and cyclosporin are used to control the symptoms of lupus. Anticoagulants are employed to prevent blood from clotting rapidly. They range from aspirin at very low dose which prevents platelets from sticking, to heparin/coumadin.

In another one aspect, this invention also relates to methods and pharmaceutical compositions for inhibiting abnormal cell growth in a mammal which comprises an amount of a compound of the present invention, or a pharmaceutically acceptable salt, ester, prodrug, solvate, hydrate or derivative thereof, in combination with an amount of an anti-cancer agent (e.g., a chemotherapeutic agent). Many chemotherapeutics are presently known in the art and can be used in combination with the compounds of the invention.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, immunotherapeutic agents, proapoptotic agents, and anti-androgens. Non-limiting examples are chemotherapeutic agents, cytotoxic agents, and non-peptide small molecules such as Gleevec (Imatinib Mesylate), Velcade (bortezomib), Casodex (bicalutamide), Iressa (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, ranimustine; oxazaphosphorines; nitrosoureas; triazenes; antibiotics such as anthracyclins, actinomycins and bleomycins including aclacinomysins, actinomycin, anthramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; gemcitabine and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum or platinum analogs and complexes such as cisplatin and carboplatin; anti-microtubule such as diterpenoids, including paclitaxel and docetaxel, or Vinca alkaloids including vinblastine, vincristine, vinflunine, vindesine, and vinorelbine; etoposide (VP-16); ifosfamide; mitomycin C; mitoxantrone; vincristine; vinorelbine; navelbine; novantrone; teniposide; daunomycin; aminopterin; xeloda; ibandronate; topoisomerase I and II inhibitors including camptothecins (e.g., camptothecin-11), topotecan, irinotecan, and epipodophyllotoxins; topoisomerase inhibitor RFS 2000; epothilone A or B; difluoromethylornithine (DMFO); histone deacetylase inhibitors; compounds which induce cell differentiation processes; gonadorelin agonists; methionine aminopeptidase inhibitors; compounds targeting/decreasing a protein or lipid kinase activity; compounds which target, decrease or inhibit the activity of a protein or lipid phosphatase; anti-androgens; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors; temozolomide (TEMODAL®); Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (TEMODAL®); kinesin spindle protein inhibitors, such as SB715992 or SB743921 from GlaxoSmithKline, or pentamidine/chlorpromazine from CombinatoRx; MEK inhibitors such as ARRY142886 from Array PioPharma, AZD6244 from AstraZeneca, PD181461 or PD0325901 from Pfizer, leucovorin, EDG binders, antileukemia compounds, ribonucleotide reductase inhibitors, S-adenosylmethionine decarboxylase inhibitors, antiproliferative antibodies or other chemotherapeutic compounds. Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, and Velcade®. Further information on compounds which may be used in conjunction with the compounds of the invention is provided below.

Proteasome inhibitors include compounds which target, decrease or inhibit the activity of the proteasome. Compounds which target, decrease or inhibit the activity of the proteasome include e.g., Bortezomid (Velcade™) and MLN 341. Matrix metalloproteinase inhibitors ("MMP" inhibitors) include, but are not limited to, collagen peptidomimetic and nonpeptidomimetic inhibitors, tetracycline derivatives, e.g., hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996. Compounds used in the treatment of hematologic malignancies include, but are not limited to, FMS-like tyrosine kinase inhibitors e.g., compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g., compounds which target, decrease or inhibit anaplastic lymphoma kinase. Compounds which target, decrease or inhibit the activity of FMS-like tyrosine kinase receptors (Flt-3R) are especially compounds, proteins or antibodies which inhibit members of the Flt-3R receptor kinase family, e.g., PKC412, midostaurin, a staurosporine derivative, SU11248 and MLN518.

Hsp90 inhibitors include compounds such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozo-lomide (TEMODAL®); kinesin spindle protein inhibitors, such as SB715992 or SB743921 from GlaxoSmithKline, or pentamidine/chlorpromazine from CombinatoRx; MEK inhibitors such as ARRY142886 from Array PioPharma, AZD6244 from AstraZeneca, PD181461 from Pfizer, leucovorin, EDG binders, antileukemia compounds, ribonucleotide reductase inhibitors, S-adenosylmethionine decarboxylase inhibitors, antiproliferative antibodies or other chemotherapeutic compounds.

Histone deacetylase inhibitors (or "HDAC inhibitors") include compounds which inhibit a histone deacetylase and which possess antiproliferative activity. This includes compounds disclosed in WO 02/22577, especially N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(2-methyl-1H-indol-3-yl)-ethyl]amino]methyl]phenyl]-2E-2-propenamide and pharmaceutically acceptable salts thereof. It further especially includes Suberoylanilide hydroxamic acid (SAHA).

Bisphosphonates for use in combination with the compounds of the invention include, but are not limited to, etridonic, clodronic, tiludronic, pamidronic, alendronic, ibandronic, risedronic and zoledronic acid.

Compounds of the invention may also be used in conjunction with compounds targeting or decreasing a protein or lipid kinase activity, a protein or lipid phosphatase activity, or further anti-angiogenic compounds. Such compounds include, but are not limited to, protein tyrosine kinase and/or serine and/or threonine kinase inhibitors or lipid kinase inhibitors, e.g., compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g., a N-phenyl-2-pyrimidine-amine derivative, e.g., imatinib, SU101, SU6668 and GFB-1 11; compounds targeting, decreasing or inhibiting the activity of the fibroblast growth factor-receptors (FGFR); compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599 or such as OSI906, or antibodies that target the extracellular domain of IGF-I receptor such as CP-751871, R1507, AVE1642, IMC-A12, AMG479, MK-0646, SCH717454 or its growth factors; compounds targeting, decreasing or inhibiting the activity of the Trk receptor tyrosine kinase family, or ephrin B4 inhibitors; compounds targeting, decreasing or inhibiting the activity of the AxI receptor tyrosine kinase family; compounds targeting, decreasing or inhibiting the activity of the Ret receptor tyrosine kinase; compounds targeting, decreasing or inhibiting the activity of the Kit/SCFR receptor tyrosine kinase, e.g., imatinib; compounds targeting, decreasing or inhibiting the activity of the C-kit receptor tyrosine kinases—(part of the PDGFR family), such as compounds which target, decrease or inhibit the activity of the c-Kit receptor tyrosine kinase family, especially compounds which inhibit the c-Kit receptor, e.g., imatinib; compounds targeting, decreasing or inhibiting the activity of members of the c-Abl family, their gene-fusion products (e.g., BCR-AbI kinase) and mutants, such as compounds which target decrease or inhibit the activity of c-Abl family members and their gene fusion products, e.g., a N-phenyl-2-pyrimidine-amine derivative, e.g., imatinib or nilotinib (AMN107); PD180970; AG957; NSC 680410; PD173955 from ParkeDavis; or dasatinib (BMS-354825); compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g., midostaurin; examples of further compounds include e.g., UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; PD184352 or QAN697 (a PI3K inhibitor) or AT7519 (CDK inhibitor); compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin).

Compounds of the invention may also be used in combination with compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g., EGF receptor, ErbB2, ErbB3 and ErbB4 or bind to EGF or EGF related ligands, and are in particular those compounds, proteins or monoclonal antibodies generically and specifically disclosed in WO 97/02266, e.g., the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g., compound known as CP 358774), WO 96/33980 (e.g., compound ZD 1839) and WO 95/03283 (e.g., compound ZM105180); e.g., trastuzumab (Herceptin™), cetuximab (Erbitux™), Iressa, Tarceva, OSI-774, C1-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF. Further anti-angiogenic compounds include compounds having another mechanism for their activity, e.g., unrelated to protein or lipid kinase inhibition e.g., thalidomide (THALOMID) and TNP-470.

Non-receptor kinase angiogenesis inhibitors may also be useful in conjunction with the compounds of the present invention. Angiogenesis in general is linked to erbB21EGFR signaling since inhibitors of erbB2 and EGFR have been shown to inhibit angiogenesis, primarily VEGF expression. Accordingly, non-receptor tyrosine kinase inhibitors may be used in combination with the compounds of the present invention. For example, anti-VEGF antibodies, which do not recognize VEGFR (the receptor tyrosine kinase), but bind to the ligand; small molecule inhibitors of integrin (alphav beta3) that will inhibit angiogenesis; endostatin and angiostatin (non-RTK) may also prove useful in combination with the disclosed compounds. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Compounds which target, decrease or inhibit the activity of a protein or lipid phosphatase include e.g., inhibitors of phosphatase 1, phosphatase 2A, or CDC25, e.g., okadaic acid or a derivative thereof. Compounds which induce cell differentiation processes are e.g., retinoic acid, α- γ- or δ-tocopherol or α- γ- or δ-tocotrienol. Cyclooxygenase inhibitors include, but are not limited to, e.g., Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g., 5-methyl-2-(2'-chloro-6'-fluoroanilino)phenyl acetic acid, and lumiracoxib.

Heparanase inhibitors includes compounds which target, decrease or inhibit heparin sulfate degradation, including, but not limited to, PI-88. Biological response modifiers include lymphokines and interferons, e.g., interferon γ. Inhibitors of Ras oncogenic isoforms include H-Ras, K-Ras, N-Ras, and other compounds which target, decrease or inhibit the oncogenic activity of Ras. Farnesyl transferase inhibitors include, but are not limited to, e.g., L-744832, DK8G557 and R115777 (Zarnestra).

Telomerase inhibitors include compounds which target, decrease or inhibit the activity of telomerase. Compounds which target, decrease or inhibit the activity of telomerase are especially compounds which inhibit the telomerase receptor, e.g., telomestatin. Methionine aminopeptidase inhibitors are, for example, compounds which target, decrease or inhibit the activity of methionine aminopeptidase. Compounds which target, decrease or inhibit the activity of methionine aminopeptidase are e.g., bengamide or a derivative thereof.

Antiproliferative antibodies include, but are not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant e.g., intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the invention can be used in combination with standard leukemia therapies, especially in combination with therapies used for the treatment of AML. In particular, compounds of the invention can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Antileukemic compound for use in combination with compounds of the invention include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552, 065, in particular, Λ/-hydroxy-3-[4-[[[2-(2-methyl-1H-indol-3-yl)-ethyl]-amino]methyl]phenyl]-2E-2-propenamide, or a pharmaceutically acceptable salt thereof and Λ/-hydroxy-3-[4-[(2-hydroxyethyl){2-(1/−/-indol-3-yl)ethyl]-amino]methyl]phenyl]-2E-2-propenamide, or a pharmaceutically acceptable salt thereof, e.g., the lactate salt.

Somatostatin receptor antagonists include compounds which target, treat or inhibit the somatostatin receptor such as octreotide, and SOM230 (pasireotide). Tumor cell damaging approaches include approaches such as ionizing radiation, e.g., ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4th Edition, Vol. 1, pp. 248-275 (1993). EDG binders includes immunosuppressants that modulate lymphocyte recirculation, such as FTY720.

Ribonucleotide reductase inhibitors include pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are e.g., hydroxyurea or 2-hydroxy-1/–/-isoindole-1,3-dione derivatives, such as PL-1, PL-2, PL-3, PL-4, PL-5, PL-6, PL-7 or PL-8 mentioned in Nandy et al., Acta Oncologica, Vol. 33, No. 8, pp. 953-961 (1994).

S-adenosylmethionine decarboxylase inhibitors include, but are not limited to the compounds disclosed in U.S. Pat. No. 5,461,076.

Also included are in particular those compounds, proteins or monoclonal antibodies of VEGF disclosed in WO 98/35958, e.g., 1-(4-chloroanilino)-4-(4-pyridylmethyl)phthalazine or a pharmaceutically acceptable salt thereof, e.g., the succinate, or in WO 00/09495, WO 00/27820, WO 00/59509, WO 98/11223, WO 00/27819 and EP 0 769 947; those as described by Prewett et al, Cancer Res, Vol. 59, pp. 5209-5218 (1999); Yuan et al., Proc Natl Acad Sci USA, Vol. 93, pp. 14765-14770 (1996); Zhu et al., Cancer Res, Vol. 58, pp. 3209-3214 (1998); and Mordenti et al., Toxicol Pathol, Vol. 27, No. 1, pp. 14-21 (1999); in WO 00/37502 and WO 94/10202; ANGIOSTATIN, described by O'Reilly et al., Cell, Vol. 79, pp. 315-328 (1994); ENDOSTATIN, described by O'Reilly et al., Cell, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g., rhuMAb and RHUFab, VEGF aptamer e.g., Macugon; FLT-4 inhibitors, FLT-3 inhibitors, VEGFR-2 IgGI antibody, Angiozyme (RPI 4610) and Bevacizumab (Avastin™)

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as described with an anti-inflammatory, bronchodilatory, antihistamine or anti-tussive drug substance, said compound of the invention and said drug substance being in the same or different pharmaceutical composition. Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/035668, WO 03/048181, WO 03/062259, WO 03/064445, WO 03/072592, non-steroidal glucocorticoid receptor agonists such as those described in WO 00/00531, WO 02/10143, WO 03/082280, WO 03/082787, WO 03/104195, WO 04/005229; LTB4 antagonists such LY29311 1, CGS025019C, CP-195543, SC-53228, BIIL 284, ONO 4057, SB 209247 and those described in U.S. Pat. No. 5,451,700; LTD4 antagonists such as montelukast and zafirlukast; PDE4 inhibitors such cilomilast (Ariflo® GlaxoSmithKline), Roflumilast (Byk Gulden), V-1 1294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; A2a agonists such as those disclosed in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083; A2b antagonists such as those described in WO 02/42298; and beta-2 adrenoceptor agonists such as albuterol (salbutamol), metaproterenol, terbutaline, salmeterol fenoterol, procaterol, and especially, formoterol and pharmaceutically acceptable salts thereof, and compounds (in free or salt or solvate form) of formula I of WO 0075114, which document is incorporated herein by reference, preferably compounds of the Examples thereof, as well as compounds (in free or salt or solvate form) of formula I of WO 04/16601, and also compounds of WO 04/033412. Suitable bronchodilatory drugs include anticholinergic or antimuscarinic compounds, in particular ipratropium bromide, oxitropium bromide, tiotropium salts and CHF 4226 (Chiesi), and glycopyrrolate, but also those described in WO 01/04118, WO 02/51841, WO 02/53564, WO 03/00840, WO 03/87094, WO 04/05285, WO 02/00652, WO 03/53966, EP 424021, U.S. Pat. No. 5,171,744, U.S. Pat. No. 3,714,357, WO 03/33495 and WO 04/018422.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in WO 03/099807, WO 04/026841 and JP 2004107299.

Other useful combinations of compounds of the invention with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351 125, SCH-55700 and SCH-D, Takeda antagonists such as TAK-770, and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Anti-microtubule or anti-mitotic agents include phase specific agents active against the microtubules of tumor cells during M or the mitosis phase of the cell cycle. Examples of anti-microtubule agents include, but are not limited to, diterpenoids and vinca alkaloids. Diterpenoids, which are derived from natural sources, are phase specific anti-cancer agents that operate at the $G_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel. Paclitaxel, 5β,20-epoxy-1,2α,4,7β,10β,13α-hexa-hydroxytax-11-en-9-one 4,10-diacetate 2-benzoate 13-ester with (2R,3S)-N-benzoyl-3-phenylisoserine; is a natural diterpene product isolated from the Pacific yew tree *Taxus brevifolia* and is commercially available as an injectable solution TAXOL®. It is a member of the taxane family of terpenes. One mechanism for its activity relates to paclitaxel's capacity to bind tubulin, thereby inhibiting cancer cell growth. Paclitaxel has been approved for clinical use in the treatment of refractory ovarian cancer in the United States and for the treatment of breast cancer. It is a potential candidate for treatment of neoplasms in the skin and head and neck carcinomas. The compound also shows potential for the treatment of polycystic kidney disease, lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995). Docetaxel, (2R,3S)—N-carboxy-3-phenylisoserine, N-tert-butyl ester, 13-ester with 5β-20-epoxy-1,2α,4,7β,10β,13α-hexahydroxytax-1-1-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids include phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine. Vinblastine, vincaleukoblastine sulfate, is commercially available as VELBAN® as an injectable solution. Although it has possible indication as a second line therapy of various solid tumors, it is primarily indicated in the treatment of testicular cancer and various lymphomas including Hodgkin's Disease, and lymphocytic and histiocytic lymphomas. Myelosuppression is the dose limiting side effect of vinblastine. Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur. Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes include non-phase specific anti-cancer agents, which interact with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin. Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity. Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents include non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine. Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide. Melphalan, 4-[bis(2-chloroethyl)amino]-L-phenylalanine, is commercially available as an injectable solution or tablets as ALKERAN®. Melphalan is indicated for the palliative treatment of multiple myeloma and non-respectable epithelial carcinoma of the ovary. Bone marrow suppression is the most common dose limiting side effect of melphalan. Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil. Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan. Carmustine, 1,3-[bis (2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine. Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics include non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins. Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin. Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin. Doxorubicin, (8 S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin. Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins. Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide. Etoposide, 4'-demethyl-epipodophyllotoxin 9[4,6-O—(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia. Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia. Other topoisomerase II inhibitors include epirubicin, idarubicin, nemorubicin, mitoxantrone, and losoxantrone.

Antimetabolite neoplastic agents include phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine. 5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate. Cytarabine, 4-amino-1-β-D-arabinofuranosyl-2(1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis. Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine. Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine. Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration. Methotrexate, N-[4-[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Topoisomerase I inhibitors include camptothecins such as camptothecin and camptothecin derivatives. Camptothecin cytotoxic activity is believed to be related to its Topoisomerase I inhibitory activity. Examples of camptothecins include, but are not limited to irinotecan and topotecan. Irinotecan HCl, (4S)-4,11-diethyl-4-hydroxy-9-[(4-piperidinopiperidino)carbonyloxy]-1H-pyrano[3',4',6,7]indolizino[1,2-b]quinoline-3,14(4H,12H)-dione hydrochloride, is commercially available as the injectable solution CAMPTOSAR®. Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irinotecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea. Topotecan HCl, (S)-10-[(dimethylamino) methyl]-4-ethyl-4,9-dihydroxy-1H-pyrano[3',4',6,7]-indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents relegation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as aminoglutethimide, roglethimide, pyridoglutethimide, trilostane, testolactone, ketokonazole, vorozole, fadrozole, anastrozole, letrazole, formestane, atamestane and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as fulvestrant, tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as abarelix, goserelin, goserelin acetate and luprolide. SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32 Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Also of interest for use with the compounds of the invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of inhibitors are signal transduction pathway inhibitors such as inhibitors of Ras Oncogene. Such inhibitors include inhibitors of farnesyltransferase, geranyl-geranyl transferase, and CAAX proteases as well as antisense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

This invention further relates to a method for using the compounds or pharmaceutical composition in combination with other tumor treatment approaches, including surgery, ionizing radiation, photodynamic therapy, or implants, e.g., with corticosteroids, hormones, or used as radiosensitizers.

One such approach may be, for example, radiation therapy in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

Photodynamic therapy includes therapy which uses certain chemicals known as photosensitizing compounds to treat or prevent cancers. Examples of photodynamic therapy include treatment with compounds, such as e.g., VISUDYNE and porfimer sodium. Angiostatic steroids include compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids include compounds, such as e.g., fluocinolone and dexamethasone. Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds or pharmaceutical compositions of the present invention can be used in combination with an amount of one or more substances selected from anti-angiogenesis agents, signal transduction inhibitors, and antiproliferative agents.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780, 386 (published Jun. 25, 1997), all of which are incorporated herein in their entireties by reference. In some embodiments, MMP-2 and MMP-9 inhibitors have little or no activity inhibiting MMP-1, or selectively inhibit MMP-2 and/or AMP-9 relative to the other matrix-metalloproteinases (i. e., MAP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, and RS 13-0830.

The invention also relates to a method of and to a pharmaceutical composition of treating a cardiovascular disease in a mammal which comprises an amount of a compound of the present invention, or a pharmaceutically acceptable salt, ester, prodrug, solvate, hydrate or derivative thereof, or an isotopically-labeled derivative thereof, and an amount of one or more therapeutic agents use for the treatment of cardiovascular diseases.

Exemplary agents for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

The compounds describe herein may be formulated or administered in conjunction with liquid or solid tissue barriers also known as lubricants. Examples of tissue barriers include, but are not limited to, polysaccharides, polyglycans, seprafilm, intercede and hyaluronic acid.

Medicaments which may be administered in conjunction with the compounds described herein include any suitable drugs usefully delivered by inhalation for example, analgesics, e.g., codeine, dihydromorphine, ergotamine, fentanyl or morphine; anginal preparations, e.g., diltiazem; antiallergics, e.g., cromoglycate, ketotifen or nedocromil; anti-infectives, e.g., cephalosporins, penicillins, streptomycin, sulphonamides, tetracyclines or pentamidine; antihistamines, e.g., methapyrilene; anti-inflammatories, e.g., beclomethasone, flunisolide, budesonide, tipredane, triamcinolone acetonide or fluticasone; antitussives, e.g., noscapine; bronchodilators, e.g., ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g., amiloride; anticholinergics e.g., ipratropium, atropine or oxitropium; hormones, e.g., cortisone, hydrocortisone or prednisolone; xanthines e.g., aminophylline, choline theophyllinate, lysine theophyllinate or theophylline; and therapeutic proteins and peptides, e.g., insulin or glucagon. It will be clear to a person skilled in the art that, where appropriate, the medicaments may be used in the form of salts (e.g., as alkali metal or amine salts or as acid addition salts) or as esters (e.g., lower alkyl esters) or as solvates (e.g., hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-Lactam antibiotics, an agent comprising an aminoglycoside, protein synthesis inhibitors, drugs used in the chemotherapy of tuberculosis, *mycobacterium avium* complex disease, and leprosy, antifungal agents, antiviral agents including nonretroviral agents and antiretroviral agents.

Examples of therapeutic antibodies that can be combined with a subject compound include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

Further therapeutic agents that can be combined with a subject compound may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the compounds of the invention will be co-administer with other agents as described above. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the present invention and any of the agents described above can be simultaneously administered, wherein both the agents are present in separate formulations. In another alternative, a compound of the present invention can be administered just followed by and any of the agents described above, or vice versa. In the separate administration protocol, a compound of the present invention and any of the agents described above may be administered a few minutes apart, or a few hours apart, or a few days apart.

Administration of the compounds of the present invention can be effected by any method that enables delivery of the compounds to the site of action. An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

The amount of the compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g., by dividing such larger doses into several small doses for administration throughout the day.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

When a compound of the invention, is administered in a composition that comprises one or more agents, and the agent has a shorter half-life than the compound of the invention unit dose forms of the agent and the compound of the invention may be adjusted accordingly.

In some embodiments, compounds of the invention are tested to estimate pharmacokinetic properties and expected side effect profile. Various assays are known in the art for this purpose. For example, oral availability can be estimated during early stages of drug development by performing a Caco-2 permeability assay. Further, oral pharmacokinetics in humans can be approximated by extrapolating from the results of assays in mice, rats or monkey. In some embodiments, compounds of the invention show good oral availability across multiple species of organisms.

Other assays examine the effect of a drug candidate on liver function and metabolism. Cytochrome P450 (CYP) proteins are the main enzyme involved in metabolizing drugs administered to mammalian organisms. As such, undesired interaction of a drug candidate can be a significant source of adverse drug interactions. Generally, it is desirable for a drug to not interact with CYP isozymes such as CYP1A2, CYP2C9, CYP2C19, CYP2D6, or CYP3A4. In some embodiments, a compound of the invention exhibits an IC50 of greater than 10 µM for CYP1A2, CYP2C9, CYP2C19, CYP2D6, or CYP3A4. Additionally, liver microsome and hepatocyte metabolism assays using human preparations can be used to estimate the in-vitro half life of a drug candidate.

Cardiac toxicity is also an important consideration in evaluating drug candidates. For example, hERG is the gene coding for the Kv11.1 potassium ion channel, a protein is involved in mediating repolarizing current in the cardiac action potential in the heart. Inhibition of the hERG gene product by a drug candidate can lead to an increase in the risk of sudden death and is therefore an undesirable property. In some embodiments, a compound of the invention exhibits less than 10% hERG inhibition when administered at a suitable concentration.

Mutagenicity of drug candidate compounds can be assayed via an Ames test or a modified Ames test using e.g., the liver S9 system. In some embodiments, compounds of the invention show negative activity in such a test.

Other undesired interactions of a drug candidate can also be ascertained via a receptor panel screen. In some embodiments, no significant interactions are detected for compounds of the invention.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

Example 1

Synthesis of 5-(7-(3-(4-isopropylpiperazin-1-yl)azetidin-1-yl)-1,5-naphthyridin-2-yl)benzo[d]oxazol-2-amine Example 1a Synthesis of 3-bromo-1,5-naphthyridine (C-2)

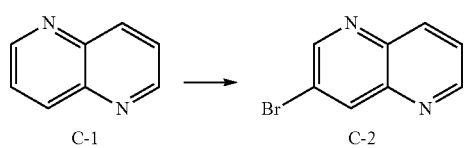

To a stirred mixture of 1,5-naphthyridine (C-1) (50.0 g, 384 mmol, 1.0 eq) and sodium acetate (62.9 g, 768 mmol, 2.0 eq) in acetic acid (300 mL) at 80° C., a solution of bromine (67.5 g, 422 mmol, 1.1 eq) in acetic acid (80 mL) was added dropwise while keeping the reaction temperature at 80° C. to 90° C. After stirring for 2 h at 80° C., the reaction was complete based on TLC analysis. The resulting mixture was cooled to RT and then filtered. The filtrate was concentrated in vacuo and the residue was purified by flash column chromatography on silica gel (0-30% ethyl acetate-petroether) to afford the desired product 3-bromo-1,5-naphthyridine (C-2) (36.5 g, 45% yield) as a pale yellow solid. $^1$H NMR (300

MHz, CDCl$_3$-d6) δ: 8.97 (m, 2H), 8.57 (s, 1H), 8.37 (d, J=8.4 Hz, 1H), 7.65 (m, 1H); ESI-MS m/z: 208.96 [M+H]$^+$.

Example 1b

Synthesis of 3-bromo-1,5-naphthyridine-5-oxide (C-3)

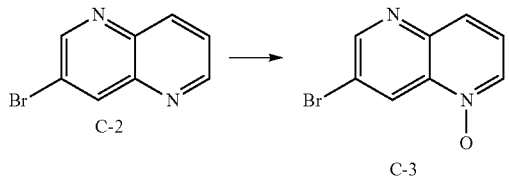

To a stirred solution of 3-bromo-1,5-naphthyridine (C-2) (35.6 g, 170 mmol, 1.0 eq) in dichloromethane (300 mL) at 0° C. was added m-chloroperbenzoic acid (35.27 g, 204 mmol, 1.2 eq) in portions. The resulting mixture was stirred for 1 h at RT. The reaction was complete based on TLC analysis. The reaction mixture was washed with saturated Na$_2$SO$_3$ solution and saturated NaHCO$_3$ solution sequentially, and then washed with brine, dried over Na$_2$SO$_4$ and filtered. The filtrate was concentrated in vacuo and the residue was purified by column chromatography on silica gel (1-5% MeOH-DCM) to afford the desired product 3-bromo-1,5-naphthyridine-5-oxide (C-3) (28.35 g, 74% yield). $^1$H NMR (300 MHz, CDCl$_3$-d6) δ: 9.21 (s, 1H), 9.01 (s, 1H), 8.52 (d, J=6.3 Hz, 1H), 7.96 (d, J=8.7 Hz, 1H), 7.53 (m, 1H); ESI-MS m/z: 208.10 [M+H]$^+$.

Example 1c

Synthesis of 7-bromo-1,5-naphthyridin-2(1H)-one (C-4)

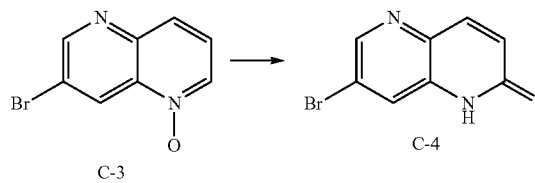

To a mixture of 3-bromo-1,5-naphthyridine-5-oxide (C-3) (70.0 g, 311 mmol, 1.0 eq) and 4-toluolsulfonyl chloride (71.16 g, 373 mmol, 1.2 eq) in CHCl$_3$ (1200 mL) was added a solution of potassium carbonate (146 g, 1056 mmol, 3.4 eq) in H$_2$O (500 mL) at RT. The resulting mixture was stirred overnight and diluted with H$_2$O (500 mL). The solid was collected by filtration, washed with water, dried in vacuo to afford the desired product 7-bromo-1,5-naphthyridin-2(1H)-one (C-4) (28.8 g, 41.2% yield). $^1$H NMR (300 MHz, DMSO-d6) δ: 11.90 (bs, 1H), 8.51 (s, 1H), 7.88 (d, J=9.6 Hz, 1H), 7.81 (s, 1H), 6.74 (d, J=9.6 Hz, 1H); ESI-MS m/z: 225.1 [M+H]$^+$.

Example 1d

Synthesis of 1-(4-methoxybenzyl)-7-bromo-1,5-naphthyridin-2(1H)-one (C-5)

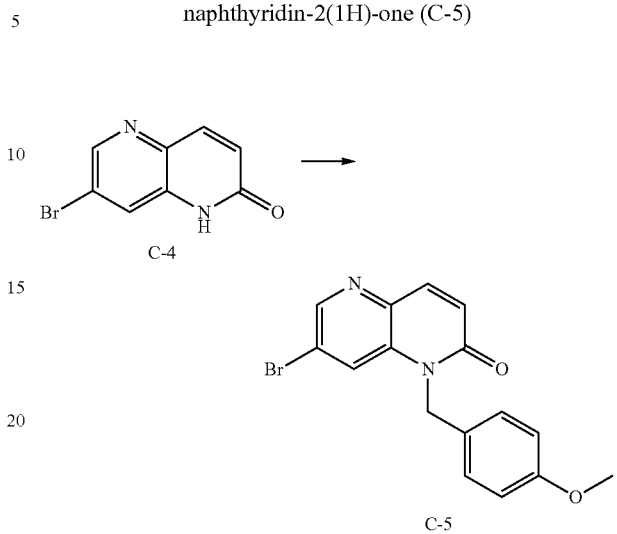

To a stirred solution of 7-bromo-1,5-naphthyridin-2(1H)-one (C-4) (29 g, 128.9 mmol, 1.0 eq) in DMF (200 mL) was added sodium hydride (60% in mineral oil, 7.73 g, 193.3 mmol, 1.5 eq) in portions at RT, the mixture was stirred at 30 to 40° C. for 1 h. 1-(Chloromethyl)-4-methoxybenzene (30.28 g, 193.3 mmol, 1.5 eq) was added dropwise. The resulting mixture was stirred at 30 to 40° C. overnight and quenched with water (500 mL) and extracted with ethyl acetate (5×200 mL). The combined organic layers were washed with brine, dried over Na$_2$SO$_4$ and filtered. The filtrate was concentrated in vacuo and the residue was purified by flash column chromatography on silica gel (10-50% ethyl acetate/petroether) to afford the desired product, 1-(4-methoxybenzyl)-7-bromo-1,5-naphthyridin-2(1H)-one (C-5) (20.2 g, 45.4% yield) as a white solid. $^1$H NMR (400 MHz, DMSO-d6) δ: 8.61 (s, 1H), 8.15 (s, 1H), 8.00 (d, J=10 Hz, 1H), 7.18 (d, J=8.4 Hz, 2H), 7.02 (d, J=9.6 Hz, 1H), 6.89 (d, J=8.8 Hz, 2H), 5.45 (s, 2H), 3.71 (s, 3H); ESI-MS m/z: 345.1 [M+H]$^+$.

Example 1e

Synthesis of 1-(4-methoxybenzyl)-7-(3-hydroxyazetidin-1-yl)-1,5-naphthyridin-2(1H)-one (C-6)

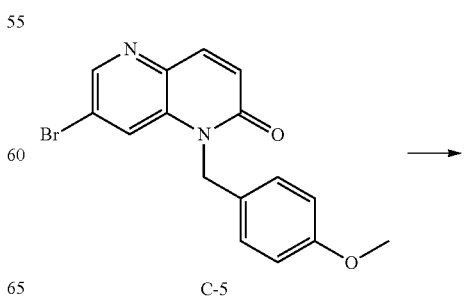

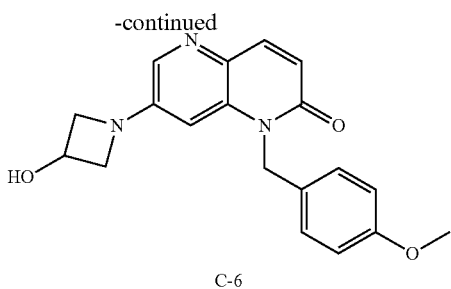

C-6

A mixture of 1-(4-methoxybenzyl)-7-bromo-1,5-naphthyridin-2(1H)-one (C-5) (8.1 g, 23.46 mmol, 1.0 eq), azetidin-3-ol hydrochloride (3.08 g, 28.15 mmol, 1.2 eq), Pd$_2$(dba)$_3$ (429 mg, 0.47 mmol, 0.02 eq), Xantphos (407 mg, 0.7 mmol, 0.03 eq) and Cs$_2$CO$_3$ (19.87 g, 61 mmol, 2.6 eq) in 1,4-dioxane (100 mL) was heated at reflux temperature under argon atmosphere overnight then cooled and filtered, the filter cake was washed with ethyl acetate and the combined filtrate was concentrated in vacuo and the residue was purified by column chromatography on silica gel (1-5% MeOH-DCM) to afford 1-(4-methoxybenzyl)-7-(3-hydroxyazetidin-1-yl)-1,5-naphthyridin-2(1H)-one (C-6) (7.2 g, 91% yield). $^1$H NMR (300 MHz, DMSO-d6) δ: 7.76 (m, 2H), 7.17 (d, J=8.7 Hz, 2H), 6.84 (d, J=8.7 Hz, 2H), 8.53 (m, 2H), 5.68 (d, J=6.3 Hz, 1H), 5.34 (s, 2H), 4.56 (m, 1H), 4.13 (m, 2H), 3.66 (s, 3H), 3.59 (m, 2H); ESI-MS m/z: 338.1 [M+H]$^+$.

Example 1f

Synthesis of 1-(4-methoxybenzyl)-7-(3-oxoazetidin-1-yl)-1,5-naphthyridin-2(1H)-one (C-7)

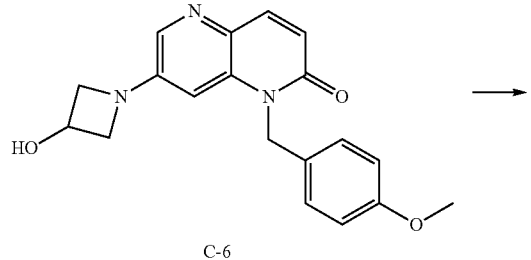

C-6

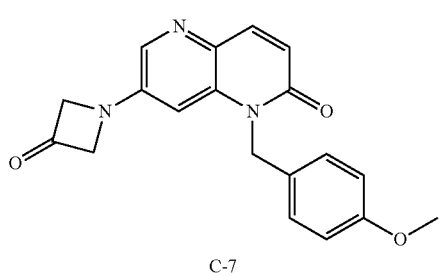

C-7

To a mixture of 1-(4-methoxybenzyl)-7-(3-hydroxyazetidin-1-yl)-1,5-naphthyridin-2(1H)-one (C-6) (2.637 g, 7.81 mmol, 1.0 eq) in DMSO (30 mL) was added Et$_3$N (9 mL, 64.82 mmol, 8.3 eq) and a solution of pyridine sulfur trioxide (8.71 g, 54.7 mmol, 7.0 eq) in DMSO (30 mL) sequentially. The resulting mixture was stirred at RT for 1 h. The reaction was complete based on TLC analysis. The mixture was poured into ice-water (100 mL) and extracted with ethyl acetate (3×50 mL). The combined organic layers were washed with brine, dried over Na$_2$SO$_4$ and filtered. The filtrate was concentrated in vacuo and the residue was purified by flash column chromatography on silica gel (1:1 to 1:3 petroether/ethyl acetate and then 80:1DCM/MeOH) to afford the desired product 1-(4-methoxybenzyl)-7-(3-oxoazetidin-1-yl)-1,5-naphthyridin-2(1H)-one (C-7) (2.6 g, 99% yield) as a pale solid. HNMR (300 MHz, DMSO-d6) δ: 7.93 (s, 1H), 7.82 (d, J=9.6 Hz, 1H), 7.21 (d, J=9 Hz, 2H), 6.84 (m, 3H), 6.60 (d, J=9.6 Hz, 1H), 5.37 (s, 2H), 4.79 (s, 4H), 3.65 (s, 3H); ESI-MS m/z: 336.1 [M+H]$^+$.

Example 1g

Synthesis of 1-(4-methoxybenzyl)-7-(3-(4-isopropylpiperazin-1-yl)azetidin-1-yl)-1,5-naphthyridin-2(1H)-one (C-8)

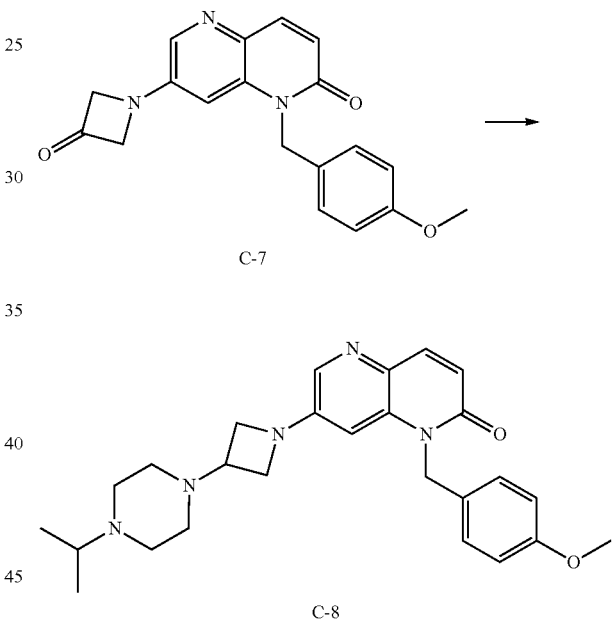

C-7

C-8

A mixture of 1-(4-methoxybenzyl)-7-(3-oxoazetidin-1-yl)-1,5-naphthyridin-2(1H)-one (C-7) (5.796 g, 17.3 mmol, 1.0 eq) and 1-isopropylpiperazine (4.432 g, 34.6 mmol, 2.0 eq) in DCM (150 mL) and acetic acid (0.5 mL) was heated at reflux temperature for 3 h, then NaBH(OAc)$_3$ (7.33 g, 34.6 mmol, 2.0 eq) was added in portions and the resulting mixture was kept reflux overnight. The reactant mixture was cooled and diluted with H$_2$O (300 mL) and extracted with DCM (4×100 mL). The combined organic layers were washed with brine, dried over Na$_2$SO$_4$ and filtered. The filtrate was concentrated in vacuo and the residue was purified by flash column chromatography on silica gel (2-5% MeOH-DCM) to afford the desired product 1-(4-methoxybenzyl)-7-(3-(4-isopropylpiperazin-1-yl)azetidin-1-yl)-1,5-naphthyridin-2(1H)-one (C-8) (5.6 g, 72.3% yield) as a pale solid. $^1$H NMR (300 MHz, CDCl$_3$-d6) δ: 7.83 (d, J=7.5 Hz, 1H), 7.78 (s, 1H), 7.15 (d, J=6.9 Hz, 2H), 6.85 (d, J=6.6 Hz, 2H), 6.72 (d, J=7.2 Hz, 1H), 6.37 (s, 1H), 5.40 (s, 2H), 4.02 (m, 2H), 3.78 (m, 5H), 3.67 (m, 1H), 3.51 (m, 1H), 3.42 (m, 1H), 2.97 (m, 1H), 2.80 (m, 4H), 2.55 (m, 2H), 1.17 (d, J=4.8 Hz, 6H); ESI-MS m/z: 448.3 [M+H]⁺.

Example 1h

Synthesis of 7-(3-(4-isopropylpiperazin-1-yl)azetidin-1-yl)-1,5-naphthyridin-2(1H)-one (C-9)

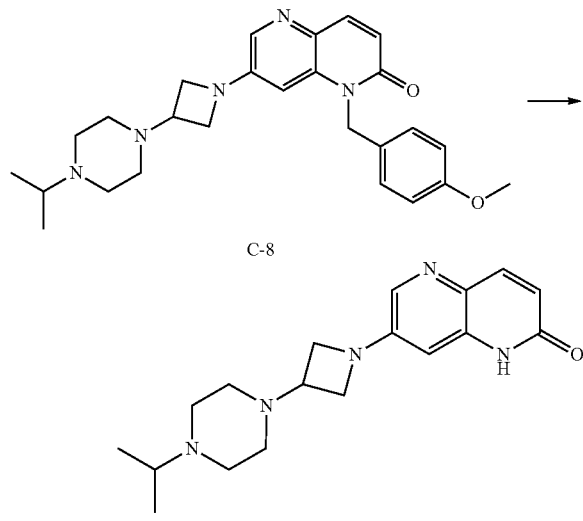

1-(4-methoxybenzyl)-7-(3-(4-isopropylpiperazin-1-yl)azetidin-1-yl)-1,5-naphthyridin-2(1H)-one (C-8) (5.6 g, 12.5 mmol, 1.0 eq) was dissolved in TFA (100 mL) and the resulting mixture was stirred at reflux for 16 h. The reaction was complete based on TLC analysis. The mixture was cooled to RT and concentrated in vacuo to remove TFA. The resulting suspension was diluted with water (200 mL) and neutralized with sodium carbonate to adjust the pH value to 8-9 while keeping the temperature below 0° C. The resulting mixture was stirred at RT for 30 min. The solid was collected by filtration, rinsed with water (2×50 mL) and dried in vacuo to afford the desired product 7-(3-(4-isopropylpiperazin-1-yl) azetidin-1-yl)-1,5-naphthyridin-2(1H)-one (C-9) (3.91 g, 95.7% yield) as a white solid. ESI-MS m/z: 328.2 [M+H]⁺.

Example 1i

Synthesis of 2-chloro-7-(3-(4-isopropylpiperazin-1-yl)azetidin-1-yl)-1,5-naphthyridine (C-10)

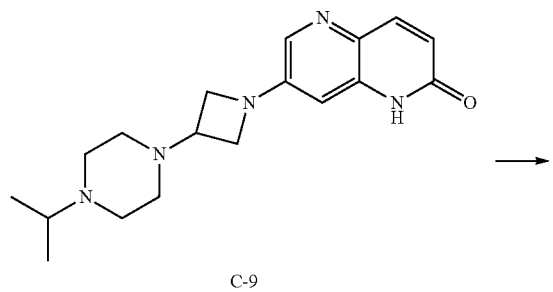

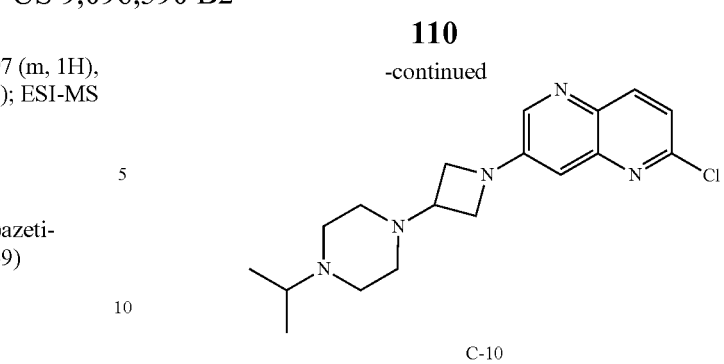

7-(3-(4-isopropylpiperazin-1-yl)azetidin-1-yl)-1,5-naphthyridin-2(1H)-one (C-9) (5.346 g, 16.3 mmol, 1.0 eq) was dissolved in POCl₃ (100 mL) and the resulting mixture was stirred at reflux for 30 min. The reaction was complete based on TLC analysis. Then the mixture was cooled to RT and concentrated in vacuo to remove POCl₃. The residue was poured into ice water (500 mL) and neutralized with saturated aqueous Na₂CO₃ solution to adjust the pH value to 8-9 while keeping the temperature below 0° C. The mixture was stirred at RT for 30 min. The residue was extracted with DCM (4×200 mL) and the combined organic layers were washed with brine, dried over Na₂SO₄ and filtered. The filtrate was concentrated in vacuo and the residue was purified by flash column chromatography on silica gel (2-7% MeOH-DCM) to afford the desired product 2-chloro-7-(3-(4-isopropylpiperazin-1-yl)azetidin-1-yl)-1,5-naphthyridine (C-10) (1.9 g, 33.7% yield). ESI-MS m/z: 346.14 [M+H]⁺.

Example 1j

Synthesis of 5-(7-(3-(4-isopropylpiperazin-1-yl)azetidin-1-yl)-1,5-naphthyridin-2-yl)benzo[d]oxazol-2-amine (72)

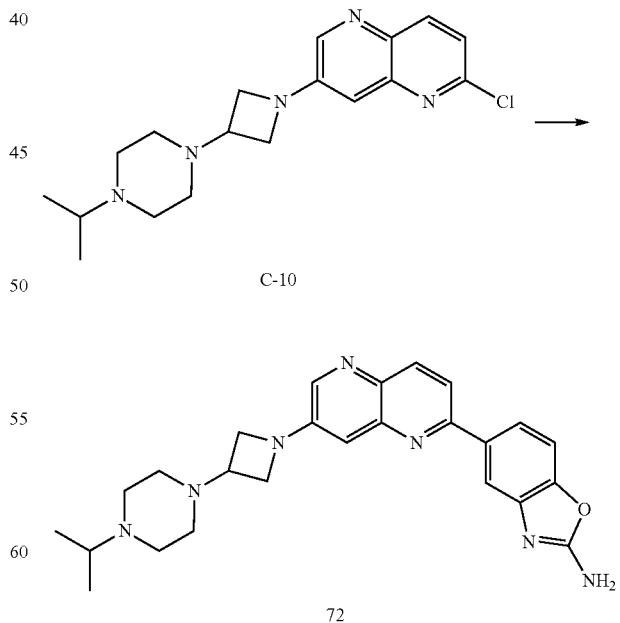

A mixture of 2-chloro-7-(3-(4-isopropylpiperazin-1-yl) azetidin-1-yl)-1,5-naphthyridine (C-10) (220 mg, 0.636 mmol, 1.0 eq), 2-aminobenzo[d]oxazol-5-ylboronic acid (135 mg, 0.763 mmol, 1.2 eq), Pd(PPh$_3$)$_4$ (73 mg, 0.06 mmol, 0.1 eq), and Na$_2$CO$_3$ (202 mg, 1.908 mmol, 3.0 eq) were dissolved in a mixture of 1,4-dioxane (30 mL) and water (9 mL). The resulting mixture was degassed and back-filled with argon three times and heated at reflux under an argon atmosphere for 2 h. The reaction was complete based on TLC analysis. The mixture was concentrated in vacuo and the residue was purified by column chromatography on silica gel (1:5 MeOH-DCM) to afford the desired product 5-(7-(3-(4-isopropylpiperazin-1-yl)azetidin-1-yl)-1,5-naphthyridin-2-yl)benzo[d]oxazol-2-amine (72) (120 mg, 42.5% yield). $^1$H NMR (300 MHz, DMSO-d6) δ: 8.35 (s, 1H), 8.20 (d, J=8.7 Hz, 1H), 8.02 (s, 1H), 7.98 (d, J=8.4 Hz, 1H), 7.87 (d, J=6.3 Hz, 1H), 7.48 (s, 2H), 7.42 (d, J=8.1 Hz, 1H), 7.08 (s, 1H), 4.12 (m, 2H), 3.85 (m, 2H), 3.36 (m, 1H), 3.23 (m, 4H), 2.47 (m, 1H), 2.37 (m, 4H), 0.95 (d, J=6.9 Hz, 6H); ESI-MS m/z: 444.21 [M+H]$^+$.

Example 2

Synthesis of 2-amino-1-(4-(6-(2-aminobenzo[d]oxazol-5-yl)-1,5-naphthyridin-3-yl)piperazin-1-yl)-2-methylpropan-1-one

Example 2a

Synthesis of tert-butyl 1,5-naphthyridin-3-ylcarbamate (D-12)

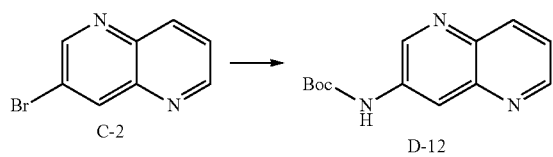

To a solution of 3-bromo-1,5-naphthyridine (C-2) (4.181 g, 20.0 mmol, 1.0 eq) in 1,4-dioxane (100 mL), tert-butylcarbamate (2.812 g, 24.0 mmol, 1.2 eq), cesium carbonate (9.132 g, 28.0 mmol, 1.4 eq), tris(benzylideneacetone)dipalladium (183 mg, 0.20 mmol, 0.01 eq) and Xantphos (347 mg, 0.60 mmol, 0.03 eq) were added. The mixture was heated at reflux for 16 h under an argon atmosphere. After the reaction mixture was cooled to RT, it was diluted with water (300 mL) and extracted with ethyl acetate (3×100 mL). The combined organic layers were washed with brine (200 mL), dried over Na$_2$SO$_4$ and filtered. The filtrate was concentrated in vacuo. The resultant residue was purified by silica gel column chromatography (15-25% ethyl acetate-petroether) to afford the desired product, tert-butyl 1,5-naphthyridin-3-ylcarbamate (D-12) (4.047 g, 82.5% yield) as a yellow oil. $^1$H NMR (300 MHz, DMSO-d6) δ: 10.02 (bs, 1H), 8.94 (s, 1H), 8.87 (m, 1H), 8.47 (s, 1H), 8.28 (d, J=8.4 Hz, 1H), 7.58 (m, 1H), 1.49 (s, 9H); ESI-MS m/z: 246.10 [M+H]$^+$

Example 2b

Synthesis of 1,5-naphthyridin-3-amine (D-13)

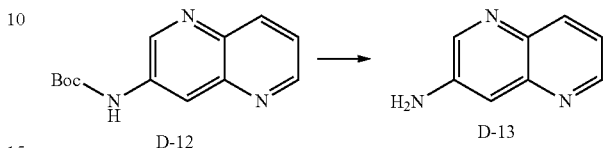

To a solution of tert-butyl 1,5-naphthyridin-3-ylcarbamate (D-12) (4.040 g, 16.5 mmol, 1.0 eq) in methanol (24 mL), concentrated hydrochloric acid (36.5%, 10 mL, 120 mmol, 7.27 eq) was added. The resulting mixture was stirred at 50° C. for 2 h. The reaction was complete based on TLC analysis. The mixture was concentrated under reduced pressure to afford the desired product 1,5-naphthyridin-3-amine (D-13), which was used for next reaction without further purification. $^1$HNMR (300 MHz, DMSO-d6) 8.85 (m, 1H), 8.77-8.75 (m, 2H), 7.63-7.69 (m, 1H), 7.4 (d, J=1.8 Hz, 1H); ESI-MS m/z: 146.10 [M+H]$^+$.

Example 2c

Synthesis of 3-iodo-1,5-naphthyridine (D-14)

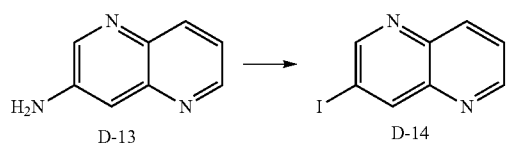

To a solution of 1,5-naphthyridin-3-amine (D-13) (16.5 mmol, 1.0 eq) in H$_2$O (150 mL), con. HCl (36.5%, 7 mL, 84 mmol, 5.0 eq) was added slowly at 0-5° C. The resulting mixture was stirred for 15 min at 0-5° C., a solution of sodium nitrite (1.252 g, 18.1 mmol, 1.1 eq) in H$_2$O (5 mL) was added dropwise at 0-5° C. and stirred for 1 h. Then the above solution was added to a solution of KI (8.217 g, 49.5 mmol, 3 eq) in H$_2$O (100 mL), the resulting mixture was stirred at 60° C. for 1 hour. After the solution was cooled to RT, solid Na$_2$SO$_3$ (4.0 g) was added. The mixture was neutralized with solid Na$_2$CO$_3$ to adjust pH value to 7-8, and extracted with ethyl acetate (3×100 mL). The combined organic layers were dried over Na$_2$SO$_4$ and filtered. The filtrate was concentrated in vacuo to afford the desired product 3-iodo-1,5-naphthyridine (D-14) (2.758 g, 65.3% yield, 2 steps) as a solid. $^1$H NMR (300 MHz, CDCl3-d6) δ: 9.1 (d, J=2.1 Hz, 1H), 8.95

(dd, J=4.2 Hz, J=1.5 Hz, 1H), 8.80 (d, J=1.2 Hz, 1H), 8.35 (d, J=8.4 Hz, 1H), 7.63-7.67 (m, 1H); ESI-MS m/z: 256.96 [M+H]$^+$.

Example 2d

Synthesis of 7-iodo-1,5-naphthyridine 1-oxide (D-15)

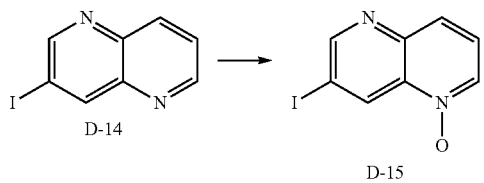

To a solution of 3-iodo-1,5-naphthyridine (D-14) (2.750 g, 10.7 mmol, 1.0 eq) in CH$_2$Cl$_2$ (30 mL), 3-chloroperoxybenzoic acid (2.780 g, 16.1 mmol, 1.5 eq) was added. After the resulting mixture was stirred at RT for 2 h, saturated sodium carbonate solution (50 mL) was added, and extracted with CH$_2$Cl$_2$ (10×30 mL). The combined organic layers were dried over Na$_2$SO$_4$ and filtered. The filtrate was concentrated in vacuo. The resultant residue was purified by silica gel column chromatography (50% EA-PE) to afford the desired product 7-iodo-1,5-naphthyridine 1-oxide (D-15) (1.574 g, 54% yield) as a solid. $^1$H NMR (400 MHz, CDCl$_3$-d6) δ: 9.45 (dd, J=2.0 Hz, J=0.8 Hz, 1H), 9.18 (d, J=2.5 Hz, 1H), 8.54 (d, J=6.0 Hz, 1H), 7.98 (d, J=8.8 Hz, 1H), 7.59-7.55 (m, 1H); ESI-MS m/z: 272.95 [M+H]$^+$.

Example 2e

Synthesis of 7-iodo-1,5-naphthyridin-2(1H)-one (D-16)

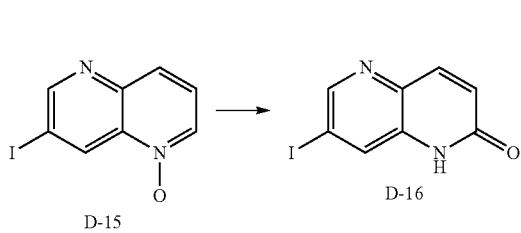

To a solution of 7-iodo-1,5-naphthyridine 1-oxide (D-15) (1.570 g, 5.77 mmol, 1.0 eq) in chloroform (30 mL), p-toluenesulfonyl chloride (1.210 g, 6.35 mmol, 1.1 eq), potassium carbonate (2.711 g, 19.5 mmol, 3.4 eq) and water (10 mL) were added. After stirring at RT for 16 h, the reaction mixture was diluted with water (50 mL), filtered to obtain the desired product 7-iodo-1,5-naphthyridin-2(1H)-one (D-16) (740 mg, 47.1%) as a white solid. $^1$H NMR (300 MHz, DMSO-d6) δ: 8.60 (s, 1H), 7.98 (d, J=1.8 Hz, 1H), 7.85 (d, J=9.9 Hz, 1H), 6.72 (d, J=9.9 Hz, 1H); ESI-MS m/z: 272.97 [M+H]$^+$.

Example 2f

Synthesis of 2-chloro-7-iodo-1,5-naphthyridine (D-17)

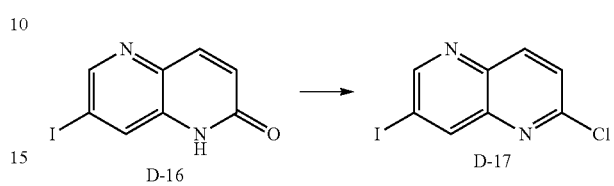

7-iodo-1,5-naphthyridin-2(1H)-one (D-16) (740 mg, 2.72 mmol, 1.0 eq) was dissolved in POCl$_3$ (10 mL), and then heated at reflux for 1 h. The reaction was complete based on TLC analysis. The reaction mixture was concentrated in vacuo, poured into ice-water (30 mL), and neutralized with saturated sodium carbonate solution (about 30 mL) to adjust pH value to 8-9. The mixture was extracted with ethyl acetate (3×30 mL). The combined organic layer was washed with brine (50 mL), dried over Na$_2$SO$_4$ and filtered. The filtrate was concentrated in vacuo. The resultant residue was purified by silica gel column chromatography (5-10% ethyl acetate/petroether) to afford the desired product, 2-chloro-7-iodo-1,5-naphthyridine (D-17) (715 mg, 90.5%) as a solid. $^1$H NMR (400 MHz, CDCl$_3$-d6) δ: 9.13 (d, J=2.0 Hz, 1H), 8.74 (d, J=1.6 Hz, 1H), 8.33 (d, J=8.8 Hz, 1H), 7.66 (d, J=8.8 Hz, 1H); ESI-MS m/z: 290.93 [M+H]$^+$.

Example 2g

Synthesis of tert-butyl 4-(6-chloro-1,5-naphthyridin-3-yl)piperazine-1-carboxylate (D-18)

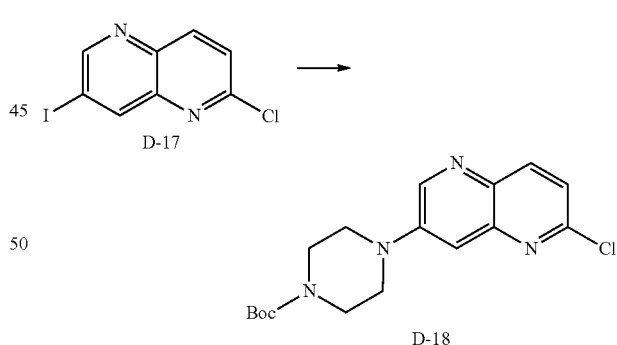

To a solution of 2-chloro-7-iodo-1,5-naphthyridine (D-17) (586 mg, 2.02 mmol, 1.0 eq) in 1,4-dioxane (20 mL), tert-butyl piperazine-1-carboxylate (372 mg, 2.00 mmol, 1.0 eq), cesium carbonate (922 mg, 2.83 mmol, 1.4 eq), tris(benzylideneacetone)dipalladium (37 mg, 0.04 mmol, 0.02 eq) and Xantphos (35 mg, 0.06 mmol, 0.03 eq) were added. The mixture was stirred at reflux for 16 h under an argon atmosphere. After the reaction mixture was cooled to RT, it was diluted with water (50 mL) and extracted with ethyl acetate (3×50 mL). The combined organic layer was washed with brine (50 mL), dried over Na$_2$SO$_4$ and filtered. The filtrate was concentrated in vacuo. The resultant residue was purified by silica gel column chromatography (15% ethyl acetate/petroether) to afford the desired product, tert-butyl 4-(6-chloro-1,5-naphthyridin-3-yl)piperazine-1-carboxylate (D-18) (207 mg, 29.4% yield) as a yellow oil. $^1$H NMR (300 MHz, CDCl$_3$-d6) δ: 8.79 (d, J=2.7 Hz, 1H), 8.16 (d, J=8.7 Hz, 1H), 7.43 (d, J=2.7 Hz, 1H), 7.36 (d, J=8.7 Hz, 1H), 3.64 (m, 4H), 3.34 (m, 4H), 1.49 (s, 9H); ESI-MS m/z: 349.13[M+H]$^+$.

Example 2h

Synthesis of 2-chloro-7-(piperazin-1-yl)-1,5-naphthyridine (D-19)

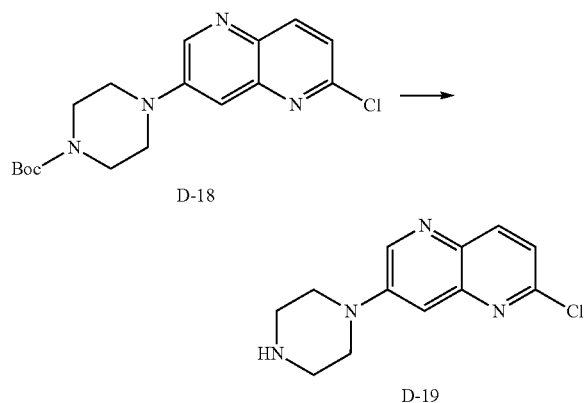

Acetyl chloride (4.3 mL, 60.5 mmol) was added to MeOH (11 mL) at 0° C., the resulting solution was stirred at 0° C. for 30 min. To this solution, tert-butyl 4-(6-chloro-1,5-naphthyridin-3-yl)piperazine-1-carboxylate (D-18) (207 mg, 0.59 mmol, 1.0 eq) was added, and the mixture was stirred at RT for 2 h. The reaction was complete based on TLC analysis. The mixture was concentrated in vacuo to afford the desired product 2-chloro-7-(piperazin-1-yl)-1,5-naphthyridine (D-19), which was used for next reaction without further purification. $^1$H NMR (300 MHz, DMSO-d6) δ: 8.99 (d, J=2.7 Hz, 1H), 8.28 (d, J=8.7 Hz, 1H), 7.59 (d, J=2.7 Hz, 1H), 7.52 (d, J=8.7 Hz, 1H), 3.68 (m, 4H), 3.22 (m, 4H); ESI-MS m/z: 249.06[M+H]$^+$.

Example 2i

Synthesis of tert-butyl(1-(4-(6-chloro-1,5-naphthyridin-3-yl)piperazin-1-yl)-2-methyl-1-oxopropan-2-yl)carbamate (D-20)

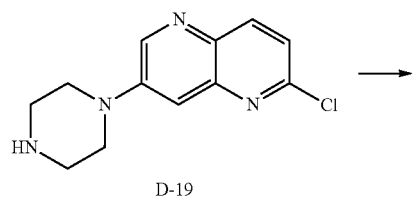

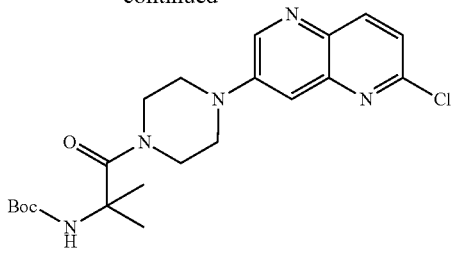

To a stirred mixture of 2-((tert-butoxycarbonyl)amino)-2-methylpropanoic acid (180 mg, 0.89 mmol, 1.5 eq), triethylamine (209 mg, 2.07 mmol, 3.5 eq) and HOBt (120 mg, 0.89 mmol, 1.5 eq) in anhydrous CH$_2$Cl$_2$ (10 mL), EDCI (170 mg, 0.89 mmol, 1.5 eq) was added. The resulting mixture was stirred at RT for 30 min, and then 2-chloro-7-(piperazin-1-yl)-1,5-naphthyridine (D-19) (0.59 mmol, 1.0 eq) was added. The reaction mixture was stirred at RT for 20 h, and then quenched with water (30 mL) and CH$_2$Cl$_2$ (15 mL), and the organic layer was separated. The organic layer was washed with brine (10 mL), dried over anhydrous Na$_2$SO$_4$ and filtered. The filtrate was concentrated in vacuo. The resultant residue was purified by silica gel column chromatography (2% MeOH—CH$_2$Cl$_2$) to afford the desired product, tert-butyl(1-(4-(6-chloro-1,5-naphthyridin-3-yl)piperazin-1-yl)-2-methyl-1-oxopropan-2-yl)carbamate (D-20) (193 mg, 75.4% yield, 2 steps). ESI-MS m/z: 434.18[M+H]$^+$.

Example 2j

Synthesis of tert-butyl(1-(4-(6-(2-aminobenzo[d]oxazol-5-yl)-1,5-naphthyridin-3-yl)piperazin-1-yl)-2-methyl-1-oxopropan-2-yl)carbamate (D-21)

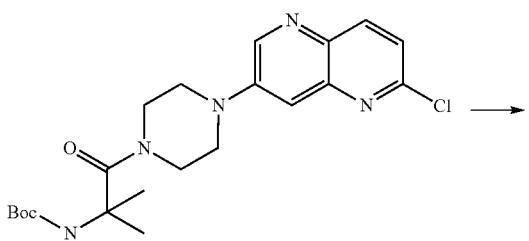

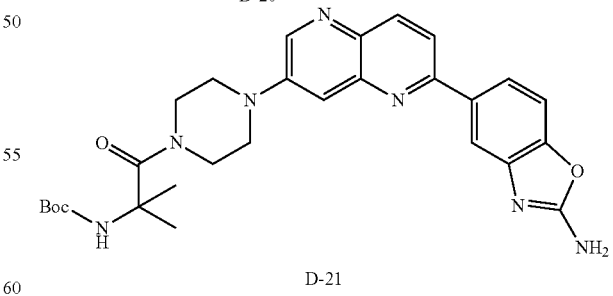

Tert-butyl(1-(4-(6-chloro-1,5-naphthyridin-3-yl)piperazin-1-yl)-2-methyl-1-oxopropan-2-yl)carbamate (20) (190 mg, 0.44 mmol, 1.0 eq) and (2-aminobenzo[d]oxazol-5-yl) boronic acid (94 mg, 0.53 mmol, 1.2 eq) were dissolved in a mixture of 1,4-dioxane (10 mL) and water (10 mL). To this mixture, Pd(PPh$_3$)$_4$ (51 mg, 0.044 mmol, 0.1 eq) and sodium carbonate (140 mg, 1.32 mmol, 3.0 eq) were added sequentially. The resulting mixture was heated at reflux for 2 h with stirring under an argon atmosphere. The reaction was complete based on TLC analysis. The reaction mixture was concentrate in vacuo, and purified by silica gel column chromatography (1-5% MeOH—CH$_2$Cl$_2$) to afford the desired product, tert-butyl(1-(4-(6-(2-aminobenzo[d]oxazol-5-yl)-1,5-naphthyridin-3-yl)piperazin-1-yl)-2-methyl-1-oxopropan-2-yl)carbamate (D-21) (87 mg, 37.2%) as a yellow solid. ESI-MS m/z: 532.22[M+H]$^+$.

Example 2k

Synthesis of 2-amino-1-(4-(6-(2-aminobenzo[d]oxazol-5-yl)-1,5-naphthyridin-3-yl)piperazin-1-yl)-2-methylpropan-1-one (43)

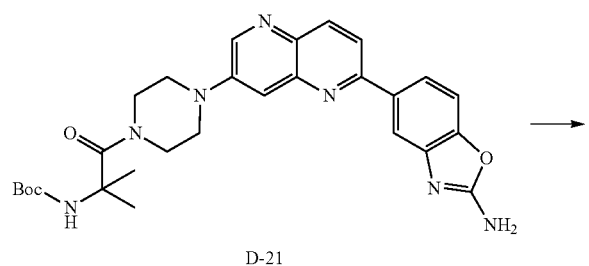

D-21

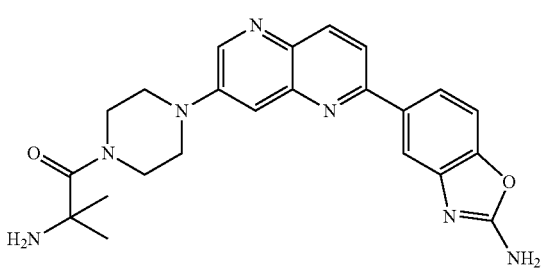

43

Acetyl chloride (4.3 mL, 60.5 mmol) was added to MeOH (11 mL) at 0° C., the resulting solution was stirred at 0° C. for 30 min. To this solution, tert-butyl(1-(4-(6-(2-aminobenzo[d]oxazol-5-yl)-1,5-naphthyridin-3-yl)piperazin-1-yl)-2-methyl-1-oxopropan-2-yl)carbamate (D-21) (85 mg, 0.16 mmol, 1.0 eq) was added, and the mixture was stirred at RT for 2 h. The reaction was complete based on TLC analysis. The mixture was diluted with water (20 mL), neutralized with solid Na$_2$CO$_3$ (about 3.5 g) to adjust pH value to 8-9, and extracted with CH$_2$Cl$_2$ (6×30 mL). The combined organic layer was dried over Na$_2$SO$_4$ and filtered. The filtrate was concentrated in vacuo and purified by silica gel column chromatography (11% MeOH/CH$_2$Cl$_2$) to afford the desired product, 2-amino-1-(4-(6-(2-aminobenzo[d]oxazol-5-yl)-1,5-naphthyridin-3-yl)piperazin-1-yl)-2-methylpropan-1-one (43) (43 mg, 62.3%) as a yellow solid. $^1$H NMR (400 MHz, DMSO-d6) δ: 8.96 (s, 1H), 8.28 (d, J=8.8 Hz, 1H), 8.12-8.09 (m, 2H), 7.92 (d, J=7.6 Hz, 1H), 7.59 (s, 1H), 7.60-7.47 (m, 3H), 4.01 (m, 4H), 3.42 (m, 4H), 1.347 (s, 6H); ESI-MS m/z: 432.21 [M+H]$^+$.

Example 3

Synthesis of 5-(3-morpholinopyrido[2,3-b]pyrazin-6-yl)benzo[d]oxazol-2-amine

Example 3a

Synthesis of 6-chloropyridine-2,3-diamine (E-24)

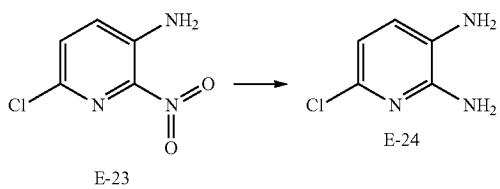 [SMILES: Nc1ccc(Cl)nc1[N+](=O)[O-] ; Nc1ccc(Cl)nc1N]

A mixture of 6-chloro-2-nitropyridin-3-amine (E-23) (8.8 g, 51 mmol, 1.0 eq) and Raney nickel (0.88 g) in Methanol (100 mL) was stirred under hydrogen at RT for 24 h, then filtered and the filtrate was concentrated in vacuo to afford the desired product 6-chloropyridine-2,3-diamine (E-24) (7 g, 95.6% yield) as a pale solid. ESI-MS m/z: 144.05[M+H]$^+$.

Example 3b

Synthesis of ethyl 2-(2-amino-6-chloropyridin-3-ylamino)acetate (E-25)

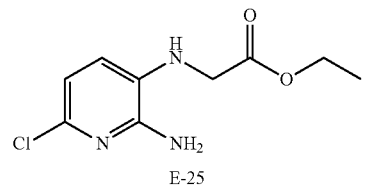

A stirred mixture of 6-chloropyridine-2,3-diamine (E-24) (7.2 g, 50 mol, 1.0 eq) and potassium carbonate (6.9 g, 50 mmol, 1 eq) in DMF (100 mL) was stirred for 30 min and then ethyl bromoacetate (9.2 g, 55 mmol, 1.1 eq) was added, the resulting mixture was stirred at 60-70° C. for 3 h. The reaction was complete based on TLC analysis. The reaction mixture was poured into ice-water (200 mL) and extracted with ethyl acetate (3×100 mL). The combined organic layers were washed with brine, dried over Na$_2$SO$_4$ and filtered. The filtrate was concentrated in vacuo to afford the desired product ethyl 2-(2-amino-6-chloropyridin-3-ylamino)acetate (E-25) (5.8 g, 50.5% yield) as a white solid. $^1$H NMR (300 MHz, DMSO-d6) δ: 6.39 (m, 2H), 5.93 (bs, 2H), 5.32 (m, 1H), 4.08 (m, 2H), 3.88 (d, J=6.0 Hz, 2H), 1.15 (m, 3H); ESI-MS m/z: 230.05 [M+H]⁺.

Example 3c

Synthesis of 6-chloro-1,2-dihydropyrido[2,3-b]pyrazin-3(4H)-one (E-26)

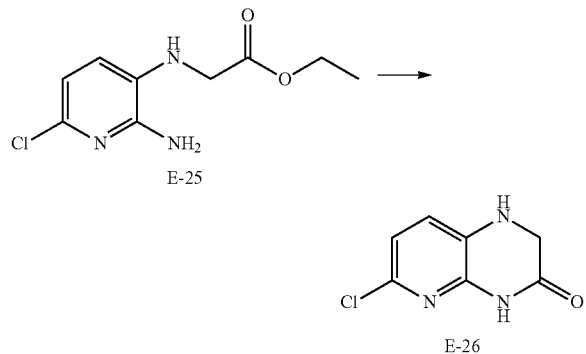

To a solution of ethyl 2-(2-amino-6-chloropyridin-3-ylamino)acetate (E-25) (4.58 g, 20 mmol, 1.0 eq) in dry 1,4-dioxane (50 mL) was added sodium hydride (60% in mineral oil, 240 mg, 6 mmol, 0.3 eq), the resulting mixture was stirred at reflux for 2 h then cooled to RT and neutralized with con. HCl to adjust the pH value to 8~9, concentrated in vacuo to remove most of solvent and then filtered, the filter cake was washed with water and ethyl acetate/petroleum ether (1:1) and dried to afford the desired product 6-chloro-1,2-dihydropyrido[2,3-b]pyrazin-3(4H)-one (E-26) (2.5 g, 68% yield) as a pale solid. ¹H NMR (300 MHz, DMSO-d6) δ: 10.86 (bs, 1H), 6.96 (d, J=8.1 Hz, 1H), 6.79 (d, J=8.1 Hz, 1H), 6.35 (bs, 1H), 3.78 (d, J=1.5 Hz, 2H); ESI-MS m/z: 183.95 [M+H]⁺.

Example 3d

Synthesis of 6-chloropyrido[3,2-b]pyrazin-3(4H)-one (E-27)

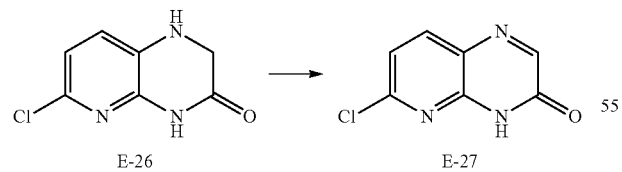

To a mixture of 6-chloro-1,2-dihydropyrido[2,3-b]pyrazin-3(4H)-one (E-26) (3.68 g, 20 mmol, 1.0 eq) in 1,4-dioxane (80 mL), manganese dioxide (19.4 g, 223 mmol, 11.1 eq) was added. The resulting mixture was stirred at reflux for 2 h then cooled to RT, filtered, the cake was washed with ethyl acetate and methanol. The combined filtrates were concentrated in vacuo to afford the desired product 6-chloropyrido[3,2-b]pyrazin-3(4H)-one (E-27) (3 g, 82% yield) as a pale solid. ¹H NMR (300 MHz, DMSO-d6) δ: 13.03 (bs, 1H), 8.19 (m, 2H), 7.38 (d, J=8.4 Hz, 1H); ESI-MS m/z: 180.00 [M−H]⁻.

Example 3e

Synthesis of 3,6-dichloropyrido[2,3-b]pyrazine (E-28)

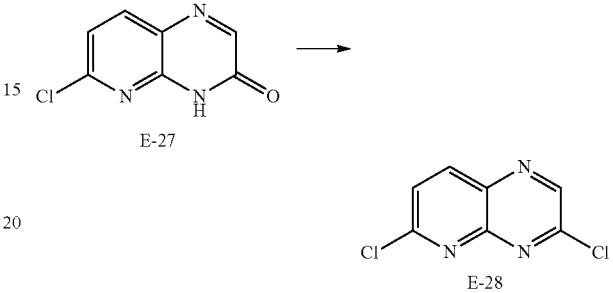

6-chloropyrido[3,2-b]pyrazin-3(4H)-one (E-27) (9 g, 49.8 mmol) was dissolved in POCl₃ (100 mL) and the resulting mixture was stirred at reflux for 3 h. The reaction was complete based on TLC analysis. The mixture was cooled to RT and concentrated in vacuo to remove POCl₃. The residue was poured into ice water (150 mL) and extracted with DCM (3×100 mL). The combined organic layers were washed with brine, dried over Na₂SO₄ and filtered. The filtrate was concentrated in vacuo to give the desired product 3,6-dichloropyrido[2,3-b]pyrazine (E-28) (9 g, 90% yield) as a solid. ESI-MS m/z: 199.97 [M+H]⁺.

Example 3f

Synthesis of 6-chloro-3-morpholinopyrido[2,3-b]pyrazine (E-29)

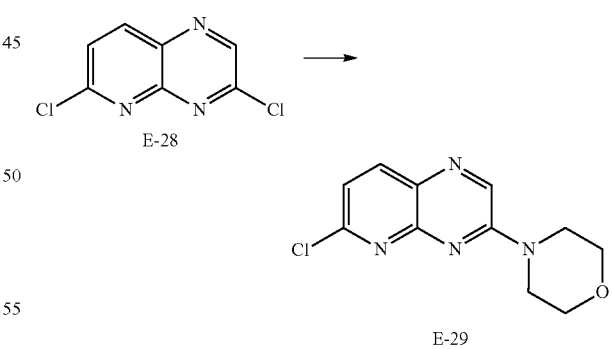

A mixture of 3,6-dichloropyrido[2,3-b]pyrazine (E-28) (201 mg, 1 mmol, 1.0 eq) and morpholine (175 μL, 2 mmol, 2.0 eq) and triethylamine (270 μL, 2 mmol, 2.0 eq) in DCM (20 mL) was stirred at RT for 2 h. Then water (20 mL) was added. The organic layer was separated, washed with brine (2×10 mL), dried over anhydrous Na₂SO₄ and filtered. The filtrate was concentrated in vacuo to afford the desired product 6-chloro-3-morpholinopyrido[2,3-b]pyrazine (E-29) (100 mg, 40% yield). ¹H NMR (300 MHz, CDCl₃-d6) δ: 8.59

(s, 1H), 8.15 (d, J=6.6 Hz, 1H), 7.35 (d, J=6.3 Hz, 1H), 3.90 (m, 8H); ESI-MS m/z: 251.00 [M+H]$^+$.

Example 3g

Synthesis of 5-(3-morpholinopyrido[2,3-b]pyrazin-6-yl)benzo[d]oxazol-2-amine (2)

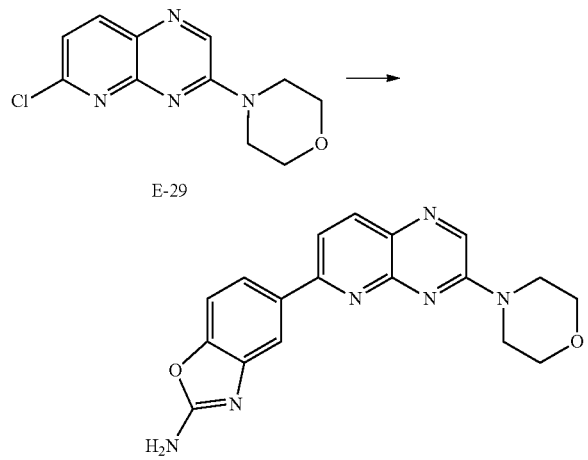

A mixture of 6-chloro-3-morpholinopyrido[2,3-b]pyrazine (E-29) (100 mg, 0.4 mmol, 1.0 eq), 2-aminobenzo[d]oxazol-5-ylboronic acid (108 mg, 0.6 mmol, 1.5 eq), Pd(PPh$_3$)$_4$ (50 mg, 0.04 mmol, 0.1 eq), and Na$_2$CO$_3$ (0.22 g, 2.0 mmol, 5.0 eq),) were dissolved in a mixture of 1,4-dioxane (15 mL) and water (5 mL). The resulting mixture was degassed and back-filled with argon three times and heated at reflux temperature for 2 h. The reaction was complete based on TLC analysis. The reaction mixture was concentrated in vacuo and the residue was purified by column chromatography on silica gel (60:1:0.02 MeOH-DCM-NH3.H20) to afford 5-(3-morpholinopyrido[2,3-b]pyrazin-6-yl)benzo[d]oxazol-2-amine (2) (100 mg, 72% yield) as a yellow solid. $^1$H NMR (300 MHz, DMSO-d6) δ: 8.86 (s, 1H), 8.26 (m, 1H), 8.06 (m, 2H), 7.92 (m, 1H), 7.55 (bs, 2H), 7.47 (m, 1H), 3.82 (m, 8H); ESI-MS m/z: 349.14 [M+H]$^+$.

Example 4

Synthesis of 5-(6-morpholino-1,5-naphthyridin-3-yl)benzo[d]oxazol-2-amine

Example 4a

Synthesis of 7-bromo-2-chloro-1,5-naphthyridine (F-31)

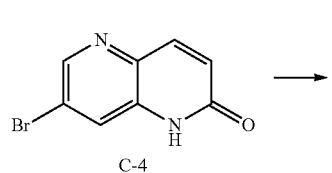

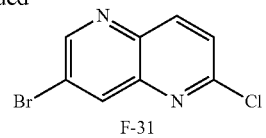

7-bromo-1,5-naphthyridin-2(1H)-one (C-4) (3.1 g, 13.78 mmol, 1.0 eq) was dissolved in POCl$_3$ (20 mL) and the resulting mixture was stirred at reflux for 1 h. The reaction was complete based on TLC analysis. The mixture was concentrated in vacuo to remove POCl$_3$. The residue was poured into ice water (30 mL) and neutralized with saturated aqueous Na$_2$CO$_3$ solution to adjust the pH value to 7-8 while keeping the temperature below 10° C. The resulting mixture was extracted with ethyl acetate (3×30 mL), the combined organic layer was washed with brine, dried over Na$_2$SO$_4$ and filtered. The filtrate was concentrated in vacuo to afford the desired product 7-bromo-2-chloro-1,5-naphthyridine (F-31) (2.11 g, 62.9% yield). ESI-MS m/z: 242.9 [M+H]$^+$.

Example 4b

Synthesis of 7-bromo-2-morpholino-1,5-naphthyridine (F-32)

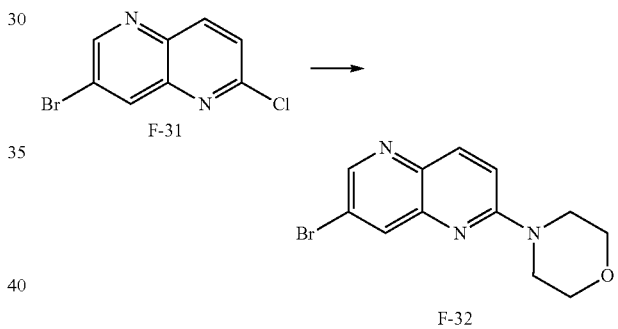

A mixture of 7-bromo-2-chloro-1,5-naphthyridine (F-31) (200 mg, 0.82 mmol, 1.0 eq) and morpholine (10 mL) was stirred in a sealed-tube at 140° C. overnight. The reaction mixture was cooled to RT, diluted with ethyl acetate (150 mL) and then washed with brine, dried over Na$_2$SO$_4$ and filtered. The filtrate was concentrated in vacuo to afford the desired product 7-bromo-2-morpholino-1,5-naphthyridine (F-32) (180 mg, 74.7% yield). ESI-MS m/z: 294.01 [M+H]$^+$.

Example 4c

Synthesis of 5-(6-morpholino-1,5-naphthyridin-3-yl)benzo[d]oxazol-2-amine (73)

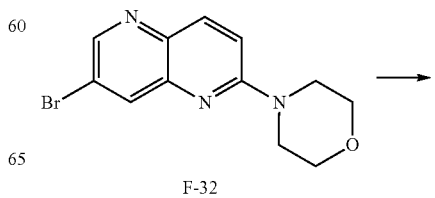

-continued

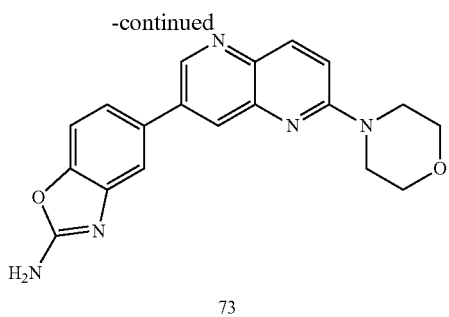

73

A mixture of 7-bromo-2-morpholino-1,5-naphthyridine (F-32) (180 mg, 0.6 mmol, 1.0 eq), 2-aminobenzo[d]oxazol-5-ylboronic acid (131 mg, 0.73 mmol, 1.2 eq), Pd(PPh$_3$)$_4$ (71 mg, 0.06 mmol, 0.1 eq), and Na$_2$CO$_3$ (195 mg, 1.8 mmol, 3.0 eq) were dissolved in a mixture of 1,4-dioxane (10 mL) and water (10 mL). The resulting mixture was degassed and back-filled with argon three times and heated at reflux under an argon atmosphere for 2 h. The reaction was complete based on TLC analysis. The mixture was concentrated in vacuo and the residue was purified by column chromatography on silica gel (3-5% MeOH-DCM) to afford 5-(6-morpholino-1,5-naphthyridin-3-yl)benzo[d]oxazol-2-amine (73) (140 mg, 67.2% yield). $^1$H NMR (400 MHz, DMSO-d6) δ: 8.93 (s, 1H), 8.10 (m, 2H), 7.66 (s, 1H), 7.53 (s, 2H), 7.45 (m, 3H), 3.74 (m, 8H); ESI-MS m/z: 348.11 [M+H]$^+$.

Example 5

IC50 Values for Selected Compounds

TABLE 2

| | | | | | | | |
|---|---|---|---|---|---|---|---|
| Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |

In Vitro IC$_{50}$ data for selected compounds of the invention.

| # | Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |
|---|---|---|---|---|---|---|---|---|
| 1 | (structure) | | +++ | ++++ | ++ | ++ | ++ | Calcd: 361.17 Found: 362.2 [M + H]$^+$ |
| 2 | (structure) | ++++ | +++ | + | ++++ | | +++ | Calcd: 348.13 Found: 349.2 [M + H]$^+$ |
| 3 | (structure) | | +++ | ++ | + | +++ | | Calcd: 340.11 Found: 341.0 [M + H]$^+$ |

TABLE 2-continued

In Vitro IC$_{50}$ data for selected compounds of the invention.

| | Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |
|---|---|---|---|---|---|---|---|---|
| 4 | 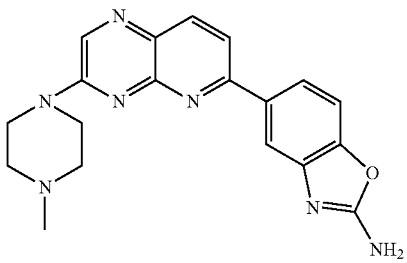 | | +++ | +++ | ++ | ++ | ++ | Calcd: 361.17 Found: 362.2 [M + H]$^+$ |
| 5 | 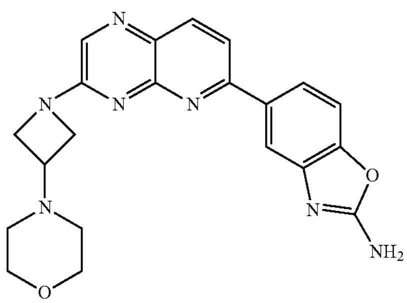 [SMILES: Nc1nc2cc(-c3ccc4ncc(N5CC(N6CCOCC6)C5)nc4n3)ccc2o1] | ++ | ++++ | + | ++ | ++ | ++ | Calcd: 403.18 Found: 404.2 [M + H]$^+$ |
| 6 | 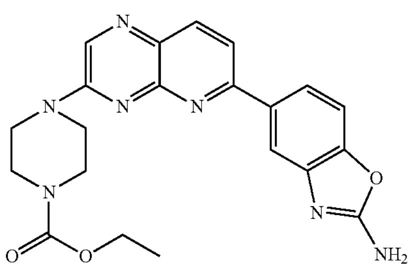 [SMILES: CCOC(=O)N1CCN(c2cnc3ccc(-c4ccc5oc(N)nc5c4)nc3n2)CC1] | | ++++ | +++ | +++ | +++ | +++ | Calcd: 419.17 Found: 420.2 [M + H]$^+$ |
| 7 | 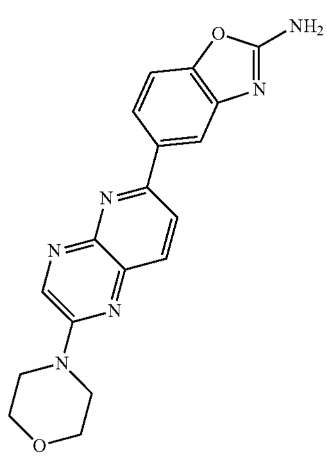 [SMILES: Nc1nc2cc(-c3ccc4nc(N5CCOCC5)cnc4n3)ccc2o1] | | + | + | + | + | | Calcd: 348.13 Found: 349.2 [M + H]$^+$ |

TABLE 2-continued

In Vitro IC$_{50}$ data for selected compounds of the invention.

| Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |
|---|---|---|---|---|---|---|---|
| 8 | | ++++ | + | ++ | +++ | ++ | Calcd: 480.17 Found: 481.0 [M + H]$^+$ |
| 9 | | ++++ | ++ | ++ | ++++ | +++ | Calcd: 416.16 Found: 417.2 [M + H]$^+$ |
| 10 | ++ | ++++ | + | ++ | ++ | ++ | Calcd: 416.21 Found: 417.2 [M + H]$^+$ |
| 11 | | ++++ | ++ | + | ++++ | | Calcd: 345.12 Found: 346.0 [M + H]$^+$ |

TABLE 2-continued

In Vitro IC$_{50}$ data for selected compounds of the invention.

| | Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |
|---|---|---|---|---|---|---|---|---|
| 12 | 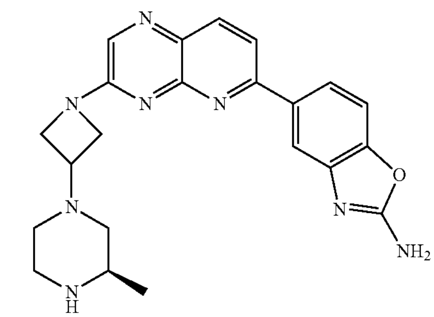 [SMILES: C[C@@H]1CN(C2CN(c3cnc4ccc(-c5ccc6oc(N)nc6c5)nc4n3)C2)CCN1] | + | ++++ | + | ++ | + | ++ | Calcd: 416.21 Found: 417.0 [M + H]$^+$ |
| 13 | 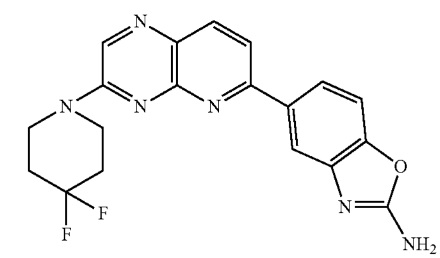 [SMILES: Nc1nc2cc(-c3ccc4ncc(N5CCC(F)(F)CC5)nc4n3)ccc2o1] | | ++++ | + | + | ++++ | ++ | Calcd: 382.14 Found: 383.2 [M + H]$^+$ |
| 14 | 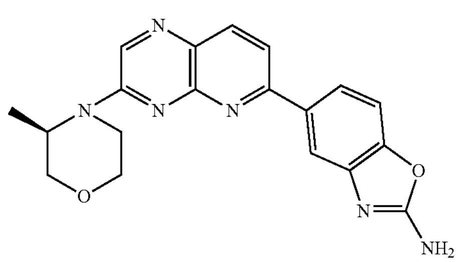 [SMILES: C[C@@H]1COCCN1c1cnc2ccc(-c3ccc4oc(N)nc4c3)nc2n1] | | ++++ | ++ | ++ | ++++ | +++ | Calcd: 362.15 Found: 363.2 [M + H]$^+$ |
| 15 | 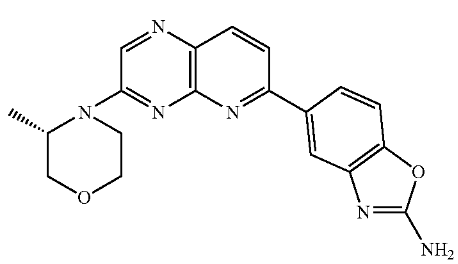 [SMILES: C[C@H]1COCCN1c1cnc2ccc(-c3ccc4oc(N)nc4c3)nc2n1] | | ++++ | ++ | + | ++++ | +++ | Calcd: 362.15 Found: 363.0 [M + H]$^+$ |
| 16 | 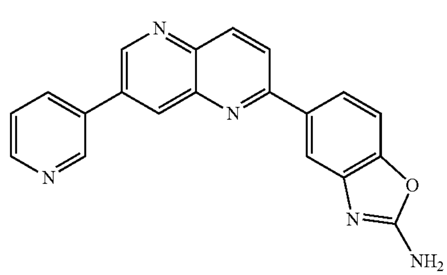 [SMILES: Nc1nc2cc(-c3ccc4ncc(-c5cccnc5)cc4n3)ccc2o1] | | ++++ | ++ | ++ | ++++ | + | Calcd: 339.11 Found: 340.0 [M + H]$^+$ |

TABLE 2-continued
In Vitro IC$_{50}$ data for selected compounds of the invention.
| Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |
|---|---|---|---|---|---|---|---|
| 17 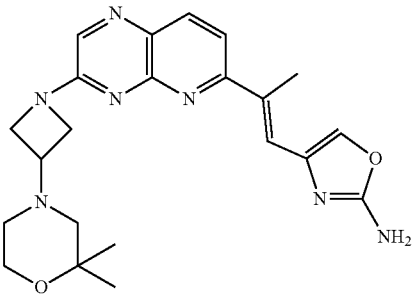 | | +++ | + | + | ++ | | Calcd: 431.21 Found: 432.2 [M + H]$^+$ |
| 18 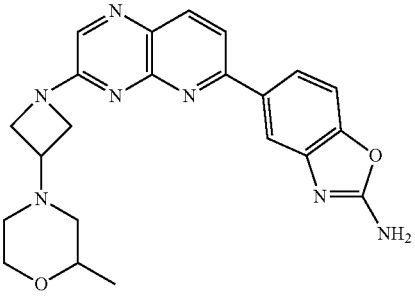 [SMILES: CC1CN(C2CN(c3cnc4ccc(-c5ccc6oc(N)nc6c5)nc4n3)C2)CCO1] | | +++ | + | + | ++ | | Calcd: 417.19 Found: 418.0 [M + H]$^+$ |
| 19 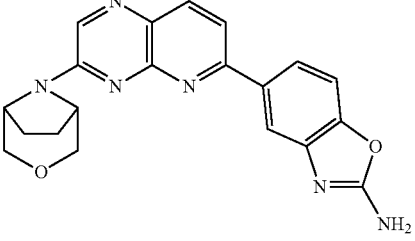 | + | ++++ | + | + | ++++ | +++ | Calcd: 374.15 Found: 375.0 [M + H]$^+$ |
| 20 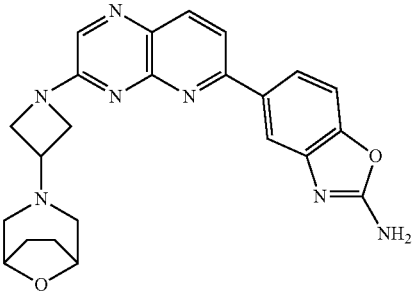 [SMILES: Nc1nc2cc(-c3ccc4ncc(N5CC(N6CC7CCC(C6)O7)C5)nc4n3)ccc2o1] | | +++ | + | + | ++ | | Calcd: 429.19 Found: 430.2 [M + H]$^+$ |

TABLE 2-continued

In Vitro IC$_{50}$ data for selected compounds of the invention.

| Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |
|---|---|---|---|---|---|---|---|
| 21 | | ++++ | + | ++ | + | | ++ | Calcd: 430.22 Found: 431.0 [M + H]$^+$ |
| 22 | | ++++ | +++ | + | ++++ | | ++ | Calcd: 347.14 Found: 348.0 [M + H]$^+$ |
| 23 | | ++++ | ++ | + | ++++ | | | Calcd: 373.15 Found: 374.2 [M + H]$^+$ |
| 24 | | ++++ | ++++ | ++ | +++ | | ++ | Calcd: 360.17 Found: 361.2 [M + H]$^+$ |
| 25 | | ++++ | + | ++ | ++ | | ++ | Calcd: 430.22 Found: 431.2 [M + H]$^+$ |

TABLE 2-continued

In Vitro IC$_{50}$ data for selected compounds of the invention.

| | Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |
|---|---|---|---|---|---|---|---|---|
| 26 | 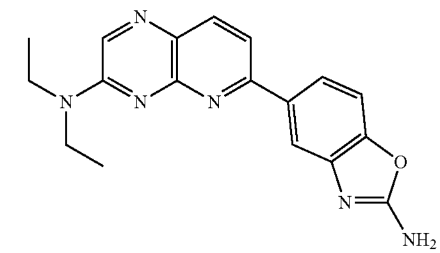 [SMILES: CCN(CC)c1cnc2ccc(-c3ccc4oc(N)nc4c3)nc2n1] | | +++ | + | ++ | +++ | | Calcd: 334.15 Found: 335.2 [M + H]$^+$ |
| 27 | 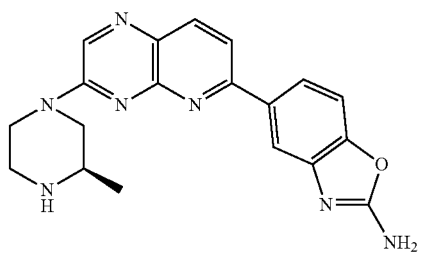 [SMILES: C[C@@H]1CN(c2cnc3ccc(-c4ccc5oc(N)nc5c4)nc3n2)CCN1] | | ++++ | ++++ | ++ | +++ | ++ | Calcd: 361.17 Found: 362.2 [M + H]$^+$ |
| 28 | 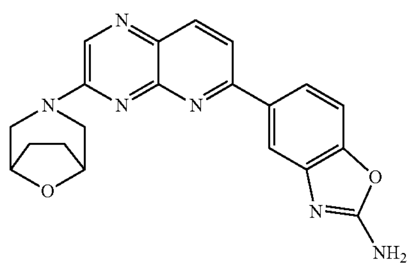 [SMILES: Nc1nc2cc(-c3ccc4ncc(N5CC6CCC(C5)O6)nc4n3)ccc2o1] | | ++++ | + | + | +++ | +++ | Calcd: 374.15 Found: 375.2 [M + H]$^+$ |
| 29 | 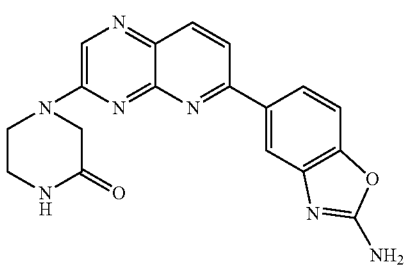 [SMILES: Nc1nc2cc(-c3ccc4ncc(N5CCNC(=O)C5)nc4n3)ccc2o1] | | ++++ | +++ | ++ | ++++ | +++ | Calcd: 361.13 Found: 362.0 [M + H]$^+$ |
| 30 | 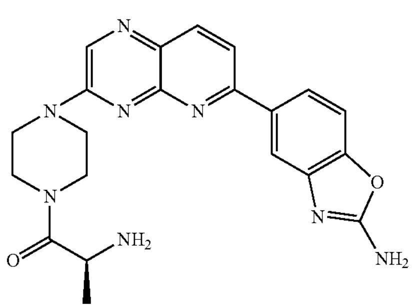 [SMILES: C[C@H](N)C(=O)N1CCN(c2cnc3ccc(-c4ccc5oc(N)nc5c4)nc3n2)CC1] | | ++++ | ++++ | ++++ | ++++ | | Calcd: 418.19 Found: 419.2 [M + H]$^+$ |

TABLE 2-continued

In Vitro IC$_{50}$ data for selected compounds of the invention.

| | Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |
|---|---|---|---|---|---|---|---|---|
| 31 | 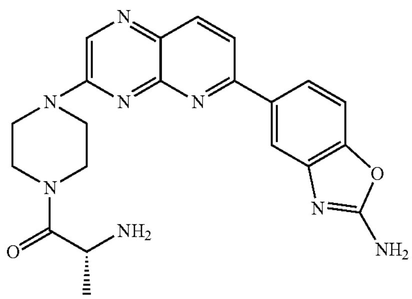 [SMILES: C[C@@H](N)C(=O)N1CCN(c2cnc3ccc(-c4ccc5oc(N)nc5c4)nc3n2)CC1] | | ++++ | ++ | ++ | +++ | ++ | Calcd: 418.91 Found: 419.2 [M + H]$^+$ |
| 32 | 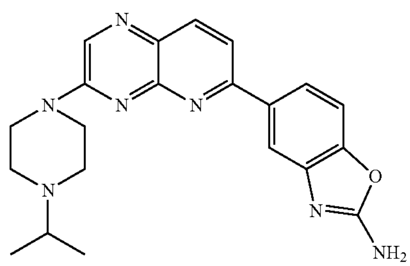 [SMILES: CC(C)N1CCN(c2cnc3ccc(-c4ccc5oc(N)nc5c4)nc3n2)CC1] | | ++++ | +++ | ++ | +++ | ++ | Calcd: 389.45 Found: 390.2 [M + H]$^+$ |
| 33 | 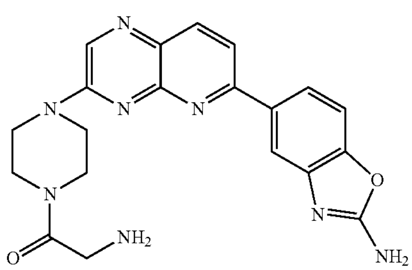 [SMILES: NCC(=O)N1CCN(c2cnc3ccc(-c4ccc5oc(N)nc5c4)nc3n2)CC1] | | ++++ | ++ | ++ | ++ | + | Calcd: 404.43 Found: 405.2 [M + H]$^+$ |
| 34 | 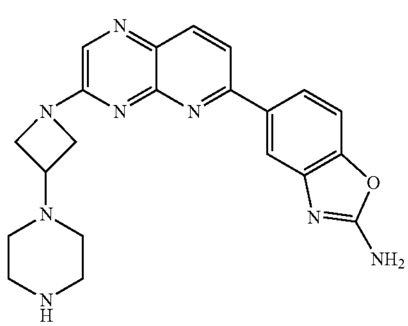 [SMILES: Nc1nc2cc(-c3ccc4ncc(N5CC(N6CCNCC6)C5)nc4n3)ccc2o1] | | +++ | + | + | + | + | Calcd: 402.19 Found: 403.0 [M + H]$^+$ |

TABLE 2-continued

In Vitro IC$_{50}$ data for selected compounds of the invention.

| Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |
|---|---|---|---|---|---|---|---|
| 35 | + | ++++ | ++ | ++ | ++ | ++ | Calcd: 456.24 Found: 457.2 [M + H]$^+$ |
| 36 |  | ++++ | ++ | + | ++++ | +++ | Calcd: 418.18 Found: 419.0 [M + H]$^+$ |
| 37 | + | ++++ | +++ | +++ | +++ | ++ | Calcd: 403.18 Found: 404.2 [M + H]$^+$ |
| 38 |  | ++++ | +++ | +++ | +++ | ++ | Calcd: 417.19 Found: 418.0 [M + H]$^+$ |

TABLE 2-continued

In Vitro IC$_{50}$ data for selected compounds of the invention.

| | Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |
|---|---|---|---|---|---|---|---|---|
| 39 | 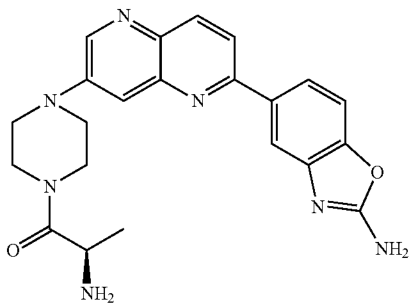 [SMILES: C[C@@H](N)C(=O)N1CCN(c2cnc3ccc(-c4ccc5oc(N)nc5c4)nc3c2)CC1] | | ++++ | ++++ | +++ | +++ | ++ | Calcd: 417.19 Found: 418.2 [M + H]$^+$ |
| 40 | 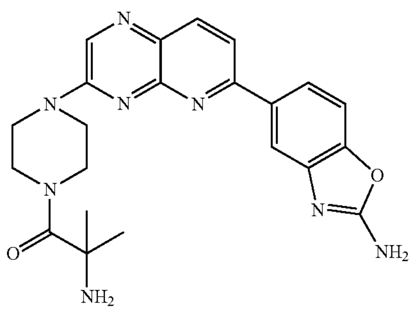 [SMILES: CC(C)(N)C(=O)N1CCN(c2cnc3ccc(-c4ccc5oc(N)nc5c4)nc3n2)CC1] | + | ++++ | ++ | ++ | ++ | ++ | Calcd: 432.20 Found: 433.2 [M + H]$^+$ |
| 41 | 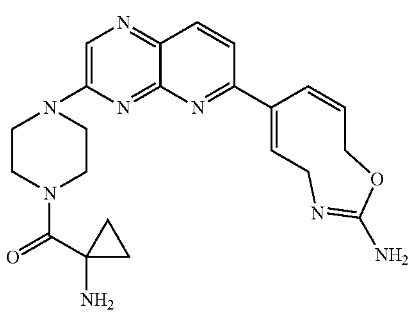 [SMILES: N/C1=N/C/C=C(c2ccc3ncc(N4CCN(C(=O)C5(N)CC5)CC4)nc3n2)\C=C/CO1] | ++ | ++++ | ++ | ++ | ++++ | ++ | Calcd: 430.19 Found: 431.0 [M + H]$^+$ |
| 42 | 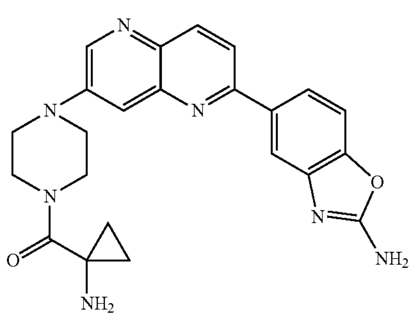 [SMILES: CC(C)(N)C(=O)N1CCN(c2cnc3ccc(-c4ccc5oc(N)nc5c4)nc3c2)CC1] | | ++++ | +++ | +++ | ++++ | +++ | Calcd: 429.19 Found: 430.0 [M + H]$^+$ |

TABLE 2-continued

In Vitro IC$_{50}$ data for selected compounds of the invention.

| | Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |
|---|---|---|---|---|---|---|---|---|
| 43 | 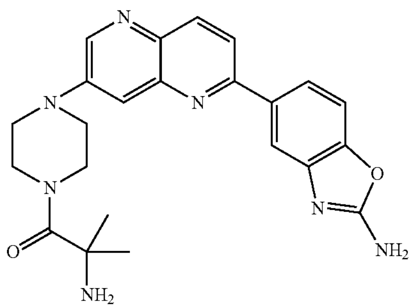 | + | ++++ | ++ | +++ | +++ | +++ | Calcd: 431.21 Found: 432.2 [M + H]$^+$ |
| 44 | 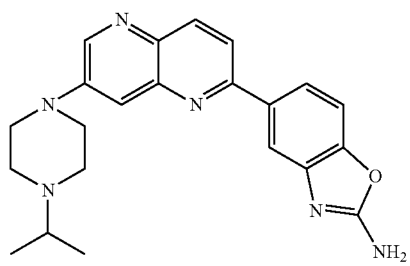 [SMILES: CC(C)N1CCN(c2cnc3ccc(-c4ccc5oc(N)nc5c4)nc3c2)CC1] | + | ++++ | +++ | +++ | +++ | ++ | Calcd: 388.20 Found: 389.0 [M + H]$^+$ |
| 45 | 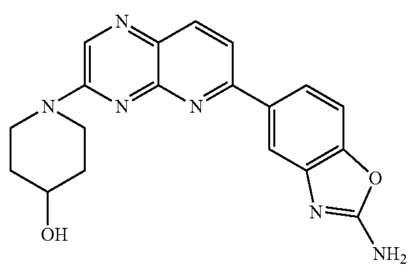 [SMILES: Nc1nc2cc(-c3ccc4ncc(N5CCC(O)CC5)nc4n3)ccc2o1] | | ++++ | ++ | + | ++++ | +++ | Calcd: 362.15 Found: 363.0 [M + H]$^+$ |
| 46 | 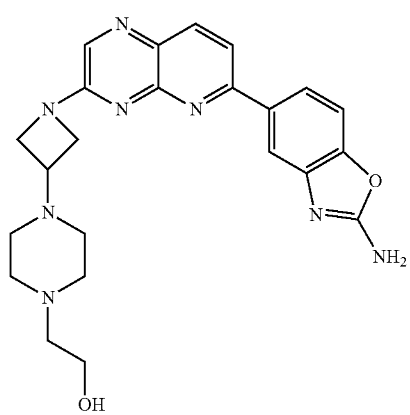 [SMILES: Nc1nc2cc(-c3ccc4ncc(N5CC(N6CCN(CCO)CC6)C5)nc4n3)ccc2o1] | + | ++++ | ++ | ++ | ++ | ++ | Calcd: 446.22 Found: 447.2 [M + H]$^+$ |

TABLE 2-continued

In Vitro IC$_{50}$ data for selected compounds of the invention.

| | Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |
|---|---|---|---|---|---|---|---|---|
| 47 | 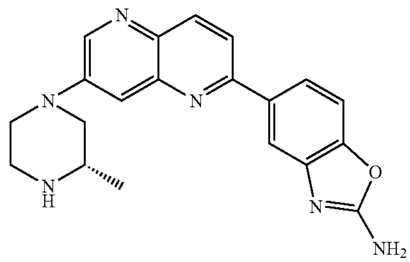 [SMILES: C[C@H]1CN(c2cnc3ccc(-c4ccc5oc(N)nc5c4)nc3c2)CCN1] | + | ++++ | ++++ | ++ | +++ | ++ | Calcd: 360.17 Found: 361.2 [M + H]⁺ |
| 48 | 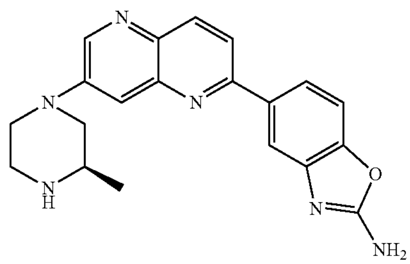 [SMILES: C[C@@H]1CN(c2cnc3ccc(-c4ccc5oc(N)nc5c4)nc3c2)CCN1] | + | ++++ | +++ | ++ | ++ | ++ | Calcd: 360.17 Found: 361.2 [M + H]⁺ |
| 49 | 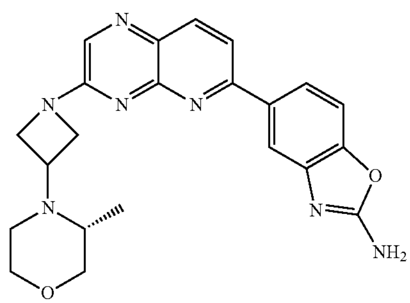 [SMILES: C[C@@H]1COCCN1C1CN(c2cnc3ccc(-c4ccc5oc(N)nc5c4)nc3n2)C1] | | ++ | + | + | ++ | | Calcd: 417.19 Found: 418.2 [M + H]⁺ |
| 50 | 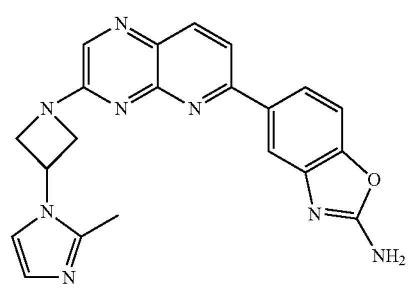 [SMILES: Cc1nccn1C1CN(c2cnc3ccc(-c4ccc5oc(N)nc5c4)nc3n2)C1] | + | ++++ | ++ | ++ | ++ | ++ | Calcd: 398.16 Found: 399.2 [M + H]⁺ |
| 51 | 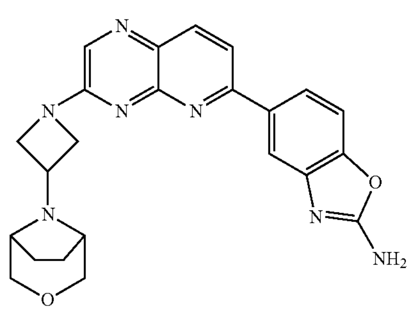 [SMILES: Nc1nc2cc(-c3ccc4ncc(N5CC(N6C7CCC6COC7)C5)nc4n3)ccc2o1] | | ++ | + | + | + | | Calcd: 429.19 Found: 430.2 [M + H]⁺ |

TABLE 2-continued

In Vitro IC$_{50}$ data for selected compounds of the invention.

| Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |
|---|---|---|---|---|---|---|---|
| 52 | + | ++++ | ++ | +++ | ++ | +++ | Calcd: 430.22 Found: 431.2 [M + H]$^+$ |
| 53 | + | ++++ | ++ | ++ | +++ | ++ | Calcd: 402.18 Found: 403.2 [M + H]$^+$ |
| 54 | + | ++++ | ++ | +++ | ++ | +++ | Calcd: 415.21 Found: 416.2 [M + H]$^+$ |
| 55 | + | ++++ | ++ | +++ | ++ | +++ | Calcd: 429.23 Found: 430.2 [M + H]$^+$ |

TABLE 2-continued

In Vitro IC$_{50}$ data for selected compounds of the invention.

| | Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |
|---|---|---|---|---|---|---|---|---|
| 56 | 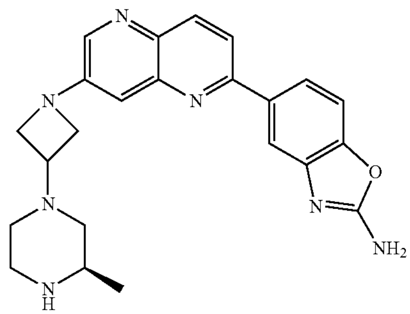 [SMILES: C[C@@H]1CN(C2CN(c3cnc4ccc(-c5ccc6oc(N)nc6c5)nc4c3)C2)CCN1] | + | ++++ | ++ | +++ | +++ | +++ | Calcd: 415.21 Found: 416.2 [M + H]$^+$ |
| 57 | 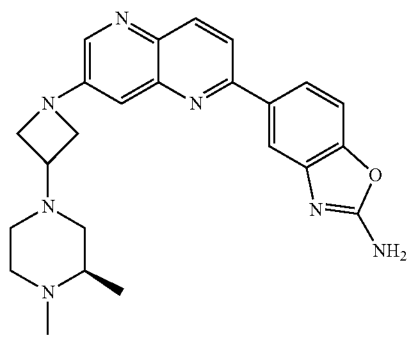 [SMILES: C[C@@H]1CN(C2CN(c3cnc4ccc(-c5ccc6oc(N)nc6c5)nc4c3)C2)CCN1C] | + | ++++ | ++ | +++ | ++ | +++ | Calcd: 429.23 Found: 430.2 [M + H]$^+$ |
| 58 | 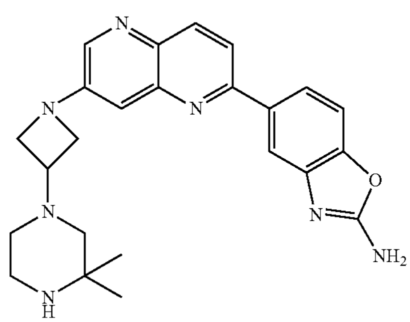 [SMILES: CC1(C)CN(C2CN(c3cnc4ccc(-c5ccc6oc(N)nc6c5)nc4c3)C2)CCN1] | + | ++++ | ++ | +++ | +++ | +++ | Calcd: 429.23 Found: 430.0 [M + H]$^+$ |
| 59 | 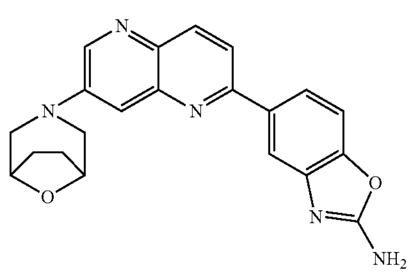 | | ++++ | + | + | ++++ | +++ | Calcd: 373.15 Found: 374.0 [M + H]$^+$ |

TABLE 2-continued

In Vitro IC$_{50}$ data for selected compounds of the invention.

| Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |
|---|---|---|---|---|---|---|---|
| 60 | + | ++++ | ++ | +++ | ++ | +++ | Calcd: 455.24 Found: 456.2 [M + H]$^+$ |
| 61 | + | ++++ | + | ++ | ++ | + | Calcd: 417.19 Found: 418.0 [M + H]$^+$ |
| 62 |  | ++++ | ++ | ++ | +++ | ++ | Calcd: 361.15 Found: 362.0 [M + H]$^+$ |
| 63 | + | ++++ | ++ | +++ | ++++ | ++ | Calcd: 397.17 Found: 398.2 [M + H]$^+$ |

TABLE 2-continued
In Vitro IC$_{50}$ data for selected compounds of the invention.
| | Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |
|---|---|---|---|---|---|---|---|---|
| 64 | 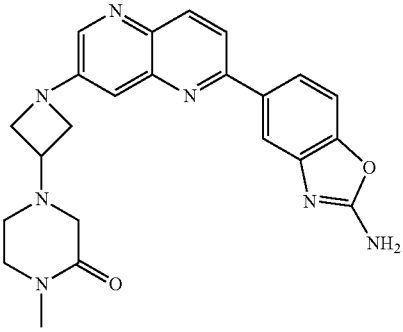 [SMILES: CN1CCN(C2CN(c3cnc4ccc(-c5ccc6oc(N)nc6c5)nc4c3)C2)CC1=O] | ++ | ++++ | ++ | +++ | ++++ | +++ | Calcd: 429.19; Found: 430.2 [M + H]$^+$ |
| 65 | 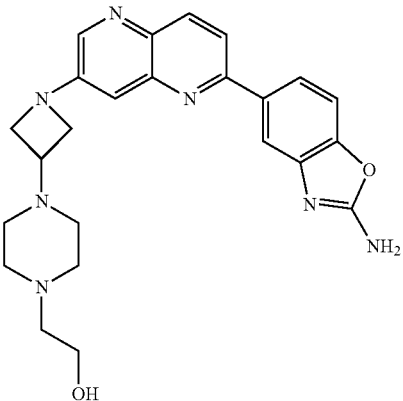 [SMILES: Nc1nc2cc(-c3ccc4ncc(N5CC(N6CCN(CCO)CC6)C5)cc4n3)ccc2o1] | + | ++++ | ++ | +++ | +++ | +++ | Calcd: 445.22 Found: 446.2 [M + H]$^+$ |
| 66 | 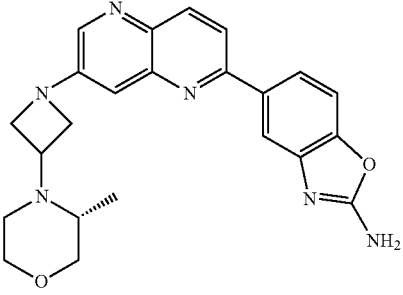 [SMILES: C[C@@H]1COCCN1C1CN(c2cnc3ccc(-c4ccc5oc(N)nc5c4)nc3c2)C1] | | ++++ | ++ | +++ | ++++ | ++ | Calcd: 416.20 Found: 417.2 [M + H]$^+$ |
| 67 | 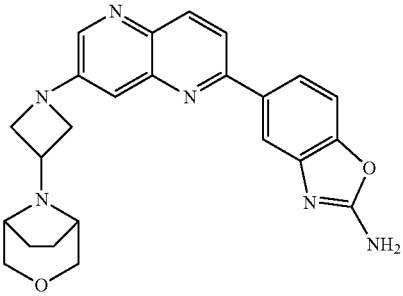 [SMILES: Nc1nc2cc(-c3ccc4ncc(N5CC(N6C7CCC6COC7)C5)cc4n3)ccc2o1] | | ++++ | + | ++ | +++ | ++ | Calcd: 428.49 Found: 429.2 [M + H]$^+$ |

TABLE 2-continued

In Vitro IC$_{50}$ data for selected compounds of the invention.

| Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |
|---|---|---|---|---|---|---|---|
| 68 | | ++++ | + | + | ++ | ++ | Calcd: 416.20 Found: 417.2 [M + H]$^+$ |
| 69 | | ++++ | ++ | ++ | ++ | ++ | Calcd: 442.22 Found: 443.2 [M + H]$^+$ |
| 70 | | ++++ | ++ | ++ | +++ | ++ | Calcd: 441.23 Found: 442.2 [M + H]$^+$ |
| 71 | + | ++++ | ++ | +++ | + | ++ | Calcd: 416.21 Found: 417.2 [M + H]$^+$ |

TABLE 2-continued

In Vitro IC$_{50}$ data for selected compounds of the invention.

| Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |
|---|---|---|---|---|---|---|---|
| 72 | + | ++++ | +++ | +++ | ++ | +++ | Calcd: 443.24 Found: 444.2 [M + H]$^+$ |
| 73 | | ++ | + | + | ++ | | Calcd: 347.14 Found: 348.2 [M + H]$^+$ |
| 74 | + | ++++ | +++ | +++ | +++ | +++ | Calcd: 415.21 Found: 416.2 [M + H]$^+$ |
| 75 | + | ++++ | +++ | +++ | ++ | +++ | Calcd: 429.23 Found: 430.2 [M + H]$^+$ |

TABLE 2-continued
In Vitro IC$_{50}$ data for selected compounds of the invention.
| | Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |
|---|---|---|---|---|---|---|---|---|
| 76 | 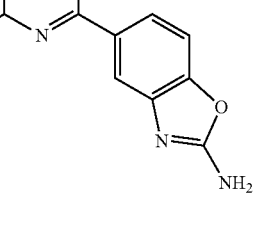 | ++ | ++++ | ++ | ++ | ++ | | Calcd: 430.22 Found: 431.2 [M + H]$^+$ |
| 77 | 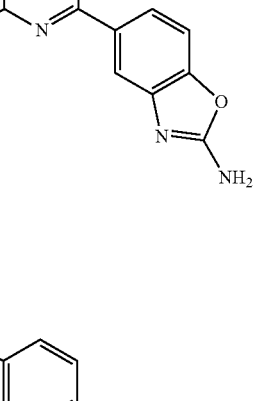 | | ++ | + | + | + | | Calcd: 444.24 Found: 445.2 [M + H]$^+$ |
| 78 | 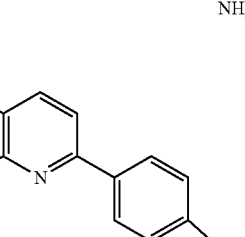 | + | ++++ | +++ | +++ | ++ | ++ | Calcd: 387.18 Found: 388.2 [M + H]$^+$ |
| 79 | 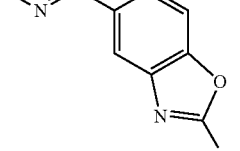 | + | ++++ | +++ | +++ | +++ | ++ | Calcd: 386.19 Found: 387.2 [M + H]$^+$ |

TABLE 2-continued

In Vitro IC$_{50}$ data for selected compounds of the invention.

| | Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |
|---|---|---|---|---|---|---|---|---|
| 80 | 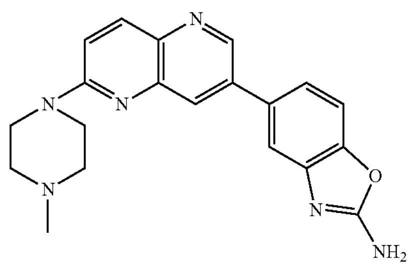 [SMILES: CN1CCN(c2ccc3ncc(-c4ccc5oc(N)nc5c4)cc3n2)CC1] | | ++ | ++ | + | + | | Calcd: 360.17 Found: 361.2 [M + H]$^+$ |
| 81 | 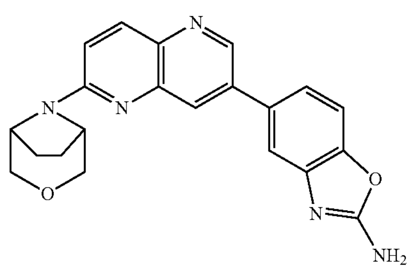 [SMILES: Nc1nc2cc(-c3cnc4ccc(N5C6CCC5COC6)nc4c3)ccc2o1] | | ++ | + | + | ++ | | Calcd: 373.15 Found: 374.2 [M + H]$^+$ |
| 82 | 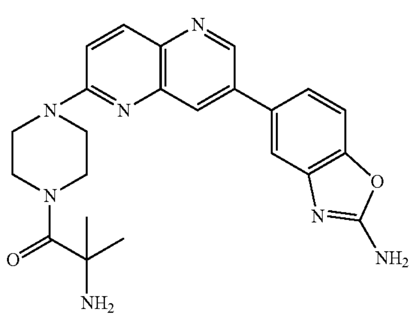 [SMILES: CC(C)(N)C(=O)N1CCN(c2ccc3ncc(-c4ccc5oc(N)nc5c4)cc3n2)CC1] | | ++ | + | + | ++ | | Calcd: 431.21 Found: 432.2 [M + H]$^+$ |
| 83 | 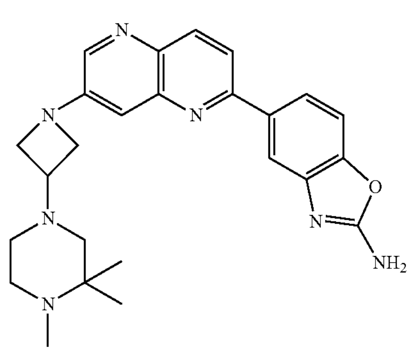 [SMILES: CN1CCN(C2CN(c3cnc4ccc(-c5ccc6oc(N)nc6c5)nc4c3)C2)CC1(C)C] | ++++ | +++ | ++++ | +++ | ++++ | | Calcd: 443.24 Found: 444.2 [M + H]$^+$ |

TABLE 2-continued

In Vitro IC$_{50}$ data for selected compounds of the invention.

| | Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |
|---|---|---|---|---|---|---|---|---|
| 84 | 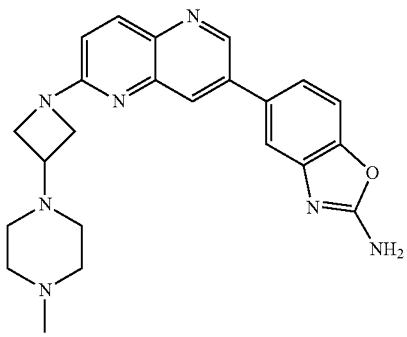 [SMILES: CN1CCN(C2CN(c3ccc4ncc(-c5ccc6oc(N)nc6c5)cc4n3)C2)CC1] | | ++ | + | + | + | | Calcd: 415.21 Found: 416.2 [M + H]$^+$ |
| 85 | 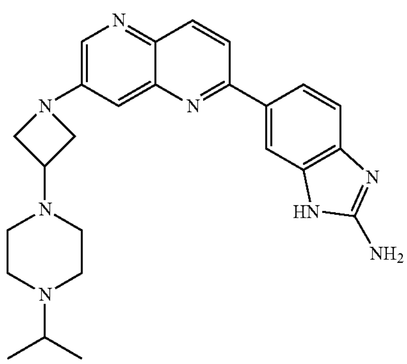 [SMILES: CC(C)N1CCN(C2CN(c3cnc4ccc(-c5ccc6nc(N)[nH]c6c5)nc4c3)C2)CC1] | | ++++ | + | + | + | | Calcd: 442.24 Found: 443.20 [M + H]$^+$ |
| 86 | 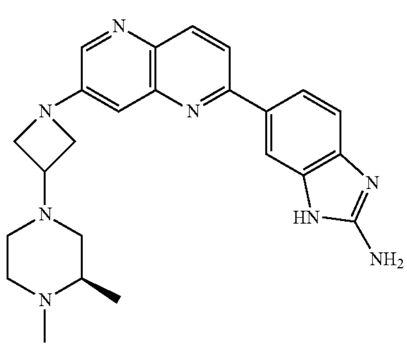 [SMILES: C[C@@H]1CN(C2CN(c3cnc4ccc(-c5ccc6nc(N)[nH]c6c5)nc4c3)C2)CCN1C] | | ++++ | + | + | + | | Calcd: 428.24 Found: 429.2 [M + H]$^+$ |
| 87 | 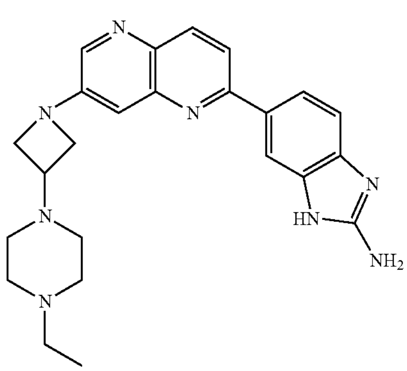 [SMILES: CCN1CCN(C2CN(c3cnc4ccc(-c5ccc6nc(N)[nH]c6c5)nc4c3)C2)CC1] | | ++++ | + | + | + | | Calcd: 428.24 Found: 429.2 [M + H]$^+$ |

TABLE 2-continued

In Vitro IC$_{50}$ data for selected compounds of the invention.

| Structure | mTORC IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) | MDA-MB-361 proliferation (nM)* | Mass Characterization |
|---|---|---|---|---|---|---|---|
| 88 [structure] | ++++ | + | + | + | | | Calcd: 414.23 Found: 415.2 [M + H]$^+$ |
| 89 [structure] | ++++ | + | + | + | | | Calcd: 428.24 Found: 429.2 [M + H]$^+$ |

The following symbols are used:
+ (greater than 10 microMolar),
++ (less than 10 microMolar),
+++ (less than 1 microMolar), and
++++ (less than 100 nM).

Example 6

Expression and Inhibition Assays of p110α/p85α, p110β/p85α, p110δ/p85α, and p110γ

Commercial kits or systems for assaying PI3-K activities are available. The commercially available kits or systems can be used to screen for inhibitors and/or agonists of PI3-Ks including but not limited to PI 3-Kinase α, β, δ, and γ. An exemplary system is PI 3-Kinase (human) HTRF™ Assay from Upstate. The assay can be carried out according to the procedures suggested by the manufacturer. Briefly, the assay is a time resolved FRET assay that indirectly measures PIP3 product formed by the activity of a PI3-K. The kinase reaction is performed in a microtitre plate (e.g., a 384 well microtitre plate). The total reaction volume is approximately 20 ul per well. In the first step, each well receives 2 ul of test compound in 20% dimethylsulphoxide resulting in a 2% DMSO final concentration. Next, approximately 14.5 ul of a kinase/PIP2 mixture (diluted in 1× reaction buffer) is added per well for a final concentration of 0.25-0.3 ug/ml kinase and 10 μM PIP2. The plate is sealed and incubated for 15 minutes at room temperature. To start the reaction, 3.5 ul of ATP (diluted in 1× reaction buffer) is added per well for a final concentration of 10 μM ATP. The plate is sealed and incubated for 1 hour at room temperature. The reaction is stopped by adding 5 ul of Stop Solution per well and then 5 ul of Detection Mix is added per well. The plate is sealed, incubated for 1 hour at room temperature, and then read on an appropriate plate reader. Data is analyzed and IC50s are generated using GraphPad Prism 5. For PI3K α, β, δ, and γ, the nM concentration of inhibitor to reach IC50 is provided. Inhibition of PI3K α at lower concentrations than those for β, δ, and γ provides evidence of specificity within this group of kinases. Similar assays, and others known in the art, can be used to measure the percent inhibition of other kinases, including but not limited to PI3K class II kinases, phosphoinositide 4 kinases (PI4K), and phosphoinositide 5 kinases (PI5K).

Example 7

Expression and Inhibition Assays of Abl

The cross-activity or lack thereof of one or more compounds of the present invention against Abl kinase can be measured according to any procedures known in the art or methods disclosed below. For example, the compounds described herein can be assayed in triplicate against recombinant full-length Abl or Abl (T315I) (Upstate) in an assay containing 25 mM HEPES, pH 7.4, 10 mM MgCl$_2$, 200 μM ATP (2.5 μCi of γ-32P-ATP), and 0.5 mg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 8

Expression and Inhibition Assays of Hck

The cross-activity or lack thereof of one or more compounds of the present invention against Hck kinase can be measured according to any procedures known in the art or methods disclosed below. The compounds described herein can be assayed in triplicate against recombinant full-length Hck in an assay containing 25 mM HEPES, pH 7.4, 10 mM MgCl$_2$, 200 μM ATP (2.5 μCi of γ-32P-ATP), and 0.5 mg/mL BSA. The optimized Src family kinase peptide substrate EIYGEFKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 9

Expression and Inhibition Assays of Insulin Receptor (IR)

The cross-activity or lack thereof of one or more compounds of the present invention against IR receptor kinase can be measured according to any procedures known in the art or methods disclosed below. The compounds described herein can be assayed in triplicate against recombinant insulin receptor kinase domain (Upstate) in an assay containing 25 mM HEPES, pH 7.4, 10 mM MgCl$_2$, 10 mM MnCl$_2$, 200 μM ATP (2.5 μCi of γ-32P-ATP), and 0.5 mg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 10

Expression and Inhibition Assays of Src

The cross-activity or lack thereof of one or more compounds of the present invention against Src kinase can be measured according to any procedures known in the art or methods disclosed below. The compounds described herein can be assayed in triplicate against recombinant full-length Src or Src (T338I) in an assay containing 25 mM HEPES, pH 7.4, 10 mM MgCl$_2$, 200 μM ATP (2.5 μCi of γ-32P-ATP), and 0.5 mg/mL BSA. The optimized Src family kinase peptide substrate EIYGEFKKK is used as phosphoacceptor (200 μM). Reactions are terminated by spotting onto phosphocellulose sheets, which are washed with 0.5% phosphoric acid (approximately 6 times, 5-10 minutes each). Sheets were dried and the transferred radioactivity quantitated by phosphorimaging.

Example 11

Expression and Inhibition Assays of DNA-PK (DNAK)

The cross-activity or lack thereof of one or more compounds of the present invention against DNAK kinase can be measured according to any procedures known in the art. DNA-PK can be purchased from Promega and assayed using the DNA-PK Assay System (Promega) according to the manufacturer's instructions.

Example 12

Expression and Inhibition Assays of mTOR

The cross-activity or lack thereof of one or more compounds of the present invention against mTor can be measured according to any procedures known in the art or methods disclosed below. The compounds described herein can be tested against recombinant mTOR (Invitrogen) in an assay containing 50 mM HEPES, pH 7.5, 1 mM EGTA, 10 mM MgCl$_2$, 2.5 mM, 0.01% Tween, 10 μM ATP (2.5 μCi of μ-32P-ATP), and 3 μg/mL BSA. Rat recombinant PHAS-1/ 4EBP1 (Calbiochem; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Other kits or systems for assaying mTOR activity are commercially available. For instance, one can use Invitrogen's LanthaScreen™ Kinase assay to test the inhibitors of mTOR disclosed herein. This assay is a time resolved FRET platform that measures the phosphorylation of GFP labeled 4EBP1 by mTOR kinase. The kinase reaction is performed in a white 384 well microtitre plate. The total reaction volume is 20 ul per well and the reaction buffer composition is 50 mM HEPES pH7.5, 0.01% Polysorbate 20, 1 mM EGTA, 10 mM MnCl$_2$, and 2 mM DTT. In the first step, each well receives 2 ul of test compound in 20% dimethylsulphoxide resulting in a 2% DMSO final concentration. Next, 8 ul of mTOR diluted in reaction buffer is added per well for a 60 ng/ml final concentration. To start the reaction, 10 ul of an ATP/GFP-4EBP1 mixture (diluted in reaction buffer) is added per well for a final concentration of 10 μM ATP and 0.5 μM GFP-4EBP1. The plate is sealed and incubated for 1 hour at room temperature. The reaction is stopped by adding 10 ul per well of a Tb-anti-pT46 4EBP1 antibody/EDTA mixture (diluted in TR-FRET buffer) for a final concentration of 1.3 nM antibody and 6.7 mM EDTA. The plate is sealed, incubated for 1 hour at room temperature, and then read on a plate reader set up for LanthaScreen™ TR-FRET. Data is analyzed and IC50s are generated using GraphPad Prism 5.

Example 13

Expression and Inhibition Assays of Vascular Endothelial Growth Receptor

The cross-activity or lack thereof of one or more compounds of the present invention against VEGF receptor can be measured according to any procedures known in the art or methods disclosed below. The compounds described herein can be tested against recombinant KDR receptor kinase domain (Invitrogen) in an assay containing 25 mM HEPES, pH 7.4, 10 mM MgCl$_2$, 0.1% BME, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 14

Expression and Inhibition Assays of Ephrin Receptor B4 (EphB4)

The cross-activity or lack thereof of one or more compounds of the present invention against EphB4 can be measured according to any procedures known in the art or methods disclosed below. The compounds described herein can be tested against recombinant Ephrin receptor B4 kinase domain (Invitrogen) in an assay containing 25 mM HEPES, pH 7.4, 10 mM $MgCl_2$, 0.1% BME, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 15

Expression and Inhibition Assays of Epidermal Growth Factor Receptor (EGFR)

The cross-activity or lack thereof of one or more compounds of the present invention against EGFR kinase can be measured according to any procedures known in the art or methods disclosed below. The compounds described herein can be tested against recombinant EGF receptor kinase domain (Invitrogen) in an assay containing 25 mM HEPES, pH 7.4, 10 mM $MgCl_2$, 0.1% BME, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 16

Expression and Inhibition Assays of KIT Assay

The cross-activity or lack thereof of one or more compounds of the present invention against KIT kinase can be measured according to any procedures known in the art or methods disclosed below. The compounds described herein can be tested against recombinant KIT kinase domain (Invitrogen) in an assay containing 25 mM HEPES, pH 7.4, 10 mM $MgCl_2$, 1 mM DTT, 10 mM $MnCl_2$, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 17

Expression and Inhibition Assays of RET

The cross-activity or lack thereof of one or more compounds of the present invention against RET kinase can be measured according to any procedures known in the art or methods disclosed below. The compounds described herein can be tested against recombinant RET kinase domain (Invitrogen) in an assay containing 25 mM HEPES, pH 7.4, 10 mM $MgCl_2$, 2.5 mM DTT, 10 μM ATP (2.5 μCi of μ-32P-ATP), and 3 μg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 18

Expression and Inhibition Assays of Platelet Derived Growth Factor Receptor (PDGFR)

The cross-activity or lack thereof of one or more compounds of the present invention against PDGFR kinase can be measured according to any procedures known in the art or methods disclosed below. The compounds described herein can be tested against recombinant PDG receptor kinase domain (Invitrogen) in an assay containing 25 mM HEPES, pH 7.4, 10 mM $MgCl_2$, 2.5 mM DTT, 10 μM ATP (2.5 μCi of μ-32P-ATP), and 3 μg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 19

Expression and Inhibition Assays of FMS-Related Tyrosine Kinase 3 (FLT-3)

The cross-activity or lack thereof of one or more compounds of the present invention against FLT-3 kinase can be measured according to any procedures known in the art or methods disclosed below. The compounds described herein can be tested against recombinant FLT-3 kinase domain (Invitrogen) in an assay containing 25 mM HEPES, pH 7.4, 10 mM $MgCl_2$, 2.5 mM DTT, 10 μM ATP (2.5 μCi of μ-32P-ATP), and 3 μg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 20

Expression and Inhibition Assays of TEK Receptor Tyrosine Kinase (TIE2)

The cross-activity or lack thereof of one or more compounds of the present invention against TIE2 kinase can be measured according to any procedures known in the art or methods disclosed below. The compounds described herein can be tested against recombinant TIE2 kinase domain (Invitrogen) in an assay containing 25 mM HEPES, pH 7.4, 10 mM $MgCl_2$, 2 mM DTT, 10 mM $MnCl_2$, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 21

B Cell Activation and Proliferation Assay

The ability of one or more subject compounds to inhibit B cell activation and proliferation is determined according to standard procedures known in the art. For example, an in vitro cellular proliferation assay is established that measures the metabolic activity of live cells. The assay is performed in a 96 well microtiter plate using Alamar Blue reduction. Balb/c splenic B cells are purified over a Ficoll-Paque™ PLUS gradient followed by magnetic cell separation using a MACS B cell Isolation Kit (Miletenyi). Cells are plated in 90 ul at 50,000 cells/well in B Cell Media (RPMI+10% FBS+Penn/Strep+50 μM bME+5 mM HEPES). A compound disclosed herein is diluted in B Cell Media and added in a 10 ul volume. Plates are incubated for 30 min at 37 C and 5% $CO_2$ (0.2% DMSO final concentration). A 50 ul B cell stimulation cocktail is then added containing either 10 ug/ml LPS or 5 ug/ml F(ab')2 Donkey anti-mouse IgM plus 2 ng/ml recombinant mouse IL4 in B Cell Media. Plates are incubated for 72 hours at 37° C. and 5% $CO_2$. A volume of 154 of Alamar Blue reagent is added to each well and plates are incubated for 5 hours at 37 C and 5% $CO_2$. Alamar Blue fluoresce is read at 560Ex/590Em, and IC50 or EC50 values are calculated using GraphPad Prism 5.

Example 22

Tumor Cell Line Proliferation Assay

The ability of one or more subject compounds to inhibit tumor cell line proliferation is determined according to standard procedures known in the art. For instance, an in vitro cellular proliferation assay can be performed to measure the metabolic activity of live cells. The assay is performed in a 96 well microtiter plate using Alamar Blue reduction. Human tumor cell lines are obtained from ATCC (e.g., MCF7, U-87 MG, MDA-MB-468, PC-3), grown to confluency in T75 flasks, trypsinized with 0.25% trypsin, washed one time with Tumor Cell Media (DMEM+10% FBS), and plated in 90 ul at 5,000 cells/well in Tumor Cell Media. A compound disclosed herein is diluted in Tumor Cell Media and added in a 10 ul volume. Plates are incubated for 72 hours at 37 C and 5% $CO_2$. A volume of 10 uL of Alamar Blue reagent is added to each well and plates are incubated for 3 hours at 37 C and 5% $CO_2$. Alamar Blue fluoresce is read at 560Ex/590Em, and IC50 values are calculated using GraphPad Prism 5. The results are expected to show that some of the compounds of the present invention are potent inhibitors of tumor cell line proliferation under the conditions tested.

Example 23

Antitumor Activity in Vivo

The compounds described herein can be evaluated in a panel of human and murine tumor models.

Paclitaxel-Refractory Tumor Models
1. Clinically-Derived Ovarian Carcinoma Model.

This tumor model is established from a tumor biopsy of an ovarian cancer patient. Tumor biopsy is taken from the patient.

The compounds described herein are administered to nude mice bearing staged tumors using an every 2 days×5 schedule.

2. A2780Tax Human Ovarian Carcinoma Xenograft (Mutated Tubulin).

A2780Tax is a paclitaxel-resistant human ovarian carcinoma model. It is derived from the sensitive parent A2780 line by co-incubation of cells with paclitaxel and verapamil, an MDR-reversal agent. Its resistance mechanism has been shown to be non-MDR related and is attributed to a mutation in the gene encoding the beta-tubulin protein.

The compounds described herein can be administered to mice bearing staged tumors on an every 2 days×5 schedule.

3. HCT116NM46 Human Colon Carcinoma Xenograft (Multi-Drug Resistant).

HCT116/VM46 is an MDR-resistant colon carcinoma developed from the sensitive HCT116 parent line. In vivo, grown in nude mice, HCT116NM46 has consistently demonstrated high resistance to paclitaxel.

The compounds described herein can be administered to mice bearing staged tumors on an every 2 days×5 schedule.

5. M5076 Murine Sarcoma Model

M5076 is a mouse fibrosarcoma that is inherently refractory to paclitaxel in vivo.

The compounds described herein can be administered to mice bearing staged tumors on an every 2 days×5 schedule.

One or more compounds of the invention can be used in combination other therapeutic agents in vivo in the multidrug resistant human colon carcinoma xenografts HCT/VM46 or any other model known in the art including those described herein.

The results are expected to show that one or more compounds of the present invention are potent inhibitors of tumor growth in vivo under the conditions tested.

Example 24

Microsome Stability Assay

The stability of one or more subject compounds is determined according to standard procedures known in the art. For example, stability of one or more subject compounds is established by an in vitro assay. In particular, an in vitro microsome stability assay is established that measures stability of one or more subject compounds when reacting with mouse, rat or human microsomes from liver. The microsome reaction with compounds is performed in 1.5 mL Eppendorf tube. Each tube contains 0.1 μL of 10.0 mg/ml NADPH; 75 μL of 20.0 mg/ml mouse, rat or human liver microsome; 0.4 μL of 0.2 M phosphate buffer, and 425 μL of dd$H_2O$. Negative control (without NADPH) tube contains 75 μL of 20.0 mg/ml mouse, rat or human liver microsome; 0.4 μL of 0.2 M phosphate buffer, and 525 μL of dd$H_2O$. The reaction is started by adding 1.0 μL of 10.0 mM tested compound. The reaction tubes are incubated at 37° C. 100 μL sample is collected into new Eppendorf tube containing 300 μL cold Methanol at 0, 5, 10, 15, 30 and 60 minutes of reaction. Samples are centrifuged at 15,000 rpm to remove protein. Supernatant of centrifuged sample is transferred to new tube. Concentration of stable compound after reaction with microsome in the supernatant is measured by Liquid Chromatography/Mass Spectrometry (LC-MS).

Example 25

Plasma Stability Assay

The stability of one or more subject compounds in plasma is determined according to standard procedures known in the art. See, e.g., *Rapid Commun. Mass Spectrom.*, 10: 1019-

1026. The following procedure is an HPLC-MS/MS assay using human plasma; other species including monkey, dog, rat, and mouse are also available. Frozen, heparinized human plasma is thawed in a cold water bath and spun for 10 minutes at 2000 rpm at 4° C. prior to use. A subject compound is added from a 400 µM stock solution to an aliquot of pre-warmed plasma to give a final assay volume of 400 µL (or 800 µL for half-life determination), containing 5 µM test compound and 0.5% DMSO. Reactions are incubated, with shaking, for 0 minutes and 60 minutes at 37° C., or for 0, 15, 30, 45 and 60 minutes at 37 C for half life determination. Reactions are stopped by transferring 50 µL of the incubation mixture to 200 µL of ice-cold acetonitrile and mixed by shaking for 5 minutes. The samples are centrifuged at 6000×g for 15 minutes at 4° C. and 120 µL of supernatant removed into clean tubes. The samples are then evaporated to dryness and submitted for analysis by HPLC-MS/MS.

Where desired, one or more control or reference compounds (5 µM) are tested simultaneously with the test compounds: one compound, propoxycaine, with low plasma stability and another compound, propantheline, with intermediate plasma stability.

Samples are reconstituted in acetonitrile/methanol/water (1/1/2, v/v/v) and analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 60 minutes relative to the amount remaining at time zero, expressed as percent, is reported as plasma stability. In case of half-life determination, the half-life is estimated from the slope of the initial linear range of the logarithmic curve of compound remaining (%) vs. time, assuming first order kinetics.

Example 26

Chemical Stability

The chemical stability of one or more subject compounds is determined according to standard procedures known in the art. The following details an exemplary procedure for ascertaining chemical stability of a subject compound. The default buffer used for the chemical stability assay is phosphate-buffered saline (PBS) at pH 7.4; other suitable buffers can be used. A subject compound is added from a 100 µM stock solution to an aliquot of PBS (in duplicate) to give a final assay volume of 400 µL, containing 5 µM test compound and 1% DMSO (for half-life determination a total sample volume of 700 µL is prepared). Reactions are incubated, with shaking, for 0 minutes and 24 hours at 37° C.; for half-life determination samples are incubated for 0, 2, 4, 6, and 24 hours. Reactions are stopped by adding immediately 100 µL of the incubation mixture to 100 µL of acetonitrile and vortexing for 5 minutes. The samples are then stored at −20° C. until analysis by HPLC-MS/MS. Where desired, a control compound or a reference compound such as chlorambucil (5 µM) is tested simultaneously with a subject compound of interest, as this compound is largely hydrolyzed over the course of 24 hours. Samples are analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 24 hours relative to the amount remaining at time zero, expressed as percent, is reported as chemical stability. In case of half-life determination, the half-life is estimated from the slope of the initial linear range of the logarithmic curve of compound remaining (%) vs. time, assuming first order kinetics.

Example 27

Akt Kinase Assay

Cells comprising components of the Akt/mTOR pathway, including but not limited to L6 myoblasts, B-ALL cells, B-cells, T-cells, leukemia cells, bone marrow cells, p190 transduced cells, philladelphia chromosome positive cells (Ph+), and mouse embryonic fibroblasts, are typically grown in cell growth media such as DMEM supplemented with fetal bovine serum and/or antibiotics, and grown to confluency.

In order to compare the effect of one or more compounds disclosed herein on Akt activation, said cells are serum starved overnight and incubated with one or more compounds disclosed herein or about 0.1% DMSO for approximately 1 minute to about 1 hour prior to stimulation with insulin (e.g., 100 nM) for about 1 minutes to about 1 hour. Cells are lysed by scraping into ice cold lysis buffer containing detergents such as sodium dodecyl sulfate and protease inhibitors (e.g., PMSF). After contacting cells with lysis buffer, the solution is briefly sonicated, cleared by centrifugation, resolved by SDS-PAGE, transferred to nitrocellulose or PVDF and immunoblotted using antibodies to phospho-Akt 5473, phospho-Akt T308, Akt, and β-actin (Cell Signaling Technologies).

Example 28

Kinase Signaling in Blood

PI3K/Akt/mTor signaling is measured in blood cells using the phosflow method (Methods Enzymol. 2007; 434:131-54). The advantage of this method is that it is by nature a single cell assay so that cellular heterogeneity can be detected rather than population averages. This allows concurrent distinction of signaling states in different populations defined by other markers. Phosflow is also highly quantitative. To test the effects of one or more compounds disclosed herein, unfractionated splenocytes, or peripheral blood mononuclear cells are stimulated with anti-CD3 to initiate T-cell receptor signaling. The cells are then fixed and stained for surface markers and intracellular phosphoproteins. It is expected that inhibitors disclosed herein inhibit anti-CD3 mediated phosphorylation of Akt-S473 and S6, whereas rapamycin inhibits S6 phosphorylation and enhances Akt phosphorylation under the conditions tested.

Similarly, aliquots of whole blood are incubated for 15 minutes with vehicle (e.g., 0.1% DMSO) or kinase inhibitors at various concentrations, before addition of stimuli to crosslink the T cell receptor (TCR) (anti-CD3 with secondary antibody) or the B cell receptor (BCR) using anti-kappa light chain antibody (Fab'2 fragments). After approximately 5 and 15 minutes, samples are fixed (e.g., with cold 4% paraformaldehyde) and used for phosflow. Surface staining is used to distinguish T and B cells using antibodies directed to cell surface markers that are known to the art. The level of phosphorylation of kinase substrates such as Akt and S6 are then measured by incubating the fixed cells with labeled antibodies specific to the phosphorylated isoforms of these proteins. The population of cells is then analyzed by flow cytometry.

The results are expected to show that one or more of the compounds of the present invention are potent and selective inhibitors of one or more members of one or more of PI3K, mTOR, and Akt signaling in blood cells under the conditions tested.

Example 29

Colony Formation Assay

Murine bone marrow cells freshly transformed with a p190 BCR-Abl retrovirus (herein referred to as p190 transduced cells) are plated in the presence of various drug combinations in M3630 methylcellulose media for about 7 days with recombinant human IL-7 in about 30% serum, and the number of colonies formed is counted by visual examination under a microscope.

Alternatively, human peripheral blood mononuclear cells are obtained from Philadelphia chromosome positive (Ph+) and negative (Ph−) patients upon initial diagnosis or relapse. Live cells are isolated and enriched for CD19+ CD34+ B cell progenitors. After overnight liquid culture, cells are plated in methocult GF+ H4435, Stem Cell Technologies) supplemented with cytokines (IL-3, IL-6, IL-7, G-CSF, GM-CSF, CF, Flt3 ligand, and erythropoietin) and various concentrations of known chemotherapeutic agents in combination with either compounds of the present disclosure. Colonies are counted by microscopy 12-14 days later. This method can be used to test for evidence of additive or synergistic activity.

The results are expected to show that one or more the compounds of the present invention are potent and selective inhibitors of p190 transduced cell colony formation under the conditions tested.

Example 30

In Vivo Effect of Kinase Inhibitors on Leukemic Cells

Female recipient mice are lethally irradiated from a γ source in two doses about 4 hr apart, with approximately 5Gy each. About 1 hr after the second radiation dose, mice are injected i.v. with about $1 \times 10^6$ leukemic cells (e.g., Ph+ human or murine cells, or p190 transduced bone marrow cells). These cells are administered together with a radioprotective dose of about $5 \times 10^6$ normal bone marrow cells from 3-5 week old donor mice. Recipients are given antibiotics in the water and monitored daily. Mice who become sick after about 14 days are euthanized and lymphoid organs are harvested for analysis. Kinase inhibitor treatment begins about ten days after leukemic cell injection and continues daily until the mice become sick or a maximum of approximately 35 days post-transplant. Inhibitors are given by oral lavage.

Peripheral blood cells are collected approximately on day 10 (pre-treatment) and upon euthanization (post treatment), contacted with labeled anti-hCD4 antibodies and counted by flow cytometry. This method can be used to demonstrate that the synergistic effect of one or more compounds disclosed herein in combination with known chemotherapeutic agents significantly reduce leukemic blood cell counts as compared to treatment with known chemotherapeutic agents (e.g., Gleevec) alone under the conditions tested.

Example 31

Treatment of Lupus Disease Model Mice

Mice lacking the inhibitory receptor FcγRIIb that opposes PI3K signaling in B cells develop lupus with high penetrance. FcγRIIb knockout mice (R2KO, Jackson Labs) are considered a valid model of the human disease as some lupus patients show decreased expression or function of FcγRIIb (S. Bolland and J. V. Ravtech 2000. *Immunity* 12:277-285).

The R2KO mice develop lupus-like disease with anti-nuclear antibodies, glomerulonephritis and proteinurea within about 4-6 months of age. For these experiments, the rapamycin analogue RAD001 (available from LC Laboratories) is used as a benchmark compound, and administered orally. This compound has been shown to ameliorate lupus symptoms in the B6.S1e1z.S1e3z model (T. Wu et al. *J. Clin Invest.* 117:2186-2196).

Lupus disease model mice such as R2KO, BXSB or MLR/lpr are treated at about 2 months old, approximately for about two months. Mice are given doses of: vehicle, RAD001 at about 10 mg/kg, or compounds disclosed herein at approximately 1 mg/kg to about 500 mg/kg. Blood and urine samples are obtained at approximately throughout the testing period, and tested for antinuclear antibodies (in dilutions of serum) or protein concentration (in urine). Serum is also tested for anti-ssDNA and anti-dsDNA antibodies by ELISA. Animals are euthanized at day 60 and tissues harvested for measuring spleen weight and kidney disease. Glomerulonephritis is assessed in kidney sections stained with H&E. Other animals are studied for about two months after cessation of treatment, using the same endpoints.

This model established in the art can be employed to test that the kinase inhibitors disclosed herein can suppress or delay the onset of lupus symptoms in lupus disease model mice.

Example 32

Murine Bone Marrow Transplant Assay

Female recipient mice are lethally irradiated from a γ ray source. About 1 hr after the radiation dose, mice are injected with about $1 \times 10^6$ leukemic cells from early passage p190 transduced cultures (e.g., as described in *Cancer Genet Cytogenet.* 2005 August; 161(1):51-6). These cells are administered together with a radioprotective dose of approximately $5 \times 10^6$ normal bone marrow cells from 3-5 wk old donor mice. Recipients are given antibiotics in the water and monitored daily. Mice who become sick after about 14 days are euthanized and lymphoid organs harvested for flow cytometry and/or magnetic enrichment. Treatment begins on approximately day 10 and continues daily until mice become sick, or after a maximum of about 35 days post-transplant. Drugs are given by oral gavage (p.o.). In a pilot experiment a dose of chemotherapeutic that is not curative but delays leukemia onset by about one week or less is identified; controls are vehicle-treated or treated with chemotherapeutic agent, previously shown to delay but not cure leukemogenesis in this model (e.g., imatinib at about 70 mg/kg twice daily). For the first phase p190 cells that express eGFP are used, and post-mortem analysis is limited to enumeration of the percentage of leukemic cells in bone marrow, spleen and lymph node (LN) by flow cytometry. In the second phase, p190 cells that express a tailless form of human CD4 are used and the post-mortem analysis includes magnetic sorting of hCD4+ cells from spleen followed by immunoblot analysis of key signaling endpoints: p Akt-T308 and 5473; pS6 and p4EBP-1. As controls for immunoblot detection, sorted cells are incubated in the presence or absence of kinase inhibitors of the present disclosure inhibitors before lysis. Optionally, "phosflow" is used to detect p Akt-S473 and pS6-S235/236 in hCD4-gated cells without prior sorting. These signaling studies are particularly useful if, for example, drug-treated mice have not developed clinical leukemia at the 35 day time point. Kaplan-Meier plots of survival are generated and statistical analysis done according to methods known in the art. Results from p190 cells are analyzed separated as well as cumulatively.

Samples of peripheral blood (100-200 µl) are obtained weekly from all mice, starting on day 10 immediately prior to commencing treatment. Plasma is used for measuring drug concentrations, and cells are analyzed for leukemia markers (eGFP or hCD4) and signaling biomarkers as described herein.

This general assay known in the art may be used to test that effective therapeutic doses of the compounds disclosed herein can be used for inhibiting the proliferation of leukemic cells.

Example 33

Rat Developing Type II Collagen Induced Arthritis Assay

In order to study the effects of the compounds of the present invention on the autoimmune disease arthritis, a collagen induced developing arthritis model is used. Female Lewis rats are given collagen injections at day 0. Bovine type II collagen is prepared as a 4 mg/ml solution in 0.01N acetic acid. Equal volumes of collagen and Freund's incomplete adjuvant are emulsified by hand mixing until a bead of the emulsified material holds its form in water. Each rodent receives a 300 µl injection of the mixture at each injection time spread over three subcutaneous sites on the back.

Oral compound administration begins on day 0 and continues through day 16 with vehicle (5% NMP, 85% PEG 400, 10% Solutol) or compounds of the present invention in vehicle or control (e.g., methotrexate) at 12 hour intervals daily. Rats are weighed on days 0, 3, 6, 9-17 and caliper measurements of ankles are taken on days 9-17. Final body weights are taken, and then the animals are euthanized on day 17. After euthanization, blood is drawn and hind paws and knees are removed. Blood is further processed for pharmacokinetics experiments as well as an anti-type II collagen antibody ELISA assay. Hind paws are weighed and then, with the knees, preserved in 10% formalin. The paws and knees are subsequently processed for microscopy. Livers, spleen and thymus are weighed. Sciatic nerves are prepared for histopathology.

Knee and ankle joints are fixed for 1-2 days and decalcified for 4-5 days Ankle joints are cut in half longitudinally, and knees are cut in half along the frontal plane. Joints are processed, embedded, sectioned and stained with toluidine blue. Scoring of the joints is done according to the following criteria:

Knee and Ankle Inflammation
0=Normal
1=Minimal infiltration of inflammatory cells in synovium/periarticular tissue
2=Mild infiltration
3=Moderate infiltration with moderate edema
4=Marked infiltration with marked edema
5=Severe infiltration with severe edema
Ankle Pannus
0=Normal
1=Minimal infiltration of pannus in cartilage and subchondral bone
2=Mild infiltration (<¼ of tibia or tarsals at marginal zones)
3=Moderate infiltration (¼ to ⅓ of tibia or small tarsals affected at marginal zones)
4=Marked infiltration (½-¾ of tibia or tarsals affected at marginal zones)
5=Severe infiltration (>¾ of tibia or tarsals affected at marginal zones, severe distortion of overall architecture)
Knee Pannus
0=Normal
1=Minimal infiltration of pannus in cartilage and subchondral bone
2=Mild infiltration (extends over up to ¼ of surface or subchondral area of tibia or femur)
3=Moderate infiltration (extends over >¼ but <½ of surface or subchondral area of tibia or femur)
4=Marked infiltration (extends over ½ to ¾ of tibial or femoral surface)
5=Severe infiltration (covers >¾ of surface)
Cartilage Damage (Ankle, Emphasis on Small Tarsals)
0=Normal
1=Minimal=minimal to mild loss of toluidine blue staining with no obvious chondrocyte loss or collagen disruption
2=Mild=mild loss of toluidine blue staining with focal mild (superficial) chondrocyte loss and/or collagen disruption
3=Moderate=moderate loss of toluidine blue staining with multifocal moderate (depth to middle zone) chondrocyte loss and/or collagen disruption, smaller tarsals affected to ½-¾ depth
4=Marked=marked loss of toluidine blue staining with multifocal marked (depth to deep zone) chondrocyte loss and/or collagen disruption, 1 or more small tarsals have full thickness loss of cartilage
5=Severe=severe diffuse loss of toluidine blue staining with multifocal severe (depth to tide mark) chondrocyte loss and/or collagen disruption
Cartilage Damage (Knee, Emphasis on Femoral Condyles)
0=Normal
1=Minimal=minimal to mild loss of toluidine blue staining with no obvious chondrocyte loss or collagen disruption
2=Mild=mild loss of toluidine blue staining with focal mild (superficial) chondrocyte loss and/or collagen disruption
3=Moderate=moderate loss of toluidine blue staining with multifocal to diffuse moderate (depth to middle zone) chondrocyte loss and/or collagen disruption
4=Marked=marked loss of toluidine blue staining with multifocal to diffuse marked (depth to deep zone) chondrocyte loss and/or collagen disruption or single femoral surface with total or near total loss
5=Severe=severe diffuse loss of toluidine blue staining with multifocal severe (depth to tide mark) chondrocyte loss and/or collagen disruption on both femurs and/or tibias
Bone Resorption (Ankle)
0=Normal
1=Minimal=small areas of resorption, not readily apparent on low magnification, rare osteoclasts
2=Mild=more numerous areas of resorption, not readily apparent on low magnification, osteoclasts more numerous, <¼ of tibia or tarsals at marginal zones resorbed
3=Moderate=obvious resorption of medullary trabecular and cortical bone without full thickness defects in cortex, loss of some medullary trabeculae, lesion apparent on low magnification, osteoclasts more numerous, ¼ to ⅓ of tibia or tarsals affected at marginal zones
4=Marked=Full thickness defects in cortical bone, often with distortion of profile of remaining cortical surface, marked loss of medullary bone, numerous osteoclasts, ½-¾ of tibia or tarsals affected at marginal zones
5=Severe=Full thickness defects in cortical bone, often with distortion of profile of remaining cortical surface, marked loss of medullary bone, numerous osteoclasts, >¾ of tibia or tarsals affected at marginal zones, severe distortion of overall architecture Bone Resorption (Knee)
0=Normal
1=Minimal=small areas of resorption, not readily apparent on low magnification, rare osteoclasts
2=Mild=more numerous areas of resorption, definite loss of subchondral bone involving ¼ of tibial or femoral surface (medial or lateral)
3=Moderate=obvious resorption of subchondral bone involving >¼ but <½ of tibial or femoral surface (medial or lateral)
4=Marked=obvious resorption of subchondral bone involving >½ but <¾ of tibial or femoral surface (medial or lateral)
5=Severe=distortion of entire joint due to destruction involving >¾ of tibial or femoral surface (medial or lateral)

Statistical analysis of body/paw weights, paw AUC parameters and histopathologic parameters were evaluated using a Student's t-test or other appropriate (ANOVA with post-test) with significance set at the 5% significance level. Percent inhibition of paw weight and AUC was calculated using the following formula:

$$\% \text{ Inhibition} = A - B/A \times 100$$

A=Mean Disease Control−Mean Normal
B=Mean Treated−Mean Normal

The results are expected to show, relative to vehicle only control or to methotrexate control, that the compounds of the present invention exhibit a significant reduction in arthritis induced ankle diameter increase over time, and reduction of ankle histopathology in at least one or more of the categories of inflammation, pannus, cartilage damage, and bone resorption as described above. The results are expected to show that one or more compounds of the present invention may be useful for the treatment and reduction of arthritis disease symptoms.

The results further are expected to show a reduction at 10, 20, and 60 mg/kg dosage levels of serum anti-type II collagen levels for selected test compounds, suggesting that one or more compounds of the present invention may not only be useful for the treatment and reduction of arthritis disease symptoms, but may also be useful for the inhibition of the autoimmune reaction itself.

Example 34

Rat Established Type II Collagen Induced Arthritis Assay

In order to examine the dose responsive efficacy of the compounds of the present invention in inhibiting the inflammation, cartilage destruction and bone resorption of 10 day established type II collagen induced arthritis in rats, compounds are administered orally daily or twice daily for 6 days.

Female Lewis rats are anesthetized and given collagen injections prepared and administered as described previously on day 0. On day 6, animals are anesthetized and given a second collagen injection. Caliper measurements of normal (pre-disease) right and left ankle joints are performed on day 9. On days 10-11, arthritis typically occurs and rats are randomized into treatment groups. Randomization is performed after ankle joint swelling is obviously established and there is evidence of bilateral disease.

After an animal is selected for enrollment in the study, treatment is initiated by the oral route. Animals are given vehicle, control (Enbrel) or compound doses, twice daily or once daily (BID or QD respectively). Administration is performed on days 1-6 using a volume of 2.5 ml/kg (BID) or 5 ml/kg (QD) for oral solutions. Rats are weighed on days 1-7 following establishment of arthritis and caliper measurements of ankles taken every day. Final body weights are taken on day 7 and animals are euthanized.

The results are expected to show reduction in mean ankle diameter increase over time for selected test compounds under the conditions tested.

Example 35

Adjuvant Induced Arthritis Assay

Intrathecal Catheterization of Rats

Isoflurane-anesthetized Lewis rats (200-250 g) are implanted with an intrathecal (IT) catheter. After a 6 d recovery period, all animals except those that appeared to have sensory or motor abnormalities (generally fewer than 5% of the total number) are used for experiments. For IT administration, 10 μl of drug or saline followed by 10 μl of isotonic saline is injected through the catheter.

Adjuvant Arthritis and Drug Treatment

Lewis rats are immunized at the base of the tail with 0.1 ml of complete Freund's adjuvant (CFA) on day 0 several days after catheter implantation (n=6/group). Drug (e.g., one or more compounds of the present invention or or vehicle) treatment is generally started on day 8 and is continued daily until day 20. Clinical signs of arthritis generally begin on day 10, and paw swelling is determined every second day by water displacement plethysmometry.

The results are expected to show that one or more compounds of the present invention demonstrates may be useful for the treatment of one or more of the diseases or conditions described herein.

Example 36

Rodent Pharmacokinetic Assay

In order to study the pharmacokinetics of the compounds of the present invention a set of 4-10 week old mice are grouped according to the following table:

| Group# | Mice/group | Compound Administration | | |
|---|---|---|---|---|
| | | (mg/kg) | Route | Regimen |
| 1 | 3 | 1 | Po | One dose |
| 2 | 3 | 3 | | |
| 3 | 3 | 10 | | |
| 4 | 3 | 30 | | |
| 5 | 3 | 60 | | |

Compounds of the present invention are dissolved in an appropriate vehicle (e.g., 5% 1-methyl-2-pyrrolidinone, 85% polyethylene glycol 400, 10% Solutor) and administered orally at 12 hour intervals daily. All animals are euthanized in $CO_2$ 2 hours after the final compound is administered. Blood is collected immediately and kept on ice for plasma isolation. Plasma is isolated by centrifuging at 5000 rpm for 10 minutes. Harvested plasma is frozen for pharmacokinetic detection.

The results are expected to demonstrate the pharmacokinetic parameters such as absorption, distribution, metabolism, excretion, and toxicity for the compounds of the present invention.

Example 37

Basotest Assay

The basotest assay is performed using Orpegen Pharma Basotest reagent kit. Heparinized whole blood is pre-incubated with test compound or solvent at 37 C for 20 min. Blood is then incubated with assay kit stimulation buffer (to prime cells for response) followed by allergen (dust mite extract or grass extract) for 20 min. The degranulation process is stopped by incubating the blood samples on ice. The cells are then labeled with anti-IgE-PE to detect basophilic granulocytes, and anti-gp53-FITC to detect gp53 (a glycoprotein expressed on activated basophils). After staining red blood cells are lysed by addition of Lysing Solution. Cells are washed, and analyzed by flow cytometry. Test compounds, when evaluated in this assay inhibit allergen induced activation of basophilic granulocytes at sub micromolar range. The results are expected to demonstrate that under the conditions tested one or more compounds of the present invention are capable of inhibiting allergen induced activation of basophils.

Example 38

Use of the Compounds of the Present Invention for Inhibition of Tumor Growth Cell Lines Cell lines of interest (A549, U87, ZR-75-1 and 786-O) are obtained from American Type Culture Collection (ATCC, Manassas, Va.). Cells are proliferated and preserved cryogenically at early passage (e.g., passage 3). One aliquot is used for further proliferation to get enough cells for one TGI study (at about passage 9).

Animals

Female athymic nude mice are supplied by Harlan. Mice are received at 4 to 6 weeks of age. All mice are acclimated for about one day to two weeks prior to handling. The mice are housed in microisolator cages and maintained under specific pathogen-free conditions. The mice are fed with irradiated mouse chow and freely available autoclaved water is provided.

Tumor Xenograft Model

Mice are inoculated subcutaneously in the right flank with 0.01 to 0.5 ml of tumor cells (approximately $1.0 \times 10^5$ to $1.0 \times 10^8$ cells/mouse). Five to 10 days following inoculation, tumors are measured using calipers and tumor weight is calculated, for example using the animal study management software, such as Study Director V.1.6.70 (Study Log). Mice with tumor sizes of about 120 mg are pair-matched into desired groups using Study Director (Day 1). Body weights are recorded when the mice are pair-matched. Tumor volume and bodyweight measurements are taken one to four times weekly and gross observations are made at least once daily. On Day 1, compounds of the present invention and reference compounds as well as vehicle control are administered by oral gavage or iv as indicated. At the last day of the experiment, mice are sacrificed and their tumors are collected 1-4 hours after the final dose. The tumors are excised and cut into two sections. One third of the tumor is fixed in formalin and embedded in paraffin blocks and the remaining two thirds of tumor is snap frozen and stored at −80° C.

Data and Statistical Analysis

Mean tumor growth inhibition (TGI) is calculated utilizing the following formula:

$$TGI = \left[1 - \frac{\left(\overline{X}_{Treated(Final)} - \overline{X}_{Treated(Day1)}\right)}{\left(\overline{X}_{Control(Final)} - \overline{X}_{Control(Day1)}\right)}\right] \times 100\%$$

Tumors that regress from the Day 1 starting size are removed from the calculations. Individual tumor shrinkage (TS) is calculated using the formula below for tumors that show regression relative to Day 1 tumor weight. The mean tumor shrinkage of each group is calculated and reported.

$$TS = \left[1 - \frac{(Tumor\ Weight_{(Final)})}{(Tumor\ Weight_{(Day\ 1)})}\right] \times 100\%$$

The model can be employed to show whether the compounds of the present invention can inhibit tumor cell growth such as renal carcinoma cell growth, breast cancer cell growth, lung cancer cell growth, or glioblastoma cell growth under the conditions tested.

Example 39

Inhibition of PI3K Pathway and Proliferation of Tumor Cells with PI3Kα Mutation Cells comprising one or more mutations in PI3Kα, including but not limited to breast cancer cells (e.g., MDA-MB-361 and T47D), and cells comprising one or more mutations in PTEN including but not limited to prostate cancer cells (e.g., PC3), are typically grown in cell growth media such as DMEM supplemented with fetal bovine serum and/or antibiotics, and grown to confluency. Cells are then treated with various concentrations of test compound for about 2 hours and subsequently lysed in cell lysis buffer. Lysates are subjected to SDS-PAGE followed by Western blot analysis to detect downstream signaling markers, including but not limited to pAKT(S473), pAKT(T308), pS6, and p4E-BP1. Degree of proliferation (and proliferation inhibition) can also be measured for cells at various doses of compound of the present invention. Based on percent inhibition of pAKT and proliferation indicated by these results, IC50 values are calculated.

Example 40

In Vitro Inhibition of Angiogenesis

Inhibition of angiogenesis in the presence of test compound is evaluated using a tube formation assay, such as by using a tube formation assay kit (e.g., commercially available from Invitrogen). Angiogenic capacity can be measured in vitro using an endothelial cell line, such as human umbilical vein endothelial cells (HUVEC). The assay is conducted according to the kit instructions, in the presence or absence of compound. Briefly, a gel matrix is applied to a cell culture surface, cells are added to the matrix-covered surface along with growth factors, with some samples also receiving an inhibitor compound, cells are incubated at 37° C. and 5% $CO_2$ long enough for control samples (no compound added) to form tube structures (such as overnight), cells are stained using a cell-permeable dye (e.g., calcein), and cells are visualized to identify the degree of tube formation. Any decrease in tube formation relative to un-inhibited control cells is indicative of angiogenic inhibition. Based on doses tested and the corresponding degree of tube formation inhibition, IC50 values for tube formation are calculated. IC50 values for cell viability can be measured using any number of methods known in the art, such as staining methods that distinguish live from dead cells (e.g., Image-iT DEAD Green viability stain commercially available from Invitrogen).

Example 41

In Vivo Efficacy in Xenogenic Mouse Model of Breast Cancer

Nude mice harboring tumors derived from implantation of human breast adenocarcinoma cells MDA-MB-361 (PI3Kα/HER2 carcinoma) are separated into untreated control (vehicle only) and treatment groups. Mice in the treatment group are further divided into mice receiving 70 mg/kg (70 mpk) of a Pan-PI3K inhibitor, or 30 mpk or 60 mpk of test compound. Mice in the treatment group receive the defined dose daily by oral lavage for 20 to 50 days, during which time tumor weight is calculated as described in example 37. Blood glucose is monitored periodically following administration of treatment. 2 hours after the final treatment, tumors are harvested and proteins are analyzed by Western blot as described above. The effect of the compounds on the localization/viability of marginal zone B cells in the spleen is also evaluated at the conclusion of treatment.

A similar experiment using 786-O cells, a human kidney carcinoma cell line having a non-mutated PI3Kα, instead of MDA cells is used to further demonstrate the specificity of test compounds. For example, a test compound is compared to a kinase inhibitor with specificity for mTor.

Example 42

Synergistic Combination with Other Kinase Inhibitors

In some embodiments, a compound of the present invention is combined with another kinase inhibitor. In some embodiments, the combined kinase inhibitor is a MEK inhibitor. A median-effect analysis is used to determine synergism, antagonism, or additivity of a compound of the present invention when combined with a MEK inhibitor. The Combination Index (CI) is determined using the Chou/Talalay equation. IC50 values for each individual compound is determined in a 72 hr CellTiter-Glo assay. For combination assays, drugs are used at their equipotent ratio (e.g., at the ratio of their IC50's). CalcuSyn software (by Biosoft) is used for dose effect analysis.

To further demonstrate synergy between kinase inhibitors, a cell arrest assay is used to determine the effects of inhibitors alone and in combination on the cycle stage of treated cells. HCT116 cells, a human colon cancer cell line, is treated with DMSO (carrier), 3 μM of a compound of the present invention including compound 54, 0.3 μM of PD0325901, or a combination of both 3 μM of test compound and 0.3 μM of a MEK inhibitor. Cells are then incubated in the presence of DMSO or inhibitor for 20 hours. The number of cells at each stage in the cell cycle is determined and expressed as a percent of the total, with an increase in the number of cells arrested at pre-G0/G1 indicating effective inhibition of cell cycle progression. This assay can be used to determine whether the combination of a compound of the present invention with other inhibitors can be synergistic.

What is claimed is:
1. A compound of the Formula I:

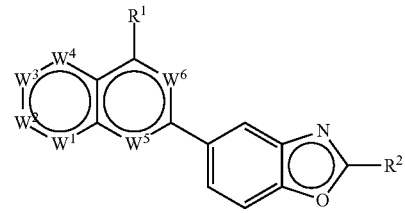

Formula I or a pharmaceutically acceptable salt thereof, wherein:
$W^1$ is N or $CR^3$; $W^2$ is N or $CR^4$; $W^3$ is N or $CR^5$; $W^4$ is N; wherein no more than two N atoms are adjacent;
$W^5$ is N;
$W^6$ is N or $CR^8$;
$R^1$ and $R^2$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, or carbonate;
$R^3$ and $R^4$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, or carbonate wherein $R^4$ is optionally substituted with one or more substituents selected from alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, alkoxycarbonyl, halo, cyano, hydroxy, nitro, phosphate, urea, or carbonate; wherein said substituents are optionally further substituted with one or more of alkyl, alkoxy, amido, amino, sulfonamido, acyloxy, alkoxycarbonyl, halo, cyano, hydroxy, nitro, oxo, phosphate, urea, or carbonate;
or $R^3$ and $R^4$ taken together form a cyclic moiety; and
$R^5$ and $R^8$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, or carbonate.

2. The compound or pharmaceutically acceptable salt of claim 1, wherein $W^2$ is $CR^4$.
3. The compound or pharmaceutically acceptable salt of claim 1, wherein $W^3$ is $CR^5$.
4. The compound or pharmaceutically acceptable salt of claim 1, wherein $W^2$ and $W^3$ are CH.
5. The compound or pharmaceutically acceptable salt of claim 1, wherein $W^6$ is $CR^8$.
6. The compound or pharmaceutically acceptable salt of claim 1, wherein $W^1$ is N.
7. The compound or pharmaceutically acceptable salt of claim 1, wherein $W^1$ is $CR^3$.
8. The compound or pharmaceutically acceptable salt of claim 1, wherein $R^2$ is amino.
9. The compound or pharmaceutically acceptable salt of claim 1, wherein $R^1$ is hydrogen.

10. The compound or pharmaceutically acceptable salt of claim 1, wherein the compound has the Formula:

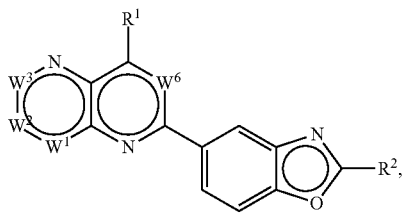

wherein $R^1$ is hydrogen; and $R^2$ is $NH_2$.

11. The compound or pharmaceutically acceptable salt of claim 1, wherein the compound has the Formula:

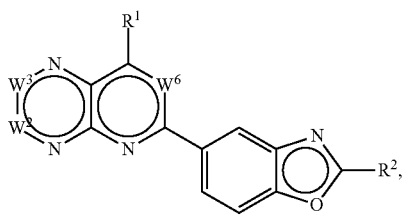

wherein $R^1$ is hydrogen; and $R^2$ is $NH_2$.

12. The compound or pharmaceutically acceptable salt of claim 10 or 11, wherein $W^6$ is CH.

13. The compound or pharmaceutically acceptable salt of claim 10, wherein the compound has the Formula:

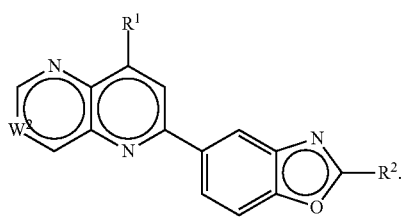

14. The compound or pharmaceutically acceptable salt of claim 11, wherein the compound has the Formula:

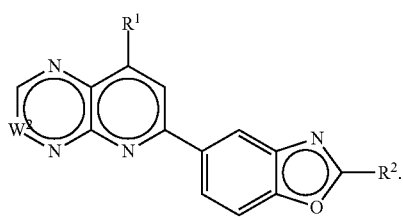

15. The compound or pharmaceutically acceptable salt of any one of claims 1, 10, 11, 13 or 14, wherein $W^2$ is $CR^4$ and $R^4$ is alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, or carbonate.

16. The compound or pharmaceutically acceptable salt of claim 15, wherein $R^4$ is aryl, heteroaryl, or heterocycloalkyl, wherein $R^4$ is optionally substituted with one or more substituents selected from alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, alkoxycarbonyl, halo, cyano, hydroxy, nitro, phosphate, urea, or carbonate; wherein said substituents are optionally further substituted with one or more of alkyl, alkoxy, amido, amino, sulfonamido, acyloxy, alkoxycarbonyl, halo, cyano, hydroxy, nitro, oxo, phosphate, urea, or carbonate.

17. The compound or pharmaceutically acceptable salt of claim 15, wherein $R^4$ is cycloalkyl, heterocycloalkyl, aryl or heteroaryl.

18. The compound or pharmaceutically acceptable salt of claim 16, wherein $R^4$ is 5-membered heteroaryl, or 6-membered heteroaryl.

19. The compound or pharmaceutically acceptable salt of claim 16, wherein $R^4$ is 4-membered heterocycloalkyl, 5-membered heterocycloalkyl, 6-membered heterocycloalkyl, or 8-membered heterocycloalkyl.

20. The compound or pharmaceutically acceptable salt of claim 19, wherein the heterocycloalkyl is morpholine, piperazine, azetidine, pyrrolidine, or piperidine.

21. The compound or pharmaceutically acceptable salt of claim 1, wherein the compound is selected from the group consisting of:

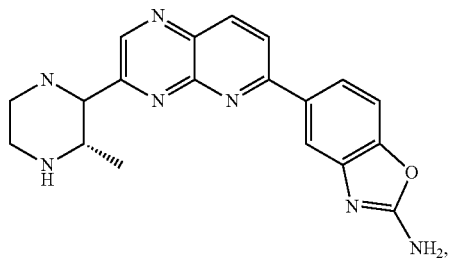

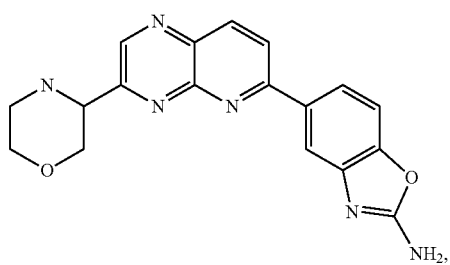

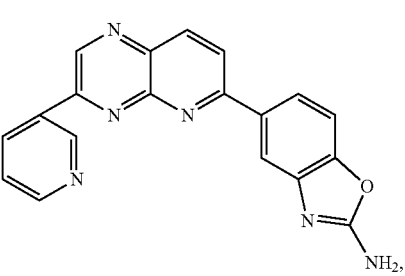

187
-continued
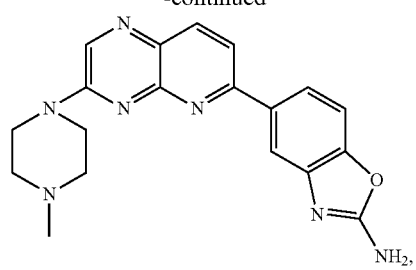
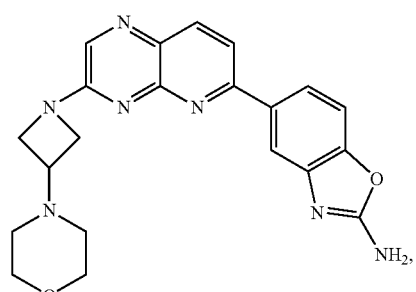
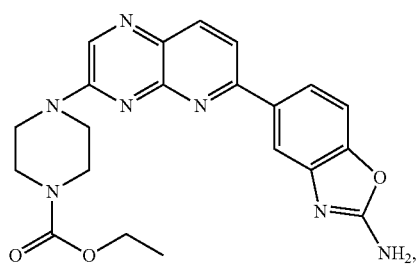
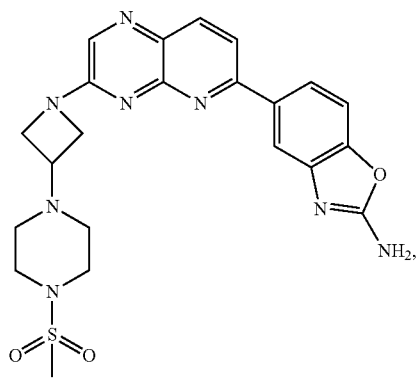
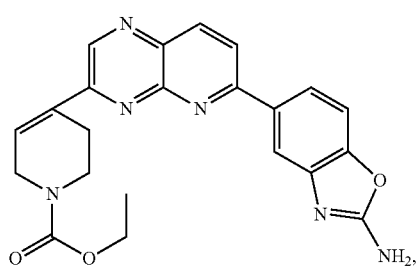
188
-continued
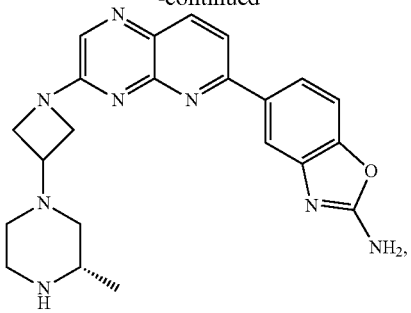
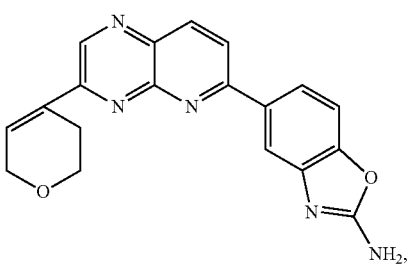
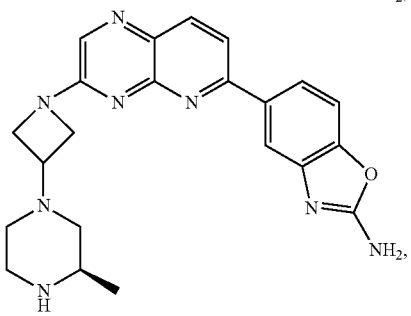
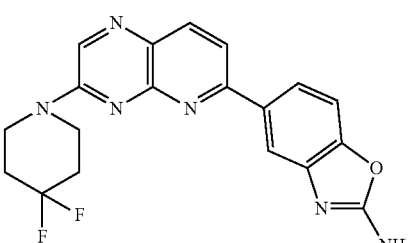
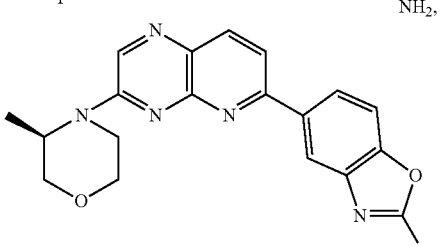
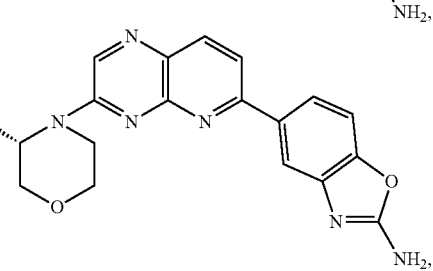

189
-continued
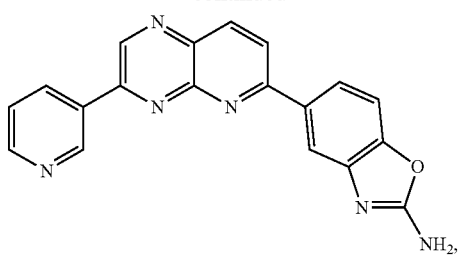
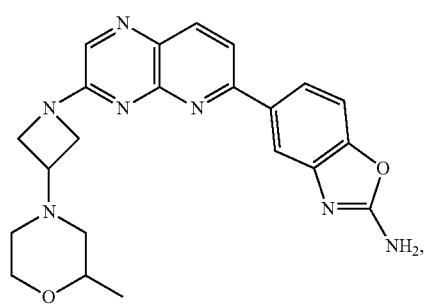
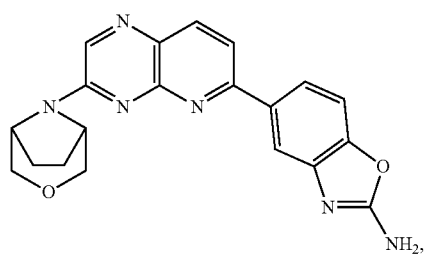
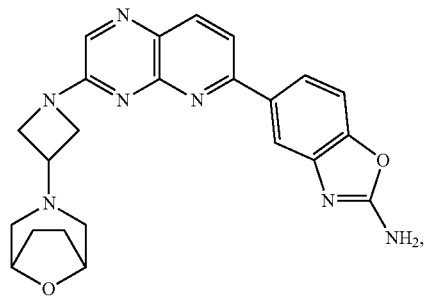
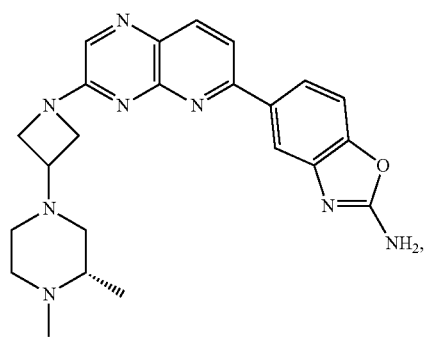
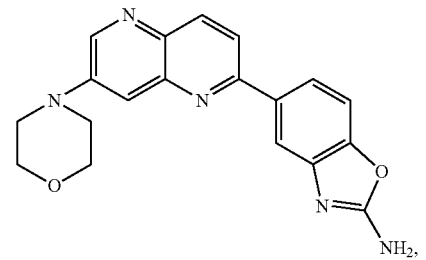
190
-continued
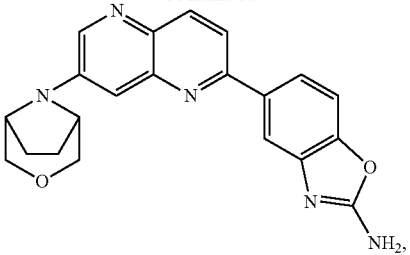
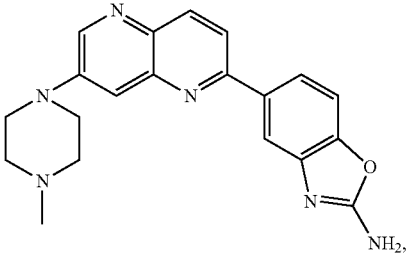
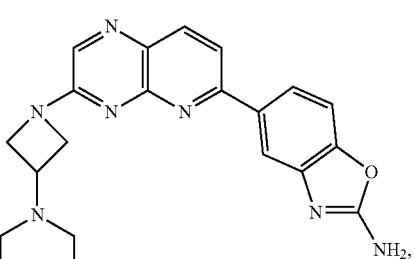
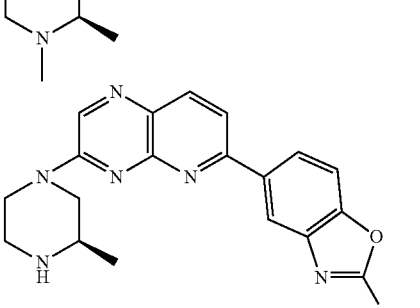
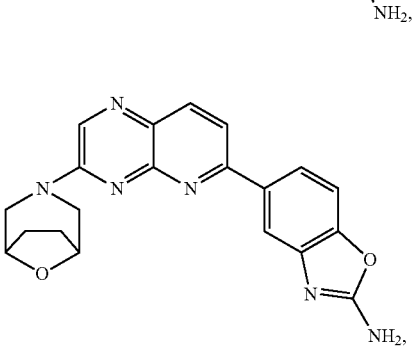
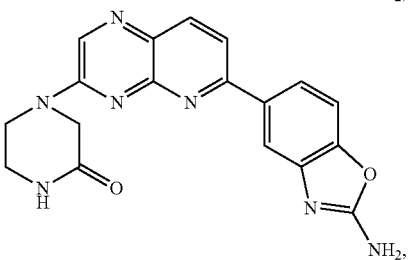

191
-continued
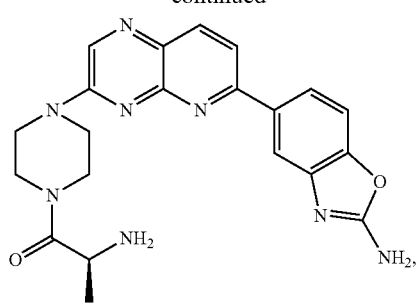
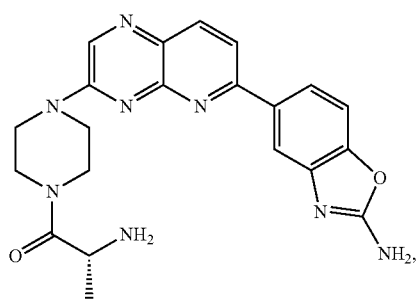
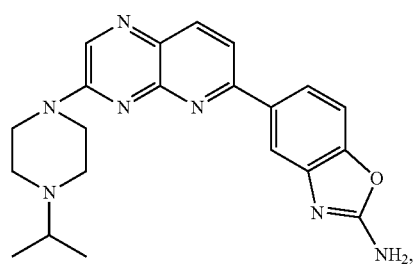
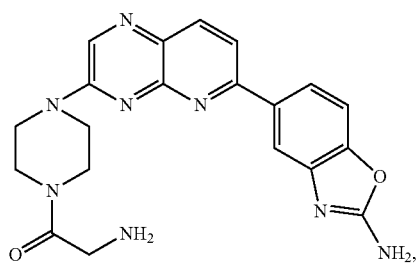
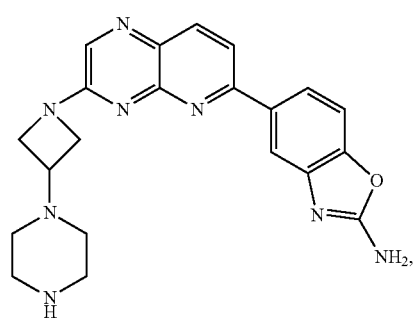
192
-continued
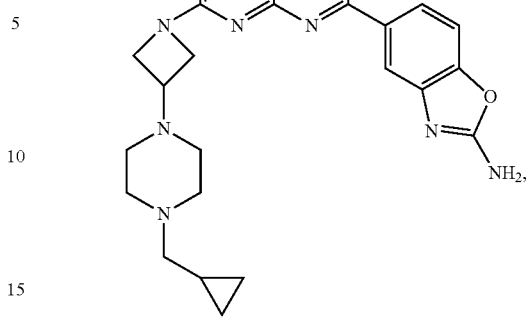
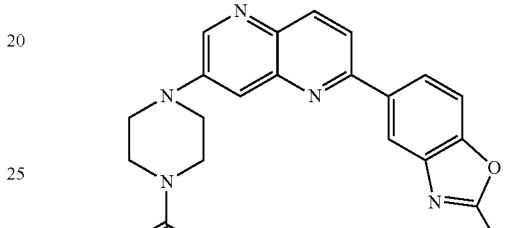
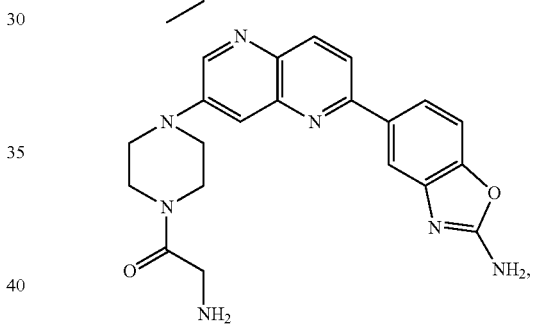
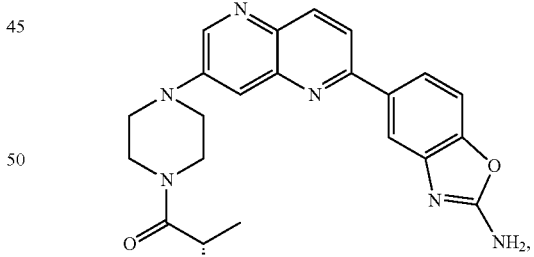
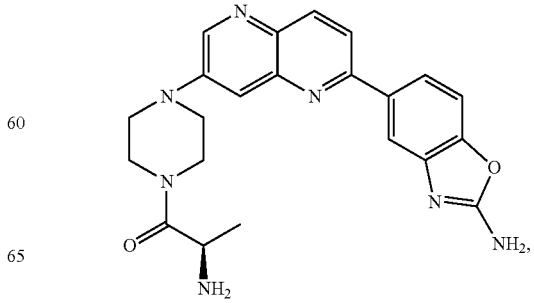

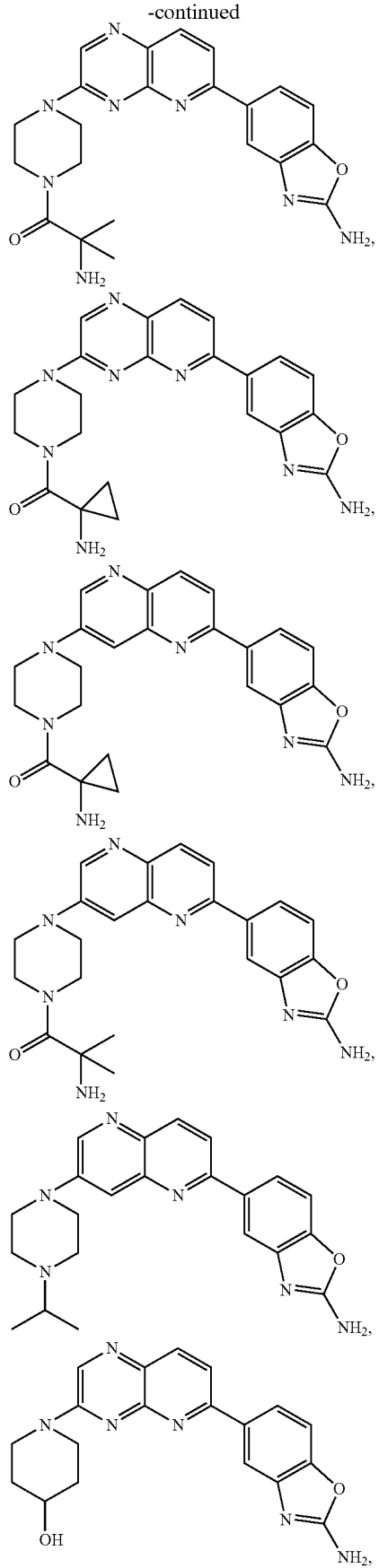
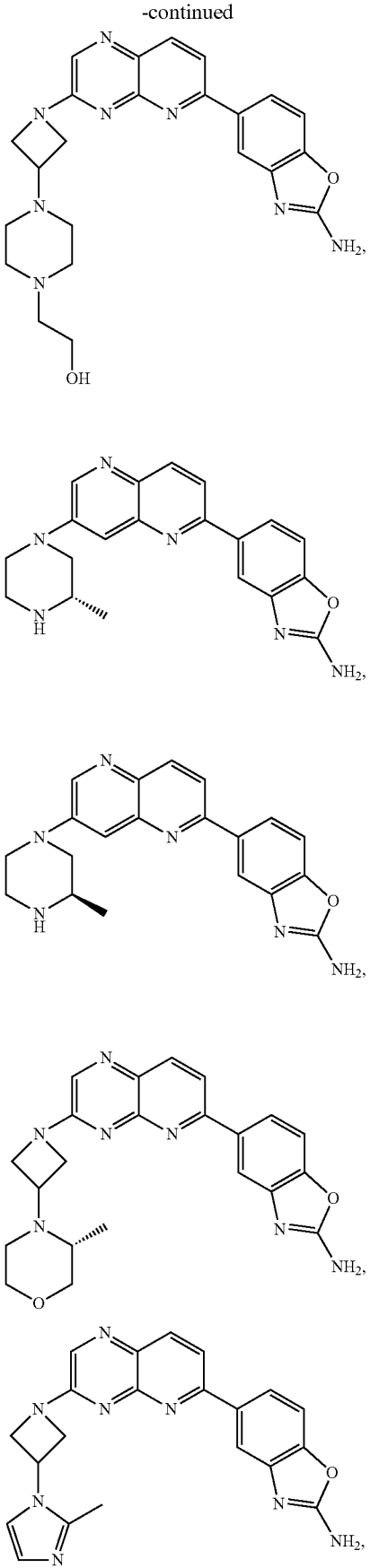

195
-continued
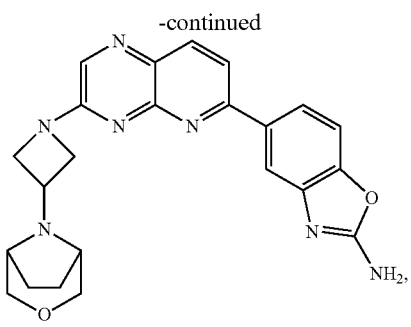
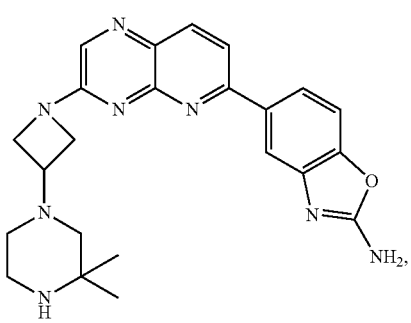
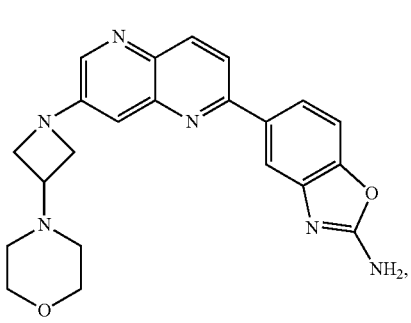
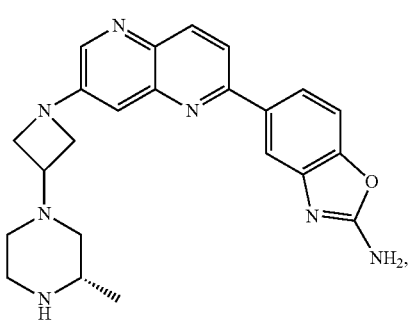
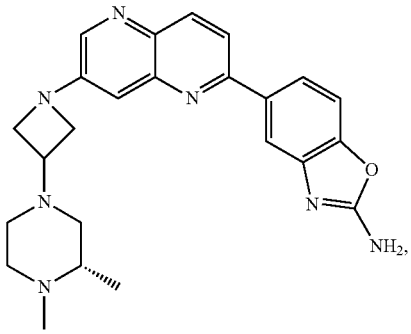
196
-continued
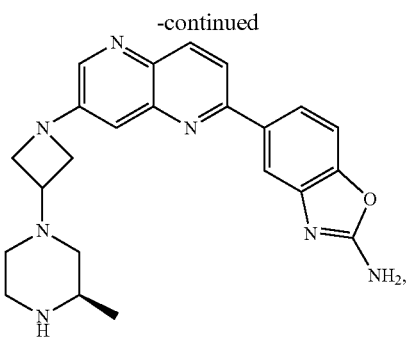
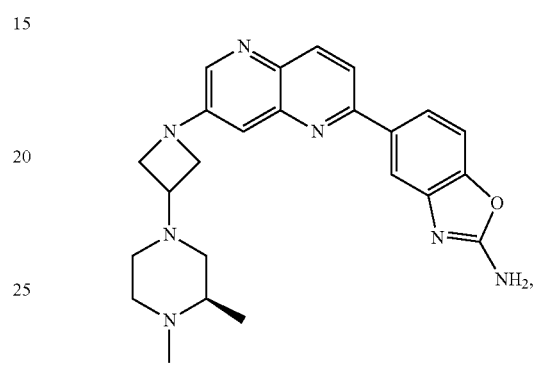
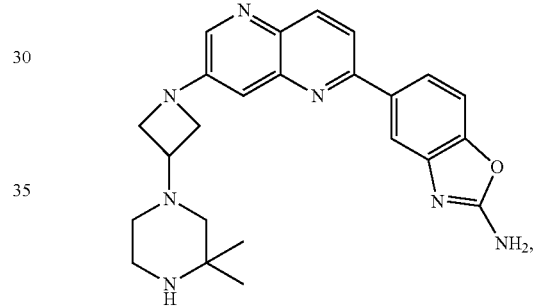
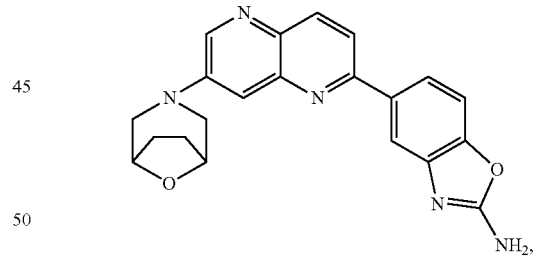
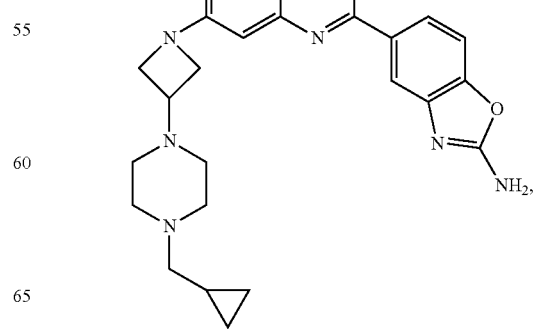

197
-continued
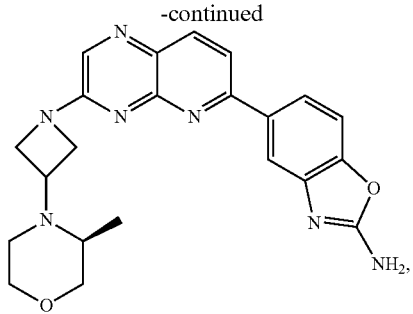
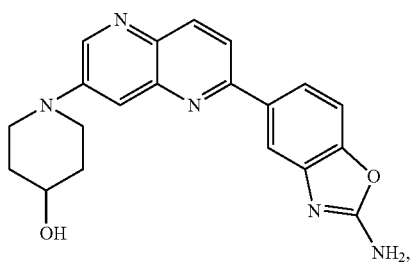
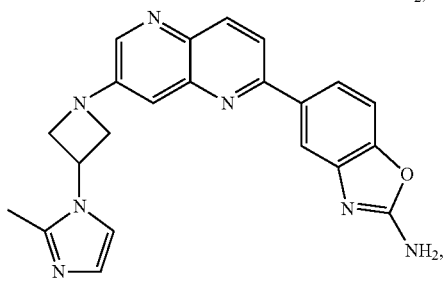
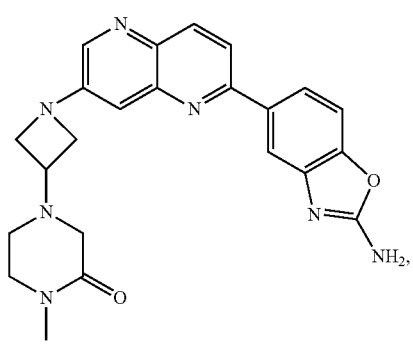
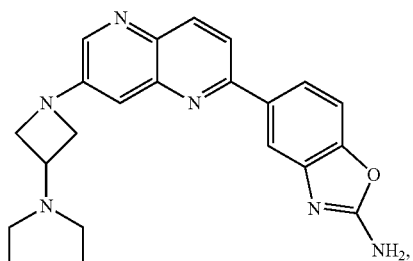
198
-continued
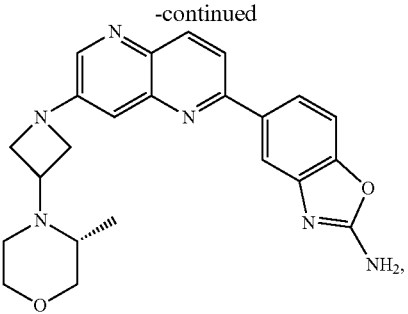
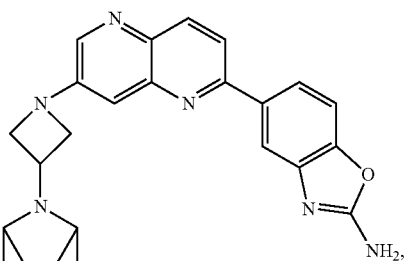
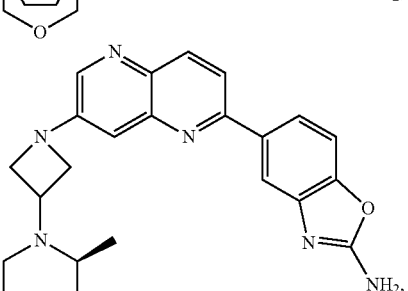
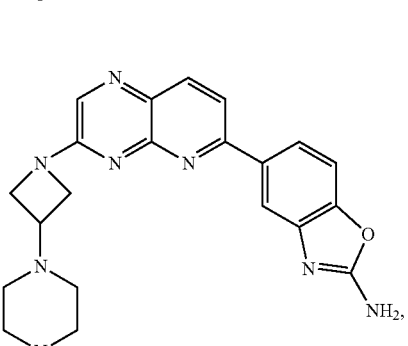
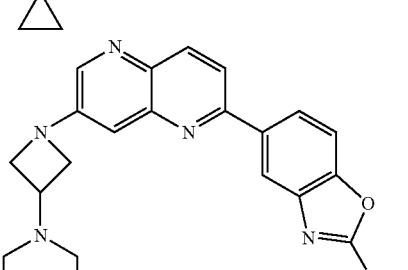

199
-continued
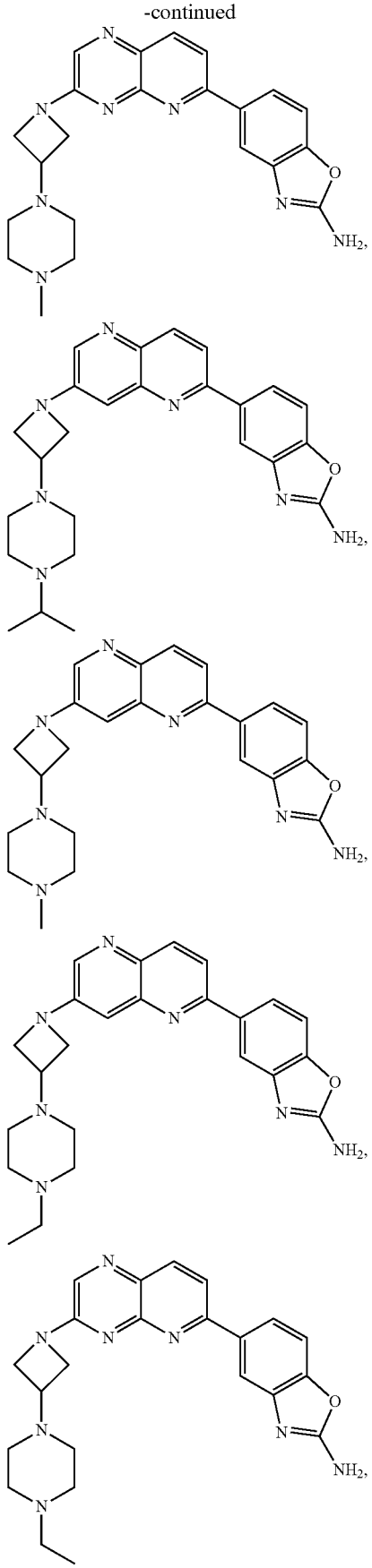
200
-continued
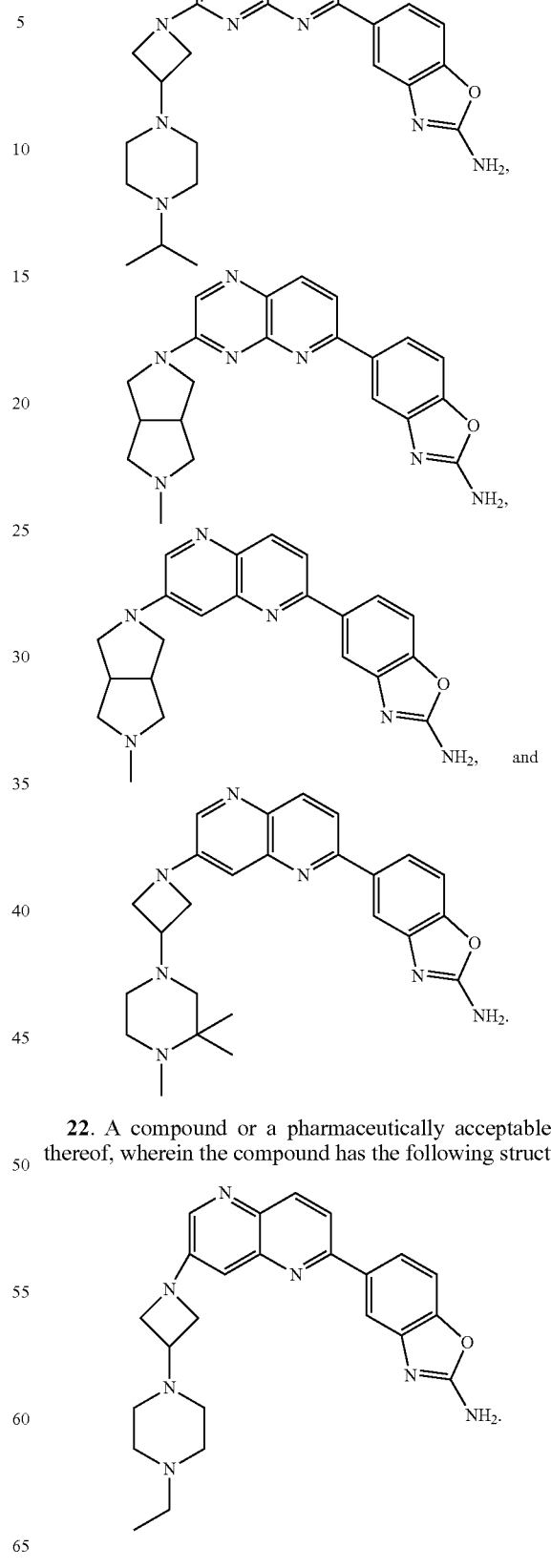
22. A compound or a pharmaceutically acceptable salt thereof, wherein the compound has the following structure:
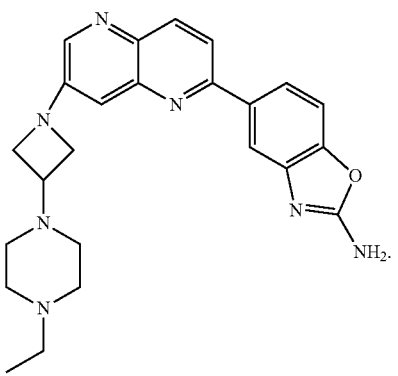 [SMILES: CCN1CCN(C2CN(c3cnc4ccc(-c5ccc6oc(N)nc6c5)nc4c3)C2)CC1]
* * * * *